US008765430B2

(12) United States Patent
Parekh et al.

(10) Patent No.: US 8,765,430 B2
(45) Date of Patent: Jul. 1, 2014

(54) ENHANCING FERMENTATION OF STARCH- AND SUGAR-BASED FEEDSTOCKS

(71) Applicant: Sweetwater Energy, Inc., Rochester, NY (US)

(72) Inventors: Sarad Parekh, Pittsford, NY (US); Carl P. Felice, Churchville, NY (US); Benjamin Stauber, Rochester, NY (US)

(73) Assignee: Sweetwater Energy, Inc., Rochester, NY (US)

( * ) Notice: Subject to any disclaimer, the term of this patent is extended or adjusted under 35 U.S.C. 154(b) by 0 days.

(21) Appl. No.: 13/731,633

(22) Filed: Dec. 31, 2012

(65) Prior Publication Data

US 2013/0210101 A1    Aug. 15, 2013

Related U.S. Application Data

(60) Provisional application No. 61/597,347, filed on Feb. 10, 2012, provisional application No. 61/648,567, filed on May 17, 2012.

(51) Int. Cl.
*C12P 7/10* (2006.01)
*C12P 7/06* (2006.01)

(52) U.S. Cl.
USPC .......................................... 435/165; 435/161

(58) Field of Classification Search
CPC ........... Y02E 50/16; Y02E 50/17; C12P 7/10; C12P 7/06; C12P 7/08
See application file for complete search history.

(56) References Cited

U.S. PATENT DOCUMENTS

| | | |
|---|---|---|
| 4,048,341 A | 9/1977 | Lagerstrom et al. |
| 4,070,232 A | 1/1978 | Funk |
| 4,182,780 A | 1/1980 | Lagerstrom et al. |
| 4,201,596 A | 5/1980 | Church et al. |
| 4,326,032 A | 4/1982 | Grove |
| 4,350,766 A | 9/1982 | Mehlberg |
| 4,395,488 A | 7/1983 | Rowe |
| 4,414,330 A | 11/1983 | Zucker et al. |
| 4,447,534 A | 5/1984 | Moebus et al. |
| 4,478,854 A | 10/1984 | Adler-Nissen et al. |
| 4,520,105 A | 5/1985 | Sinner et al. |
| 4,600,590 A | 7/1986 | Dale |
| 4,612,286 A | 9/1986 | Sherman et al. |
| 4,615,742 A | 10/1986 | Wright |
| 4,644,060 A | 2/1987 | Chou |
| 4,650,689 A | 3/1987 | Hedrick |
| 4,806,475 A | 2/1989 | Gould |
| 5,037,663 A | 8/1991 | Dale |
| 5,144,008 A | 9/1992 | Ikeda et al. |
| 5,171,592 A | 12/1992 | Holtzapple et al. |
| 5,177,008 A | 1/1993 | Kampen |
| 5,177,009 A | 1/1993 | Kampen |
| 5,473,061 A | 12/1995 | Bredereck et al. |
| 5,693,296 A | 12/1997 | Holtzapple et al. |
| 5,726,046 A | 3/1998 | Farone et al. |
| 5,846,787 A | 12/1998 | Ladisch et al. |
| 5,865,898 A | 2/1999 | Holtzapple et al. |
| 5,916,780 A | 6/1999 | Foody et al. |
| 5,939,544 A | 8/1999 | Karstens et al. |
| 5,969,189 A | 10/1999 | Holtzapple et al. |
| 5,986,133 A | 11/1999 | Holtzapple et al. |
| 6,043,392 A | 3/2000 | Holtzapple et al. |
| 6,106,888 A | 8/2000 | Dale et al. |
| 6,176,176 B1 | 1/2001 | Dale et al. |
| 6,258,175 B1 | 7/2001 | Lightner |
| 6,262,313 B1 | 7/2001 | Holtzapple et al. |
| 6,332,542 B2 | 12/2001 | Bilodeau et al. |
| 6,365,732 B1 | 4/2002 | Van Thorre |
| 6,416,621 B1 | 7/2002 | Karstens |
| 6,478,965 B1 | 11/2002 | Holtzapple et al. |
| 6,509,180 B1 | 1/2003 | Verser et al. |
| 7,109,005 B2 | 9/2006 | Eroma et al. |
| 7,198,925 B2 | 4/2007 | Foody |
| 7,503,981 B2 | 3/2009 | Wyman et al. |
| 7,807,419 B2 | 10/2010 | Hennessey et al. |
| 7,909,895 B2 | 3/2011 | Dickinson et al. |
| 7,932,063 B2 | 4/2011 | Dunson, Jr. et al. |
| 7,932,065 B2 | 4/2011 | Medoff |
| 7,935,840 B2 | 5/2011 | Leveson et al. |
| 8,103,385 B2 | 1/2012 | Macharia et al. |
| 8,110,383 B2 | 2/2012 | Jonsson et al. |
| 8,123,864 B2 | 2/2012 | Christensen et al. |
| 8,168,840 B2 | 5/2012 | Brady et al. |
| 8,323,923 B1 | 12/2012 | Horton |
| 8,328,947 B2 | 12/2012 | Anand et al. |

(Continued)

FOREIGN PATENT DOCUMENTS

CA    1267407 B    4/1990
EP    0105937 B1    11/1987

(Continued)

OTHER PUBLICATIONS

U.S. Appl. No. 13/686,477, filed Nov. 27, 2012, Parekh et al.
U.S. Appl. No. 13/724,763, filed Dec. 21, 2012, Parekh et al.
U.S. Appl. No. 13/793,860, filed Mar. 11, 2013, Horton.
U.S. Appl. No. 13/842,941, filed Mar. 15, 2013, Parekh et al.
Alcohol and Tobacco Tax and Trade Bureau, treasury. 27 C.F.R. §19.134 Bonded warehouse not on premises qualified for production of spirits, p. 381, Apr. 1, 1997 revision.
Boggan. 2003. Alcohol, Chemistry and You Sources and Uses of Ethyl Alcohol. Kennesaw State University, pp. 1-5, Printed May 17, 2010. http://www.chemcases.com/alcohol/alc-03.htm/.
Brigham, et al. Bacterial Carbon Storage to Value Added Products. J Microbial Biochem Technol 2011, S3-002.
Dowe, et al (SSF Experimental Protocols—Lignocellulosic Biomass Hydrolysis and Fermentation. Laboratory Analytical Procedure (LAP), Issue Date: Oct. 30, 2001. National Renewable Energy Laboratory, 1617 Cole Boulevard, Golden, Colorado 80401-3393, 76 Pages).

(Continued)

*Primary Examiner* — Jon P Weber
*Assistant Examiner* — Charles Zoltan Constantine
(74) *Attorney, Agent, or Firm* — Wilson Sonsini Goodrich & Rosati, P.C.

(57) ABSTRACT

Provided are methods, systems, and compositions for increasing the rate and/or yield of fermentation processes using blended feedstocks. Also provided are methods, systems, and compositions for decreasing the yield of one or more undesirable products during fermentation.

25 Claims, 11 Drawing Sheets

(56) References Cited

U.S. PATENT DOCUMENTS

| | | |
|---|---|---|
| 8,426,161 B1 | 4/2013 | Horton |
| 2002/0038058 A1 | 3/2002 | Holtzapple et al. |
| 2002/0164730 A1 | 11/2002 | Ballesteros Perdices et al. |
| 2002/0164731 A1 | 11/2002 | Eroma et al. |
| 2002/0192774 A1 | 12/2002 | Ahring et al. |
| 2002/0197686 A1 | 12/2002 | Lightner |
| 2003/0109011 A1 | 6/2003 | Hood et al. |
| 2003/0199049 A1 | 10/2003 | Nguyen et al. |
| 2003/0221361 A1 | 12/2003 | Russell et al. |
| 2003/0224088 A1 | 12/2003 | Burdick |
| 2004/0152881 A1 | 8/2004 | Holtzapple et al. |
| 2004/0168960 A1 | 9/2004 | Holtzapple et al. |
| 2004/0171136 A1 | 9/2004 | Holtzapple et al. |
| 2005/0054064 A1 | 3/2005 | Talluri et al. |
| 2005/0244934 A1 | 11/2005 | Foody et al. |
| 2005/0272134 A1 | 12/2005 | Hughes |
| 2006/0003064 A1 | 1/2006 | James |
| 2006/0024801 A1 | 2/2006 | Holtzapple et al. |
| 2006/0032113 A1 | 2/2006 | Whitney |
| 2006/0069244 A1 | 3/2006 | Holtzapple et al. |
| 2006/0188980 A1 | 8/2006 | Holtzapple et al. |
| 2006/0211101 A1 | 9/2006 | Chotani et al. |
| 2006/0251764 A1 | 11/2006 | Abbas et al. |
| 2006/0281157 A1 | 12/2006 | Chotani et al. |
| 2007/0037259 A1 | 2/2007 | Hennessey et al. |
| 2007/0118916 A1 | 5/2007 | Puzio et al. |
| 2007/0148750 A1 | 6/2007 | Hoshino et al. |
| 2007/0190626 A1 | 8/2007 | Wilkening et al. |
| 2007/0275447 A1 | 11/2007 | Lewis et al. |
| 2008/0014617 A1 | 1/2008 | Cerea |
| 2008/0121359 A1 | 5/2008 | Holtzapple et al. |
| 2008/0176301 A1 | 7/2008 | Granda et al. |
| 2008/0227162 A1 | 9/2008 | Varanasi et al. |
| 2008/0280338 A1 | 11/2008 | Hall et al. |
| 2009/0042259 A1 | 2/2009 | Dale et al. |
| 2009/0043686 A1 | 2/2009 | Matsumoto |
| 2009/0064566 A1 | 3/2009 | Brummerstedt Iversen et al. |
| 2009/0098617 A1 | 4/2009 | Burke et al. |
| 2009/0181434 A1 | 7/2009 | Aikens et al. |
| 2009/0298149 A1 | 12/2009 | Wang et al. |
| 2010/0021980 A1 | 1/2010 | McDonald et al. |
| 2010/0041119 A1* | 2/2010 | Christensen et al. ......... 435/162 |
| 2010/0055741 A1 | 3/2010 | Galvez, II et al. |
| 2010/0144001 A1 | 6/2010 | Horton |
| 2010/0221805 A1 | 9/2010 | Kelly |
| 2010/0221819 A1 | 9/2010 | Foody et al. |
| 2010/0227369 A1 | 9/2010 | Narendranath et al. |
| 2010/0317053 A1 | 12/2010 | Stromberg et al. |
| 2011/0079219 A1 | 4/2011 | McDonald et al. |
| 2011/0081689 A1 | 4/2011 | Flanegan et al. |
| 2011/0114765 A1 | 5/2011 | Brady et al. |
| 2011/0129886 A1 | 6/2011 | Howard et al. |
| 2011/0201084 A1 | 8/2011 | Wyman et al. |
| 2011/0223641 A1 | 9/2011 | Stephanopoulos et al. |
| 2011/0244499 A1 | 10/2011 | Realff et al. |
| 2011/0258911 A1 | 10/2011 | Hanson et al. |
| 2011/0258913 A1 | 10/2011 | Stamires et al. |
| 2011/0275860 A1 | 11/2011 | Beldring et al. |
| 2012/0006320 A1 | 1/2012 | Nguyen |
| 2012/0037325 A1 | 2/2012 | Beldring et al. |
| 2012/0041186 A1 | 2/2012 | Pschorn et al. |
| 2012/0100045 A1 | 4/2012 | Beldring et al. |
| 2012/0100577 A1 | 4/2012 | Medoff et al. |
| 2012/0122162 A1 | 5/2012 | Romero et al. |
| 2012/0190092 A1 | 7/2012 | Jaquess et al. |
| 2012/0214216 A1 | 8/2012 | Brady et al. |
| 2013/0274455 A1 | 10/2013 | Parekh et al. |
| 2013/0323830 A1 | 12/2013 | Horton |

FOREIGN PATENT DOCUMENTS

| | | |
|---|---|---|
| EP | 1259466 B1 | 10/2008 |
| EP | 1307735 B1 | 11/2008 |
| EP | 1299170 B1 | 8/2010 |
| JP | 2006-149343 A | 6/2006 |
| WO | WO 01/32715 A1 | 5/2001 |
| WO | WO 01/60752 A1 | 8/2001 |
| WO | WO 02/00324 A1 | 1/2002 |
| WO | WO 02/01220 A2 | 1/2002 |
| WO | WO 02/01220 A3 | 9/2002 |
| WO | WO 2004/081193 A2 | 9/2004 |
| WO | WO 2004/113551 A1 | 12/2004 |
| WO | WO 2005/087937 A2 | 9/2005 |
| WO | WO 2005/118828 A1 | 12/2005 |
| WO | WO 2006/024242 A1 | 3/2006 |
| WO | WO 2006/101832 A2 | 9/2006 |
| WO | WO 2007/009463 A2 | 1/2007 |
| WO | WO 2007/009463 A3 | 7/2007 |
| WO | WO 2008/020901 A2 | 2/2008 |
| WO | WO 2006/101832 A3 | 4/2009 |
| WO | WO 2009/063138 A2 | 5/2009 |
| WO | WO 2009/087680 A2 | 7/2009 |
| WO | WO 2010/056940 A2 | 5/2010 |
| WO | WO 2010/115488 A1 | 10/2010 |
| WO | WO 2010/123932 A1 | 10/2010 |
| WO | WO 2011/103033 A1 | 8/2011 |
| WO | WO 2012/051523 A1 | 4/2012 |
| WO | WO 2012/099967 A1 | 7/2012 |

OTHER PUBLICATIONS

Dowe, et al. 2001. SSF Experimental Protocols—Lignocellulosic Biomass Hydrolysis and Fermentation Laboratory Analytical Procedure (LAP), National Renewable Energy Laboratory. 1617 Cole Boulevard, Golden, Colorado. Issue Date: Oct. 30, 2001, pp. 1-18.

Gum, et al. Structural characterization of a glycoprotein cellulase, 1,4-beta-D-glucan cellubiohydrolase C from trichodermaviride. Biochem. Biophys. Acta. 1976; 446:370-86.

International search report and written opinion dated Jan. 26, 2010 for PCT/US2009/67221.

Jones, et al. (1994, Ethanolic Fermentation of Blackstrap Molasses and Sugarcane Juice Using Very High Gravity Technology. J. Agric. Food Chem, vol. 42, pp. 1242-1246).

Mosier, et al. Features of promising technologies for pretreatment of lignocellulosic biomass. Bioresour Technol. Apr. 2005;96(6):673-86.

Notice of allowance dated Oct. 15, 2012 for U.S. Appl. No. 11/974,129.

Office action dated Feb. 20, 2013 for U.S. Appl. No. 13/686,477.
Office action dated Mar. 20, 2013 for U.S. Appl. No. 12/633,555.
Office action dated May 24, 2010 for U.S. Appl. No. 11/974,129.
Office action dated Jul. 6, 2012 for U.S. Appl. No. 11/974,129.
Office action dated Oct. 3, 2012 for U.S. Appl. No. 12/633,555.
Office action dated Nov. 8, 2010 for U.S. Appl. No. 11/974,129.

Shapouri et al. 2006. The Economic Feasibility of Ethanol Production From Sugar in the United States, USDA, 78 Pages, Jul. 2006.

Sluiter, et al. Determination of structural carbohydrates and lignin in biomass. National Renewable Energy Laboratory. Technical report NREL/TP-510-42618. Revised Jun. 2010.

Taylor. From Raw Sugar to Raw materials. Chemical innovation. 2000; 30:45-48.

USDA, "The Economic Feasibility of Ethanol Production From Sugar in the United States"; Jul. 2006, 69 Pages.

Varhegyi, et al. (1989. Kinetics of the thermal decomposition of cellulose, hemicellulose, and sugarcane bagasse. Energy Fuels, vol. 3, No. 3, pp. 329-335).

Dale, et al. Hydrolysis of lignocellulosics at low enzyme levels: Application of the AFEX process. Bioresource Technology. Apr. 1996; 56(1):111-116.

Dasari, et al. The effect of particle size on hydrolysis reaction rates and rheological properties in cellulosic slurries. Appl Biochem Biotechnol. Apr. 2007;136-140(1-12):289-99. doi: 10.1007/s12010-007-9059-x.

Felix et al. In vitro and in vivo digestibility of soya-bean straw treated with various alkalis. Anim Prod. 1990; 51:47-61.

Gibreel, et al. Fermentation of barley by using *Saccharomyces cerevisiae*: examination of barley as a feedstock for bioethanol production and value-added products. Appl Environ Microbiol. Mar. 2009;75(5):1363-72. doi: 10.1128/AEM.01512-08. Epub Dec. 29, 2008.

(56) References Cited

OTHER PUBLICATIONS

Kim, et al. Lime pretreatment and enzymatic hydrolysis of corn stover. Bioresour Technol. Dec. 2005;96(18):1994-2006.

Kim, et al. Pretreatment and fractionation of corn stover by ammonia recycle percolation process. Bioresour Technol. Dec. 2005;96(18):2007-13.

Larsson, et al. Comparison of different methods for the detoxification of lignocellulose hydrolyzates of spruce. Applied Biochemistry and Biotechnology. 1999; 77-79:91-103.

Lloyd, et al. Combined sugar yields for dilute sulfuric acid pretreatment of corn stover followed by enzymatic hydrolysis of the remaining solids. Bioresour Technol. Dec. 2005;96(18):1967-77.

Mosier, et al. Optimization of pH controlled liquid hot water pretreatment of corn stover. Bioresour Technol. Dec. 2005;96(18):1986-93.

Nevoigt, et al. Osmoregulation and glycerol metabolism in the yeast *Saccharomyces cerevisiae*. FEMS Microbiol Rev. Nov. 1997;21(3):231-41.

Palmqvist, et al. Fermentation of lignocellulosic hydrolysates. I: inhibition and detoxification. Bioresource Technology. 2000; 74(1):17-24.

Parekh, et al. Production of glycerol by hansenula anomala. Biotechnol Bioeng. Jul. 1985;27(7):1089-91.

Santoro, et al. A High-throughput Platform for Screening Milligram Quantities of Plant Biomass for Lignocellulose Digestibility. Bioenerg. Res. Jan. 2010; 3:93-102.

Waiss, et al. Improving Digestibility of Straws for Ruminant Feed by Aqueous Ammonia. Journal of Animal Science. 1972;35(1):109-112.

Waltermann, et al. *Rhodococcus opacus* strain PD630 as a new source of high-value single-cell oil? Isolation and characterization of triacylglycerols and other storage lipids. Microbiology. 2000; 146:1143-1149.

U.S. Appl. No. 14/050,244, filed Oct. 9, 2013, Chesonis et al.

International search report and written opinion dated Jul. 26, 2013 for PCT Application No. US2013/032955.

Office action dated Oct. 18, 2013 for U.S. Appl. No. 13/724,763.

Agbor, et al. Biomass pretreatment: fundamentals toward application. Biotechnol Adv. Nov.-Dec. 2011;29(6):675-85. doi: 10.1016/j.biotechadv.2011.05.005. Epub May 23, 2011.

International search report and written opinion dated May 30, 2013 for PCT/US2013/025457.

International search report and written opinion dated Jun. 20, 2013 for PCT/US2013/036497.

Office action dated Mar. 24, 2014 for U.S. Appl. No. 13/724,763.

* cited by examiner

ENHANCING FERMENTATION OF STARCH- AND SUGAR-BASED FEEDSTOCKS

CROSS-REFERENCE

This application claims the benefit of U.S. Provisional Application No. 61/597,347, filed Feb. 10, 2012, and U.S. Provisional Application No. 61/648,567, filed May 17, 2012, each of which application is incorporated herein by reference in its entirety.

BACKGROUND OF THE INVENTION

The demand for renewable fuels and chemical is growing significantly and is required to reduce reliance on petroleum-based products and to lower gas emissions. At the same time, interest in biofuels, such as ethanol, as an alternative to petroleum has greatly increased, in part due to the desire to promote domestic rural economics. Ethanol is the most commonly used biofuel, and current U.S. biofuel is almost exclusively derived from corn. To meet some of the higher ethanol production goals would require more corn than the United States currently produces. At the same time, a concern over the use of food crops for fuel is an obstacle to use of further corn for ethanol. Another obstacle to widespread adoption of biofuels and bio-products is the economic cost of producing the ethanol. A major contributing factor to this cost is transportation of biomass feedstock from the location where feedstock is grown to the location where it is processed into biofuels and chemicals. More efficient use of starch fermentation, supplemented with sugars from non-starch cellulosic materials would help defray these costs. Although the supplementation of cellulosic sugars assists in starch production, it would be helpful to optimize this process in a manner wherein fermenting organisms can utilize the maximum amount of sugar provided to them.

SUMMARY OF THE INVENTION

Disclosed herein are methods of producing one or more fermentation end-products comprising: (a) combining a first biomass with one or more cellulosic-derived C6 monosaccharides to produce a blended feedstock in a broth; (b) contacting the blended feedstock with one or more biocatalysts; and (c) fermenting the first biomass and the one or more cellulosic-derived C6 monosaccharides for sufficient time to produce one or more fermentation end-products from the blended feedstock, wherein a yield of at least one of the one or more fermentation end-products is increased relative to fermentation of the first biomass without the one or more cellulosic-derived C6 monosaccharides. In some embodiments, the yield of the at least one of the one or more fermentation end-products is increased by about 1% to about 100% relative to fermentation of the first biomass without the one or more cellulosic-derived C6 monosaccharides. In some embodiments, at least one of the one or more fermentation end-products is produced at a rate that is faster relative to fermentation of the first biomass without the one or more cellulosic-derived C6 monosaccharides. In some embodiments, at least one of the one or more fermentation end-products is produced at a rate that is about 1% to about 100% faster relative to fermentation of the first biomass without the one or more cellulosic-derived C6 monosaccharides. In some embodiments, the one or more cellulosic-derived C6 monosaccharides are at a concentration that differs from a concentration of saccharides in the first biomass by less than +/−50%, wherein the concentration of saccharides in the first biomass is in monosaccharide equivalents. In some embodiments, the one or more cellulosic-derived C6 monosaccharides are at a concentration that differs from a concentration of saccharides in the first biomass by less than +/−25%, wherein the concentration of saccharides in the first biomass is in monosaccharide equivalents. In some embodiments, the one or more fermentation end-products comprise one or more alcohols. In some embodiments, the one or more fermentation end-products comprise ethanol. In some embodiments, the method is a fed-batch fermentation wherein the one or more cellulosic-derived C6 monosaccharides are added over time. In some embodiments, the one or more cellulosic-derived C6 monosaccharides are added at a rate of from about 0.01 mL/min/L of broth to about 5 mL/min/L of broth during the fermenting. In some embodiments, a yield of one or more other products is decreased relative to a non-fed batch fermentation. In some embodiments, the yield of the one or more other products is decreased by about 1% to about 100% relative to the non-fed batch fermentation. In some embodiments, the one or more other products comprise one or more polyols or sugar alcohols. In some embodiments, the one or more other products comprise methanol, glycol, glycerol, erythritol, threitol, arabitol, xylitol, ribitol, mannitol, sorbitol, dulcitol, fucitol, iditol, inositol, volemitol, isomalt, maltitol, lactitol, polyglycitol, or a combination thereof. In some embodiments, the one or more other products comprise glycerol. In some embodiments, the first biomass comprises non-cellulosic sugars. In some embodiments, the first biomass comprises non-cellulosic oligosaccharides. In some embodiments, the first biomass comprises starch. In some embodiments, the first biomass comprises corn, corn mash, sugar cane, sugar beets, sugar palms, sweet sorghum, nypa palm, cassaya, rice, milo, sorghum, sweet potatoes, wheat, molasses, tubers, roots, stems, whole grains, barley, rye, milo, sago, cassaya, tapioca, rice peas, beans, potatoes, beets, fruits, or a combination thereof. In some embodiments, the one or more cellulosic-derived C6 monosaccharides are produced from the pretreatment and/or hydrolysis of cellulose, hemicellulose, or lignocellulose material. In some embodiments, the one or more cellulosic-derived C6 monosaccharides are produced by the pretreatment and/or hydrolysis of a second biomass comprising cellulose, hemicellulose, or lignocellulose. In some embodiments, the second biomass comprises corn, corn syrup, corn stover, corn cobs, molasses, silage, grass, straw, grain hulls, bagasse, distiller's grains, distiller's dried solubles, distiller's dried grains, condensed distiller's solubles, distiller's wet grains, distiller's dried grains with solubles, wood, bark, sawdust, paper, poplars, willows, switchgrass, alfalfa, prairie bluestem, algae, fruit peels, pits, sorghum, sweet sorghum, sugar cane, switch grass, rice, rice straw, rice hulls, wheat, wheat straw, barley, barley straw, bamboo, seeds, seed hulls, oats, oat hulls, food waste, municipal sewage waste, or a combination thereof. In some embodiments, the one or more biocatalysts comprise one or more fermenting microorganisms. In some embodiments, the one or more biocatalysts comprise one or more yeasts and/or one or more bacteria. In some embodiments, the one or more biocatalysts comprise one or more yeasts. In some embodiments, the one or more biocatalysts comprise one or more strains of *Saccharomyces cerevisiae*. In some embodiments, at least one of the one or more biocatalysts is a genetically-modified yeast that ferments C5 and C6 saccharides. In some embodiments, at least one of the one or more biocatalysts is a bacteria that hydrolyzes and/or ferments C5 and C6 saccharides. In some embodiments, at least one of the one or more biocatalysts is a hydrolytic enzyme. In some embodiments, the one or more biocatalysts comprise an endoglucanase, an exoglucanase, a cellobiohydrolase, a cellulase, a beta-glucosidase, a glycoside hydrolase, a glycosyltransferase, a lyase, an esterase, a glucamylase, or a combination thereof. In some embodiments, at least one of the one or more biocatalysts is an enzyme that hydrolyzes starch. In some embodiments, at least one of the one or more biocatalysts is an alpha-amylase, glucoamylase, beta-amylase, exo-alpha-1,4-glucanase, or pullulanase. In some embodiments, the one or more biocatalysts comprise at least one fermenting microorganism and at least one hydrolytic enzyme. In some embodiments, the one or more biocatalysts comprise at least one fermenting microorganism that is a yeast or bacteria and at least one enzyme that hydrolyzes starch. In some embodiments, the blended feedstock comprises less than 100 g/L monosaccharides prior to contacting with the one or more biocatalysts. In some embodiments, the blended feedstock comprises from about 1 g/L to about 100 g/L monosaccharides prior to contacting with the one or more biocatalysts. In some embodiments, the first biomass and the one or more cellulosic-derived C6 monosaccharides are combined in a ratio of from about 50:50 to 99:1 (first biomass: cellulosic-derived C6 monosaccharides) by volume or by weight:volume. In some embodiments, the first biomass and the one or more cellulosic-derived C6 monosaccharides are combined in a ratio of about 80:20 (first biomass: cellulosic-derived C6 monosaccharides) by volume or by weight:volume. In some embodiments, the first biomass and the one or more cellulosic-derived C6 monosaccharides are combined in a ratio of about 90:10 (first biomass: cellulosic-derived C6 monosaccharides) by volume or by weight:volume. In some embodiments, the blended feedstock comprises from about 10% to about 50% solids from the first biomass. In some embodiments, the blended feedstock comprises from about 20% to about 40% solids from the first biomass. In some embodiments, the blended feedstock comprises from about 30% to about 36% solids from the first biomass. In some embodiments, the one or more cellulosic-derived C6 monosaccharides are at a concentration of from about 10% to about 70% w/v prior to combining with the first biomass. In some embodiments, the one or more cellulosic-derived C6 monosaccharides are at a concentration of from about 20% to about 50% w/v prior to combining with the first biomass.

Also provided are fermentation end-products produced by the methods disclosed herein. In some embodiments, the fermentation end-product is an alcohol. In some embodiments, the fermentation end-product is ethanol.

Also disclosed herein are methods of producing one or more fermentation end-products comprising: (a) combining a first biomass with one or more cellulosic-derived C6 monosaccharides to produce a blended feedstock in a broth; (b) contacting the blended feedstock with one or more biocatalysts; and (c) fermenting the first biomass and the one or more cellulosic-derived C6 monosaccharides for sufficient time to produce one or more fermentation end-products from the blended feedstock, wherein at least one of the one or more fermentation end-products is produced at a rate that is faster relative to fermentation of the first biomass without the one or more cellulosic-derived C6 monosaccharides. In some embodiments, a yield of at least one of the one or more fermentation end-products is increased relative to fermentation of the first biomass without the one or more cellulosic-derived C6 monosaccharides. In some embodiments, a yield of at least one of the one or more fermentation end-products is increased by about 1% to about 100% relative to fermentation of the first biomass without the one or more cellulosic-derived C6 monosaccharides. In some embodiments, the rate that the at least one of the one or more fermentation end-products is produced is about 1% to about 100% faster relative to fermentation of the first biomass without the one or more cellulosic-derived C6 monosaccharides. In some embodiments, the one or more cellulosic-derived C6 monosaccharides are at a concentration that differs from a concentration of saccharides in the first biomass by less than +/−50%, wherein the concentration of saccharides in the first biomass is in monosaccharide equivalents. In some embodiments, the one or more cellulosic-derived C6 monosaccharides are at a concentration that differs from a concentration of saccharides in the first biomass by less than +/−25%, wherein the concentration of saccharides in the first biomass is in monosaccharide equivalents. In some embodiments, the one or more fermentation end-products comprise one or more alcohols. In some embodiments, the one or more fermentation end-products comprise ethanol. In some embodiments, the method is a fed-batch fermentation wherein the one or more cellulosic-derived C6 monosaccharides are added over time. In some embodiments, the one or more cellulosic-derived C6 monosaccharides are added at a rate of from about 0.01 mL/min/L of broth to about 5 mL/min/L of broth during the fermenting. In some embodiments, a yield of one or more other products is decreased relative to a non-fed batch fermentation. In some embodiments, the yield of the one or more other products is decreased by about 1% to about 100% relative to the non-fed batch fermentation. In some embodiments, the one or more other products comprise one or more polyols or sugar alcohols. In some embodiments, the one or more other products comprise methanol, glycol, glycerol, erythritol, threitol, arabitol, xylitol, ribitol, mannitol, sorbitol, dulcitol, fucitol, iditol, inositol, volemitol, isomalt, maltitol, lactitol, polyglycitol, or a combination thereof. In some embodiments, the one or more other products comprise glycerol. In some embodiments, the first biomass comprises non-cellulosic sugars. In some embodiments, the first biomass comprises non-cellulosic oligosaccharides. In some embodiments, the first biomass comprises starch. In some embodiments, the first biomass comprises corn, corn mash, sugar cane, sugar beets, sugar palms, sweet sorghum, nypa palm, cassaya, rice, milo, sorghum, sweet potatoes, wheat, molasses, tubers, roots, stems, whole grains, barley, rye, milo, sago, cassaya, tapioca, rice peas, beans, potatoes, beets, fruits, or a combination thereof. In some embodiments, the one or more cellulosic-derived C6 monosaccharides are produced from the pretreatment and/or hydrolysis of cellulose, hemicellulose, or lignocellulose material. In some embodiments, the one or more cellulosic-derived C6 monosaccharides are produced by the pretreatment and/or hydrolysis of a second biomass comprising cellulose, hemicellulose, or lignocellulose. In some embodiments, the second biomass comprises corn, corn syrup, corn stover, corn cobs, molasses, silage, grass, straw, grain hulls, bagasse, distiller's grains, distiller's dried solubles, distiller's dried grains, condensed distiller's solubles, distiller's wet grains, distiller's dried grains with solubles, wood, bark, sawdust, paper, poplars, willows, switchgrass, alfalfa, prairie bluestem, algae, fruit peels, pits, sorghum, sweet sorghum, sugar cane, switch grass, rice, rice straw, rice hulls, wheat, wheat straw, barley, barley straw, bamboo, seeds, seed hulls, oats, oat hulls, food waste, municipal sewage waste, or a combination thereof. In some embodiments, the one or more biocatalysts comprise one or more fermenting microorganisms. In some embodiments, the one or more biocatalysts comprise one or more yeasts and/or one or more bacteria. In some embodiments, the one or more biocatalysts comprise one or more yeasts. In some embodiments, the one or more biocatalysts comprise one or more strains of *Saccharomyces cerevisiae*. In some embodiments, at least one of the one or more biocatalysts is a genetically-modified yeast that ferments C5 and C6 saccharides. In some embodiments, at least one of the one or more biocatalysts is a bacteria that hydrolyzes and/or ferments C5 and C6 saccharides. In some embodiments, at least one of the one or more biocatalysts is a hydrolytic enzyme. In some embodiments, the one or more biocatalysts comprise an endoglucanase, an exoglucanase, a cellobiohydrolase, a cellulase, a beta-glucosidase, a glycoside hydrolase, a glycosyltransferase, a lyase, an esterase, a glucamylase, or a combination thereof. In some embodiments, at least one of the one or more biocatalysts is an enzyme that hydrolyzes starch. In some embodiments, at least one of the one or more biocatalysts is an alpha-amylase, glucoamylase, beta-amylase, exo-alpha-1,4-glucanase, or pullulanase. In some embodiments, the one or more biocatalysts comprise at least one fermenting microorganism and at least one hydrolytic enzyme. In some embodiments, the one or more biocatalysts comprise at least one fermenting microorganism that is a yeast or bacteria and at least one enzyme that hydrolyzes starch. In some embodiments, the blended feedstock comprises less than 100 g/L monosaccharides prior to contacting with the one or more biocatalysts. In some embodiments, the blended feedstock comprises from about 1 g/L to about 100 g/L monosaccharides prior to contacting with the one or more biocatalysts. In some embodiments, the first biomass and the one or more cellulosic-derived C6 monosaccharides are combined in a ratio of from about 50:50 to 99:1 (first biomass: cellulosic-derived C6 monosaccharides) by volume or by weight:volume. In some embodiments, the first biomass and the one or more cellulosic-derived C6 monosaccharides are combined in a ratio of about 80:20 (first biomass: cellulosic-derived C6 monosaccharides) by volume or by weight:volume. In some embodiments, the first biomass and the one or more cellulosic-derived C6 monosaccharides are combined in a ratio of about 90:10 (first biomass: cellulosic-derived C6 monosaccharides) by volume or by weight:volume. In some embodiments, the blended feedstock comprises from about 10% to about 50% solids from the first biomass. In some embodiments, the blended feedstock comprises from about 20% to about 40% solids from the first biomass. In some embodiments, the blended feedstock comprises from about 30% to about 36% solids from the first biomass. In some embodiments, the one or more cellulosic-derived C6 monosaccharides are at a concentration of from about 10% to about 70% w/v prior to combining with the first biomass. In some embodiments, the one or more cellulosic-derived C6 monosaccharides are at a concentration of from about 20% to about 50% w/v prior to combining with the first biomass.

Also disclosed herein are methods of producing one or more fermentation end-products comprising: (a) combining a first biomass with one or more cellulosic-derived C6 monosaccharides to produce a blended feedstock in a broth; (b) contacting the blended feedstock with one or more biocatalysts; and (c) fermenting the first biomass and the one or more cellulosic-derived C6 monosaccharides for sufficient time to produce one or more fermentation end-products from the blended feedstock, wherein the one or more cellulosic-derived C6 monosaccharides are at a concentration that differs from a concentration of saccharides in the first biomass by less than +/−50%, wherein the concentration of saccharides in the first biomass is in monosaccharide equivalents. In some embodiments, a yield of at least one of the one or more fermentation end-products is increased relative to fermentation of the first biomass without the one or more cellulosic-derived C6 monosaccharides. In some embodiments, a yield of at least one of the one or more fermentation end-products is increased by about 1% to about 100% relative to fermentation of the first biomass without the one or more cellulosic-derived C6 monosaccharides. In some embodiments, at least one of the one or more fermentation end-products is produced at a rate that is faster relative to fermentation of the first biomass without the one or more cellulosic-derived C6 monosaccharides. In some embodiments, at least one of the one or more fermentation end-products is produced at a rate that is about 1% to about 100% faster relative to fermentation of the first biomass without the one or more cellulosic-derived C6 monosaccharides. In some embodiments, the concentration of the one or more cellulosic-derived C6 monosaccharides differs from the concentration of saccharides in the first biomass by less than +/−25%, wherein the concentration of saccharides in the first biomass is in monosaccharide equivalents. In some embodiments, the one or more fermentation end-products comprise one or more alcohols. In some embodiments, the one or more fermentation end-products comprise ethanol. In some embodiments, the method is a fed-batch fermentation wherein the one or more cellulosic-derived C6 monosaccharides are added over time. In some embodiments, the one or more cellulosic-derived C6 monosaccharides are added at a rate of from about 0.01 mL/min/L of broth to about 5 mL/min/L of broth during the fermenting. In some embodiments, a yield of one or more other products is decreased relative to a non-fed batch fermentation. In some embodiments, the yield of the one or more other products is decreased by about 1% to about 100% relative to the non-fed batch fermentation. In some embodiments, the one or more other products comprise one or more polyols or sugar alcohols. In some embodiments, the one or more other products comprise methanol, glycol, glycerol, erythritol, threitol, arabitol, xylitol, ribitol, mannitol, sorbitol, dulcitol, fucitol, iditol, inositol, volemitol, isomalt, maltitol, lactitol, polyglycitol, or a combination thereof. In some embodiments, the one or more other products comprise glycerol. In some embodiments, the first biomass comprises non-cellulosic sugars. In some embodiments, the first biomass comprises non-cellulosic oligosaccharides. In some embodiments, the first biomass comprises starch. In some embodiments, the first biomass comprises corn, corn mash, sugar cane, sugar beets, sugar palms, sweet sorghum, nypa palm, cassaya, rice, milo, sorghum, sweet potatoes, wheat, molasses, tubers, roots, stems, whole grains, barley, rye, milo, sago, cassaya, tapioca, rice peas, beans, potatoes, beets, fruits, or a combination thereof. In some embodiments, the one or more cellulosic-derived C6 monosaccharides are produced from the pretreatment and/or hydrolysis of cellulose, hemicellulose, or lignocellulose material. In some embodiments, the one or more cellulosic-derived C6 monosaccharides are produced by the pretreatment and/or hydrolysis of a second biomass comprising cellulose, hemicellulose, or lignocellulose. In some embodiments, the second biomass comprises corn, corn syrup, corn stover, corn cobs, molasses, silage, grass, straw, grain hulls, bagasse, distiller's grains, distiller's dried solubles, distiller's dried grains, condensed distiller's solubles, distiller's wet grains, distiller's dried grains with solubles, wood, bark, sawdust, paper, poplars, willows, switchgrass, alfalfa, prairie bluestem, algae, fruit peels, pits, sorghum, sweet sorghum, sugar cane, switch grass, rice, rice straw, rice hulls, wheat, wheat straw, barley, barley straw, bamboo, seeds, seed hulls, oats, oat hulls, food waste, municipal sewage waste, or a combination thereof. In some embodiments, the one or more biocatalysts comprise one or more fermenting microorganisms. In some embodiments, the one or more biocatalysts comprise one or more yeasts and/or one or more bacteria. In some embodiments, the one or more biocatalysts comprise one or more yeasts. In some embodiments, the one or more biocatalysts comprise one or more strains of *Saccharomyces cerevisiae*. In some embodiments, at least one of the one or more biocatalysts is a genetically-modified yeast that ferments C5 and C6 saccharides. In some embodiments, at least one of the one or more biocatalysts is a bacteria that hydrolyzes and/or ferments C5 and C6 saccharides. In some embodiments, at least one of the one or more biocatalysts is a hydrolytic enzyme. In some embodiments, the one or more biocatalysts comprise an endoglucanase, an exoglucanase, a cellobiohydrolase, a cellulase, a beta-glucosidase, a glycoside hydrolase, a glycosyltransferase, a lyase, an esterase, a glucamylase, or a combination thereof. In some embodiments, at least one of the one or more biocatalysts is an enzyme that hydrolyzes starch. In some embodiments, at least one of the one or more biocatalysts is an alpha-amylase, glucoamylase, beta-amylase, exo-alpha-1,4-glucanase, or pullulanase. In some embodiments, the one or more biocatalysts comprise at least one fermenting microorganism and at least one hydrolytic enzyme. In some embodiments, the one or more biocatalysts comprise at least one fermenting microorganism that is a yeast or bacteria and at least one enzyme that hydrolyzes starch. In some embodiments, the blended feedstock comprises less than 100 g/L monosaccharides prior to contacting with the one or more biocatalysts. In some embodiments, the blended feedstock comprises from about 1 g/L to about 100 g/L monosaccharides prior to contacting with the one or more biocatalysts. In some embodiments, the first biomass and the one or more cellulosic-derived C6 monosaccharides are combined in a ratio of from about 50:50 to 99:1 (first biomass: cellulosic-derived C6 monosaccharides) by volume or by weight:volume. In some embodiments, the first biomass and the one or more cellulosic-derived C6 monosaccharides are combined in a ratio of about 80:20 (first biomass: cellulosic-derived C6 monosaccharides) by volume or by weight:volume. In some embodiments, the first biomass and the one or more cellulosic-derived C6 monosaccharides are combined in a ratio of about 90:10 (first biomass: cellulosic-derived C6 monosaccharides) by volume or by weight:volume. In some embodiments, the blended feedstock comprises from about 10% to about 50% solids from the first biomass. In some embodiments, the blended feedstock comprises from about 20% to about 40% solids from the first biomass. In some embodiments, the blended feedstock comprises from about 30% to about 36% solids from the first biomass. In some embodiments, the one or more cellulosic-derived C6 monosaccharides are at a concentration of from about 10% to about 70% w/v prior to combining with the first biomass. In some embodiments, the one or more cellulosic-derived C6 monosaccharides are at a concentration of from about 20% to about 50% w/v prior to combining with the first biomass.

Disclosed herein are systems for producing one or more fermentation end-products comprising: (a) combining a fermentor comprising a broth; (b) a blended feedstock comprising a first biomass and one or more cellulosic-derived C6 monosaccharides in the broth; and (c) one or more biocatalysts. In some embodiments, yield of at least one of the one or more fermentation end-products is increased relative to fermentation of the first biomass without the one or more cellulosic-derived C6 monosaccharides. In some embodiments, the yield of the at least one of the one or more fermentation end-products is increased by about 1% to about 100% relative to fermentation of the first biomass without the one or more cellulosic-derived C6 monosaccharides. In some embodiments, at least one of the one or more fermentation end-products is produced at a rate that is faster relative to fermentation of the first biomass without the one or more cellulosic-derived C6 monosaccharides. In some embodiments, at least one of the one or more fermentation end-products is produced at a rate that is about 1% to about 100% faster relative to fermentation of the first biomass without the one or more cellulosic-derived C6 monosaccharides. In some embodiments, the one or more cellulosic-derived C6 monosaccharides are at a concentration that differs from a concentration of saccharides in the first biomass by less than +/−50%, wherein the concentration of saccharides in the first biomass is in monosaccharide equivalents. In some embodiments, the one or more cellulosic-derived C6 monosaccharides are at a concentration that differs from a concentration of saccharides in the first biomass by less than +/−25%, wherein the concentration of saccharides in the first biomass is in monosaccharide equivalents. In some embodiments, the one or more fermentation end-products comprise one or more alcohols. In some embodiments, the one or more fermentation end-products comprise ethanol. In some embodiments, the system further comprises a feeder to add the one or more cellulosic-derived C6 monosaccharides to the broth over time. In some embodiments, the one or more cellulosic-derived C6 monosaccharides are added at a rate of from about 0.01 mL/min/L of broth to about 5 mL/min/L of broth. In some embodiments, a yield of one or more other products is decreased relative to a system that does not contain the feeder. In some embodiments, the yield of the one or more other products is decreased by about 1% to about 100% relative to the non-fed batch fermentation. In some embodiments, the one or more other products comprise one or more polyols or sugar alcohols. In some embodiments, the one or more other products comprise methanol, glycol, glycerol, erythritol, threitol, arabitol, xylitol, ribitol, mannitol, sorbitol, dulcitol, fucitol, iditol, inositol, volemitol, isomalt, maltitol, lactitol, polyglycitol, or a combination thereof. In some embodiments, the one or more other products comprise glycerol. In some embodiments, the first biomass comprises non-cellulosic sugars. In some embodiments, the first biomass comprises non-cellulosic oligosaccharides. In some embodiments, the first biomass comprises starch. In some embodiments, the first biomass comprises corn, corn mash, sugar cane, sugar beets, sugar palms, sweet sorghum, nypa palm, cassava, rice, milo, sorghum, sweet potatoes, wheat, molasses, tubers, roots, stems, whole grains, barley, rye, milo, sago, cassava, tapioca, rice peas, beans, potatoes, beets, fruits, or a combination thereof. In some embodiments, the one or more cellulosic-derived C6 monosaccharides are produced from the pretreatment and/or hydrolysis of cellulose, hemicellulose, or lignocellulose material. In some embodiments, the one or more cellulosic-derived C6 monosaccharides are produced by the pretreatment and/or hydrolysis of a second biomass comprising cellulose, hemicellulose, or lignocellulose. In some embodiments, the second biomass comprises corn, corn syrup, corn stover, corn cobs, molasses, silage, grass, straw, grain hulls, bagasse, distiller's grains, distiller's dried solubles, distiller's dried grains, condensed distiller's solubles, distiller's wet grains, distiller's dried grains with solubles, wood, bark, sawdust, paper, poplars, willows, switchgrass, alfalfa, prairie bluestem, algae, fruit peels, pits, sorghum, sweet sorghum, sugar cane, switch grass, rice, rice straw, rice hulls, wheat, wheat straw, barley, barley straw, bamboo, seeds, seed hulls, oats, oat hulls, food waste, municipal sewage waste, or a combination thereof. In some embodiments, the one or more biocatalysts comprise one or more fermenting microorganisms. In some embodiments, the one or more biocatalysts comprise one or more yeasts and/or one or more bacteria. In some embodiments, the one or more biocatalysts comprise one or more yeasts. In some embodiments, the one or more biocatalysts comprise one or more strains of *Saccharomyces cerevisiae*. In some embodiments, at least one of the one or more biocatalysts is a genetically-modified yeast that ferments C5 and C6 saccharides. In some embodiments, at least one of the one or more biocatalysts is a bacteria that hydrolyzes and/or ferments C5 and C6 saccharides. In some embodiments, at least one of the one or more biocatalysts is a hydrolytic enzyme. In some embodiments, the one or more biocatalysts comprise an endoglucanase, an exoglucanase, a cellobiohydrolase, a cellulase, a beta-glucosidase, a glycoside hydrolase, a glycosyltransferase, a lyase, an esterase, a glucamylase, or a combination thereof. In some embodiments, at least one of the one or more biocatalysts is an enzyme that hydrolyzes starch. In some embodiments, at least one of the one or more biocatalysts is an alpha-amylase, glucoamylase, beta-amylase, exo-alpha-1,4-glucanase, or pullulanase. In some embodiments, the one or more biocatalysts comprise at least one fermenting microorganism and at least one hydrolytic enzyme. In some embodiments, the one or more biocatalysts comprise at least one fermenting microorganism that is a yeast or bacteria and at least one enzyme that hydrolyzes starch. In some embodiments, the blended feedstock comprises less than 100 g/L monosaccharides. In some embodiments, the blended feedstock comprises from about 1 g/L to about 100 g/L monosaccharides. In some embodiments, the first biomass and the one or more cellulosic-derived C6 monosaccharides are in a ratio of from about 50:50 to 99:1 (first biomass: cellulosic-derived C6 monosaccharides) by volume or by weight:volume. In some embodiments, the first biomass and the one or more cellulosic-derived C6 monosaccharides are in a ratio of about 80:20 (first biomass: cellulosic-derived C6 monosaccharides) by volume or by weight:volume. In some embodiments, the first biomass and the one or more cellulosic-derived C6 monosaccharides are in a ratio of about 90:10 (first biomass: cellulosic-derived C6 monosaccharides) by volume or by weight:volume. In some embodiments, the blended feedstock comprises from about 10% to about 50% solids from the first biomass. In some embodiments, the blended feedstock comprises from about 20% to about 40% solids from the first biomass. In some embodiments, the blended feedstock comprises from about 30% to about 36% solids from the first biomass. In some embodiments, the one or more cellulosic-derived C6 monosaccharides are at a concentration of from about 10% to about 70% w/v prior to combining with the first biomass. In some embodiments, the one or more cellulosic-derived C6 monosaccharides are at a concentration of from about 20% to about 50% w/v prior to combining with the first biomass. In some embodiments, the system further comprises a hydrolysis unit for producing the one or more cellulosic-derived monosaccharides from a second biomass. In some embodiments, the system further comprises a filter for separating solids from the one or more cellulosic derived C6 monosaccharides.

Provided herein are methods of producing one or more fermentation end-products comprising: (a) combining a first biomass with one or more monosaccharides to produce a blended feedstock; (b) contacting the blended feedstock with one or more biocatalysts; and (c) fermenting the first biomass and the one or more monosaccharides for sufficient time to produce one or more fermentation end-products from the blended feedstock. In some embodiments, a yield of at least one of the one or more fermentation end-products is increased relative to fermentation of the first biomass without the one or more monosaccharides. In some embodiments, a yield of at least one of the one or more fermentation end-products is increased by about 1% to about 100% relative to fermentation of the first biomass without the one or more monosaccharides. In some embodiments, a rate of production for at least one of the one or more fermentation end-products is increased relative to fermentation of the first biomass without the one or more monosaccharides. In some embodiments, a rate of production for at least one of the one or more fermentation end-products is increased by about 1% to about 100% relative to fermentation of the first biomass without the one or more monosaccharides. In some embodiments, the one or more fermentation end-products comprise one or more alcohols. In some embodiments, the one or more fermentation end-products comprise ethanol. In some embodiments, a yield of one or more other products is decreased relative to fermentation of the one or more monosaccharides without the first biomass. In some embodiments, a yield of one or more other products is decreased by about 1% to about 100% relative to fermentation of the one or more monosaccharides without the first biomass. In some embodiments, the one or more other products comprise one or more polyols or sugar alcohols. In some embodiments, the one or more other products comprise methanol, glycol, glycerol, erythritol, threitol, arabitol, xylitol, ribitol, mannitol, sorbitol, dulcitol, fucitol, iditol, inositol, volemitol, isomalt, maltitol, lactitol, polyglycitol, or a combination thereof. In some embodiments, the one or more other products comprise glycerol In some embodiments, the first biomass comprises non-cellulosic sugars. In some embodiments, the first biomass comprises non-cellulosic oligosaccharides. In some embodiments, the first biomass comprises starch. In some embodiments, the first biomass comprises corn or corn mash, sugar cane, sugar beet, sugar palm, sweet sorghum, nypa palm, cassava, rice, milo, sorghum, sweet potato, wheat, molasses, or a combination thereof. In some embodiments, the one or more monosaccharides are produced from the pretreatment and/or hydrolysis of cellulose, hemicellulose, or lignocellulose material. In some embodiments, the one or more monosaccharides are a C6-enriched hydrolysate produced by the pretreatment and/or hydrolysis of a second biomass comprising cellulose, hemicellulose, or lignocellulose. In some embodiments, the second biomass comprises corn, corn syrup, corn stover, corn cobs, molasses, silage, grass, straw, grain hulls, bagasse, distiller's grains, distiller's dried solubles, distiller's dried grains, condensed distiller's solubles, distiller's wet grains, distiller's dried grains with solubles, wood, bark, sawdust, paper, poplars, willows, switchgrass, alfalfa, prairie bluestem, algae, fruit peels, pits, sorghum, sweet sorghum, sugar cane, switch grass, rice, rice straw, rice hulls, wheat, wheat straw, barley, barley straw, bamboo, seeds, seed hulls, oats, oat hulls, food waste, municipal sewage waste, or a combination thereof. In some embodiments, the one or more monosaccharides are at a concentration that differs from a concentration of sugars in the first biomass by less than about +/−50%, wherein the concentration of sugars in the first biomass assumes complete hydrolysis to monomers. In some embodiments, the one or more monosaccharides are at a concentration that differs from a concentration of sugars in the first biomass by less than about +/−40%, wherein the concentration of sugars in the first biomass assumes complete hydrolysis to monomers. In some embodiments, the one or more monosaccharides are at a concentration that differs from a concentration of sugars in the first biomass by less than about +/−30%, wherein the concentration of sugars in the first biomass assumes complete hydrolysis to monomers. In some embodiments, the one or more monosaccharides are at a concentration that differs from a concentration of sugars in the first biomass by less than about +/−20%, wherein the concentration of sugars in the first biomass assumes complete hydrolysis to monomers. In some embodiments, the one or more monosaccharides are at a concentration that differs from a concentration of sugars in the first biomass by less than about +/−15%, wherein the concentration of sugars in the first biomass assumes complete hydrolysis to monomers. In some embodiments, the one or more monosaccharides are at a concentration that differs from a concentration of sugars in the first biomass by less than about +/−10%, wherein the concentration of sugars in the first biomass assumes complete hydrolysis to monomers. In some embodiments, the one or more monosaccharides comprises less than about 50% C5 sugars. In some embodiments, the one or more monosaccharides comprises less than about 40% C5 sugars. In some embodiments, the one or more monosaccharides comprises less than about 30% C5 sugars. In some embodiments, the one or more monosaccharides comprises less than about 20% C5 sugars. In some embodiments, the one or more monosaccharides comprises less than about 10% C5 sugars. In some embodiments, the one or more monosaccharides comprises from about 0.1% to about 10% C5 sugars. In some embodiments, at least one of the one or more biocatalysts is a fermenting microorganism. In some embodiments, at least one of the one or more biocatalysts is a hydrolytic enzyme. In some embodiments, the one or more biocatalysts comprise at least one fermenting microorganism and at least one hydrolytic enzyme. In some embodiments, the blended feedstock comprises less than about 100 g/L monosaccharides prior to contacting with the one or more biocatalysts. In some embodiments, the blended feedstock comprises from about 1 g/L to about 100 g/L monosaccharides prior to contacting with the one or more biocatalysts. In some embodiments, the first biomass and the one or more sugars are combined in a ratio of from about 50:50 to 99:1 by volume or by weight:volume. In some embodiments, the first biomass and the one or more sugars are combined in a ratio of about 80:20 by volume or by weight:volume. In some embodiments, the first biomass and the one or more sugars are combined in a ratio of about 90:10 by volume or by weight:volume. In some embodiments, the one or more biocatalysts comprise one or more yeast strains, one or more bacterial strains, or a combination thereof. In some embodiments, the one or more biocatalysts comprise *Saccharomyces cerevisiae*. In some embodiments, the one or more biocatalysts comprise an endoglucanase, an exoglucanase, a cellobiohydrolase, a cellulase, a beta-glucosidase, a glycoside hydrolase, a glycosyltransferase, a lyase, an esterase, a glucamylase, or a combination thereof.

Also provided herein are methods of producing one or more fermentation end-products comprising: (a) combining a first biomass with a C6-enriched hydrolysate to produce a blended feedstock; (b) contacting the blended feedstock with one or more hydrolytic enzymes and/or one or more fermenting microorganisms; and (c) fermenting the first biomass and the C6-enriched hydrolysate for a time sufficient to produce one or more fermentation end-products from the blended feedstock. In some embodiments, the C6-enriched hydrolysate comprises monosaccharides produced from the pretreatment and/or hydrolysis of a second biomass. In some embodiments, a yield of at least one of the one or more fermentation end-products is increased relative to fermentation of the first biomass without the C6-enriched hydrolysate. In some embodiments, a yield of at least one of the one or more fermentation end-products is increased by about 1% to about 100% relative to fermentation of the first biomass without the C6-enriched hydrolysate. In some embodiments, a rate of production for at least one of the one or more fermentation end-products is increased relative to fermentation of the first biomass without the C6-enriched hydrolysate. In some embodiments, a rate of production for at least one of the one or more fermentation end-products is increased by about 1% to about 100% relative to fermentation of the first biomass without the C6-enriched hydrolysate. In some embodiments, the one or more fermentation end-products comprise one or more alcohols. In some embodiments, the one or more fermentation end-products comprise ethanol. In some embodiments, a yield of one or more other products is decreased relative to fermentation of the C6-enriched hydrolysate without the first biomass. In some embodiments, a yield of one or more other products is decreased by about 1% to about 100% relative to fermentation of the C6-enriched hydrolysate without the first biomass. In some embodiments, the one or more other products comprise one or more polyols or sugar alcohols. In some embodiments, the one or more other products comprise methanol, glycol, glycerol, erythritol, threitol, arabitol, xylitol, ribitol, mannitol, sorbitol, dulcitol, fucitol, iditol, inositol, volemitol, isomalt, maltitol, lactitol, polyglycitol, or a combination thereof. In some embodiments, the one or more other products comprise glycerol. In some embodiments, the first biomass comprises non-cellulosic sugars. In some embodiments, the first biomass comprises non-cellulosic oligosaccharides. In some embodiments, the first biomass comprises starch. In some embodiments, the first biomass comprises corn or corn mash, sugar cane, sugar beet, sugar palm, sweet sorghum, nypa palm, cassava, rice, milo, sorghum, sweet potato, wheat, molasses, or a combination thereof. In some embodiments, the second biomass comprises cellulose, hemicellulose, or lignocellulose. In some embodiments, the second biomass comprises corn, corn syrup, corn stover, corn cobs, molasses, silage, grass, straw, grain hulls, bagasse, distiller's grains, distiller's dried solubles, distiller's dried grains, condensed distiller's solubles, distiller's wet grains, distiller's dried grains with solubles, wood, bark, sawdust, paper, poplars, willows, switchgrass, alfalfa, prairie bluestem, algae, fruit peels, pits, sorghum, sweet sorghum, sugar cane, switch grass, rice, rice straw, rice hulls, wheat, wheat straw, barley, barley straw, bamboo, seeds, seed hulls, oats, oat hulls, food waste, municipal sewage waste, or a combination thereof. In some embodiments, the C6-enriched hydrolysate comprises monosaccharides at a concentration that differs from a concentration of sugars in the first biomass by less than about +/−50%, wherein the concentration of sugars in the first biomass assumes complete hydrolysis to monomers. In some embodiments, the C6-enriched hydrolysate comprises monosaccharides at a concentration that differs from a concentration of sugars in the first biomass by less than about +/−40%, wherein the concentration of sugars in the first biomass assumes complete hydrolysis to monomers. In some embodiments, the C6-enriched hydrolysate comprises monosaccharides at a concentration that differs from a concentration of sugars in the first biomass by less than about +/−30%, wherein the concentration of sugars in the first biomass assumes complete hydrolysis to monomers. In some embodiments, the C6-enriched hydrolysate comprises monosaccharides at a concentration that differs from a concentration of sugars in the first biomass by less than about +/−20%, wherein the concentration of sugars in the first biomass assumes complete hydrolysis to monomers. In some embodiments, the C6-enriched hydrolysate comprises monosaccharides at a concentration that differs from a concentration of sugars in the first biomass by less than about +/−15%, wherein the concentration of sugars in the first biomass assumes complete hydrolysis to monomers. In some embodiments, the C6-enriched hydrolysate comprises monosaccharides at a concentration that differs from a concentration of sugars in the first biomass by less than about +/−10%, wherein the concentration of sugars in the first biomass assumes complete hydrolysis to monomers. In some embodiments, the C6-enriched hydrolysate comprises less than about 50% C5 sugars. In some embodiments, the C6-enriched hydrolysate comprises less than about 40% C5 sugars. In some embodiments, the C6-enriched hydrolysate comprises less than about 30% C5 sugars. In some embodiments, the C6-enriched hydrolysate comprises less than about 20% C5 sugars. In some embodiments, the C6-enriched hydrolysate comprises less than about 10% C5 sugars. In some embodiments, the C6-enriched hydrolysate comprises from about 0.1% to about 10% C5 sugars. In some embodiments, the one or more fermenting microorganisms comprise one or more yeast strains, one or more bacterial strains, or a combination thereof. In some embodiments, at least one of the one or more fermenting microorganisms is *Saccharomyces cerevisiae*. In some embodiments, the one or more hydrolytic enzymes comprise an endoglucanase, an exoglucanase, a cellobiohydrolase, a cellulase, a beta-glucosidase, a glycoside hydrolase, a glycosyltransferase, a lyase, an esterase, a glucamylase, or a combination thereof. In some embodiments, the blended feedstock comprises less than about 100 g/L monosaccharides prior to contacting with the one or more fermenting microorganisms and the one or more hydrolytic enzymes. In some embodiments, the blended feedstock comprises from about 1 g/L to about 100 g/L monosaccharides prior to contacting with the one or more fermenting microorganisms and the one or more hydrolytic enzymes. In some embodiments, the first biomass and the C6-enriched hydrolysate are combined in a ratio of from about 50:50 to 99:1 by volume or by weight:volume. In some embodiments, the first biomass and the C6-enriched hydrolysate are combined in a ratio of about 80:20 by volume or by weight:volume. In some embodiments, the first biomass and the C6-enriched hydrolysate are combined in a ratio of about 90:10 by volume or by weight:volume.

In another aspect, provided herein are methods of producing a C6-enriched hydrolysate comprising: (a) treating a biomass comprising cellulose and hemicellulose and/or lignin to solubilize the hemicellulose and/or lignin; (b) separating the solubilized hemicellulose and/or lignin from the cellulose; and (c) hydrolyzing the cellulose, thereby producing the C6-enriched hydrolysate. In some embodiments, the biomass comprising cellulose and hemicellulose and/or lignin comprises corn, corn syrup, corn stover, corn cobs, molasses, silage, grass, straw, grain hulls, bagasse, distiller's grains, distiller's dried solubles, distiller's dried grains, condensed distiller's solubles, distiller's wet grains, distiller's dried grains with solubles, wood, bark, sawdust, paper, poplars, willows, switchgrass, alfalfa, prairie bluestem, algae, fruit peels, pits, sorghum, sweet sorghum, sugar cane, switch grass, rice, rice straw, rice hulls, wheat, wheat straw, barley, barley straw, bamboo, seeds, seed hulls, oats, oat hulls, food waste, municipal sewage waste, or a combination thereof. In some embodiments, the biomass comprises corn stover. In some embodiments, the treating comprises stream treatment, hot water treatment, dilute acid treatment, dilute base treatment, steam explosion, acid-catalyzed steam explosion, or a combination thereof. In some embodiments, the treatment comprises steam treatment. In some embodiments, the treating is performed at a temperature of from about 175 to about 250° C. In some embodiments, the treating is performed at a temperature of about 205° C. In some embodiments, the treating is performed from about 1 minute to about 30 minutes. In some embodiments, the treating is performed for about 7.5 minutes. In some embodiments, the separating is performed using a filter press. In some embodiments, the separating step comprises washing the biomass with water. In some embodiments, the water is from about 25 to about 100° C. In some embodiments, the water is about 50° C. In some embodiments, the water is added in an amount from about 1 to about 5 L/kg of biomass (dry weight). In some embodiments, the water is added in an amount of about 3 L/kg of biomass (dry weight). In some embodiments, the hydrolyzing step comprises enzymatic hydrolysis with one or more enzymes. In some embodiments, the hydrolyzing step is performed at a pH of from about 3 to about 7. In some embodiments, the hydrolyzing step is performed at a pH of about 5. In some embodiments, the hydrolyzing step is performed in a slurry of from about 1% to about 20% wt/wt biomass/water. In some embodiments, the hydrolyzing step is performed in a slurry of about 8% wt/wt biomass/water. In some embodiments, the hydrolyzing step is performed in a jacketed reactor. Some embodiments further comprise concentrating the C6-enriched hydrolysate. In some embodiments, the C6-enriched hydrolysate is concentrated by evaporation. In some embodiments, the C6-enriched hydrolysate is concentrated using a roto-evaporator. In some embodiments, the C6-enriched hydrolysate is concentrated to a C6 sugar concentration of from about 100 g/L to about 500 g/L. In some embodiments, the C6-enriched hydrolysate is concentrated to a C6 sugar concentration of about 300 g/L. In some embodiments, the C6-enriched hydrolysate comprises less than about 50% C5 sugars. In some embodiments, the C6-enriched hydrolysate comprises less than about 40% C5 sugars. In some embodiments, the C6-enriched hydrolysate comprises less than about 30% C5 sugars. In some embodiments, the C6-enriched hydrolysate comprises less than about 20% C5 sugars. In some embodiments, the C6-enriched hydrolysate comprises less than about 10% C5 sugars. In some embodiments, the C6-enriched hydrolysate comprises from about 0.1% to about 10% C5 sugars.

Also provided are C6-enriched hydrolysates produced by any of the methods disclosed herein.

Provided herein are methods of producing ethanol comprising: (a) combining a first biomass comprising starch with a C6-enriched hydrolysate to produce a blended feedstock, (i) wherein the C6-enriched hydrolysate comprises monosaccharides produced from the pretreatment and/or hydrolysis of a second biomass, (ii) wherein the C6-enriched hydrolysate comprises monosaccharides at a concentration that differs from a concentration of sugars in the first biomass by less than about +/−20%, wherein the concentration of sugars in the first biomass assumes complete hydrolysis to monomers, and (iii) wherein the blended feedstock comprises from about 1 g/L to about 100 g/L monosaccharides; (b) contacting the blended feedstock with one or more fermenting microorganisms and one or more hydrolytic enzymes; and (c) fermenting the first biomass and the C6-enriched hydrolysate to produce ethanol from the blended feedstock, wherein an increase rate of production and/or yield of the ethanol is achieved relative to the hydrolysis and fermentation of the first biomass without the C6-enriched hydrolysate. Also provided are methods of producing ethanol comprising: (a) combining a first biomass comprising starch with a C6-enriched hydrolysate to produce a blended feedstock, (i) wherein the C6-enriched hydrolysate comprises monosaccharides produced from the pretreatment and/or hydrolysis of a second biomass, (ii) wherein the C6-enriched hydrolysate comprises monosaccharides at a concentration that differs from a concentration of sugars in the first biomass by less than about +/−20%, wherein the concentration of sugars in the first biomass assumes complete hydrolysis to monomers, and (iii) wherein the blended feedstock comprises from about 1 g/L to about 100 g/L monosaccharides; (b) contacting the blended feedstock with one or more fermenting microorganisms and one or more hydrolytic enzymes; and (c) fermenting the first biomass and the C6-enriched hydrolysate to produce ethanol from the blended feedstock, wherein a yield of one or more polyols or sugar alcohols is decreased relative to fermentation of the C6-enriched hydrolysate alone.

Ethanol produced by any of the methods disclosed herein is also provided.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
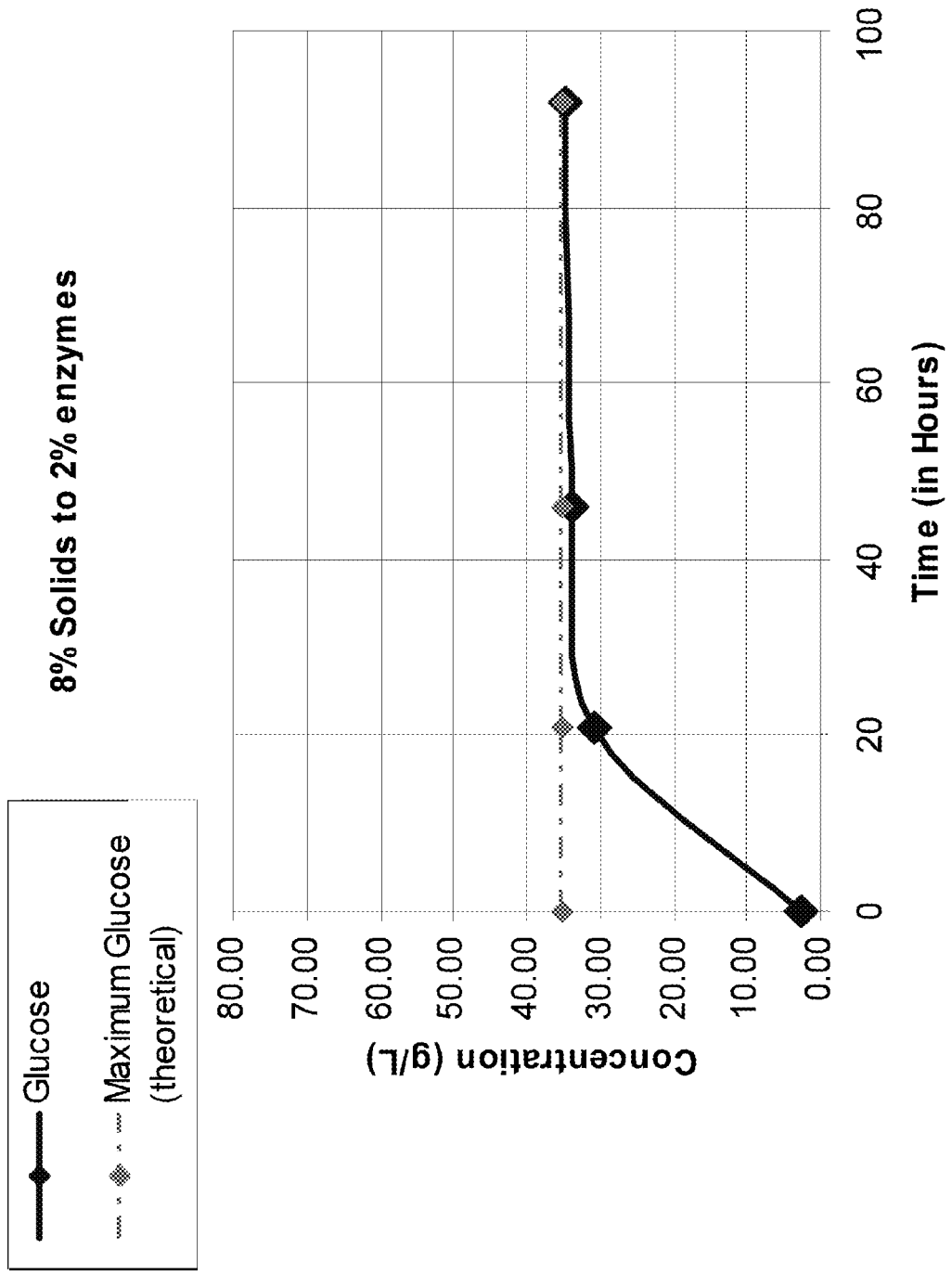
FIG. 1 is a graph illustrating the trajectory of how biomass is converted from solids into liquefied C6 sugars during hydrolysis using cellulase enzymes.

As used in the specification and the appended claims, the singular forms "a," "an" and "the" include plural referents unless the context clearly dictates otherwise. Thus, for example, reference to "a purified monomer" includes mixtures of two or more purified monomers. The term "comprising" as used herein is synonymous with "including," "containing," or "characterized by," and is inclusive or open-ended and does not exclude additional, unrecited elements or method steps.

"About" means a referenced numeric indication plus or minus 10% of that referenced numeric indication. For example, the term about 4 would include a range of 3.6 to 4.4. All numbers expressing quantities of ingredients, reaction conditions, and so forth used in the specification are to be understood as being modified in all instances by the term "about." Accordingly, unless indicated to the contrary, the numerical parameters set forth herein are approximations that can vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Wherever the phrase "for example," "such as," "including" and the like are used herein, the phrase "and without limitation" is understood to follow unless explicitly stated otherwise. Therefore, "for example ethanol production" means "for example and without limitation ethanol production."

In this specification and in the claims that follow, reference will be made to a number of terms which shall be defined to have the following meanings.

Definitions

"Optional" or "optionally" means that the subsequently described event or circumstance may or may not occur, and that the description includes instances where said event or circumstance occurs and instances where it does not. For example, the phrase "the medium can optionally contain glucose" means that the medium may or may not contain glucose as an ingredient and that the description includes both media containing glucose and media not containing glucose.

Unless characterized otherwise, technical and scientific terms used herein have the same meaning as commonly understood by one of ordinary skill in the art.

"Fermentive end-product" and "fermentation end-product" are used interchangeably herein to include biofuels, chemicals, compounds suitable as liquid fuels, gaseous fuels, triacylglycerols (TAGs), reagents, chemical feedstocks, chemical additives, processing aids, food additives, bioplastiks and precursors to bioplastiks, and other products. Examples of fermentive end-products include but are not limited to 1,4 diacids (succinic, fumaric and malic), 2,5 furan dicarboxylic acid, 3 hydroxy propionic acid, aspartic acid, glucaric acid, glutamic acid, itaconic acid, levulinic acid, 3-hydroxybutyrolactone, glycerol, sorbitol, xylitol/arabinitol, butanediol, butanol, methane, methanol, ethane, ethene, ethanol, n-propane, 1-propene, 1-propanol, propanal, acetone, propionate, n-butane, 1-butene, 1-butanol, butanal, butanoate, isobutanal, isobutanol, 2-methylbutanal, 2-methylbutanol, 3-methylbutanal, 3-methylbutanol, 2-butene, 2-butanol, 2-butanone, 2,3-butanediol, 3-hydroxy-2-butanone, 2,3-butanedione, ethylbenzene, ethenylbenzene, 2-phenylethanol, phenylacetaldehyde, 1-phenylbutane, 4-phenyl-1-butene, 4-phenyl-2-butene, 1-phenyl-2-butene, 1-phenyl-2-butanol, 4-phenyl-2-butanol, 1-phenyl-2-butanone, 4-phenyl-2-butanone, 1-phenyl-2,3-butandiol, 1-phenyl-3-hydroxy-2-butanone, 4-phenyl-3-hydroxy-2-butanone, 1-phenyl-2,3-butanedione, n-pentane, ethylphenol, ethenylphenol, 2-(4-hydroxyphenyl)ethanol, 4-hydroxyphenylacetaldehyde, 1-(4-hydroxyphenyl)butane, 4-(4-hydroxyphenyl)-1-butene, 4-(4-hydroxyphenyl)-2-butene, 1-(4-hydroxyphenyl)-1-butene, 1-(4-hydroxyphenyl)-2-butanol, 4-(4-hydroxyphenyl)-2-butanol, 1-(4-hydroxyphenyl)-2-butanone, 4-(4-hydroxyphenyl)-2-butanone, 1-(4-hydroxyphenyl)-2,3-butandiol, 1-(4-hydroxyphenyl)-3-hydroxy-2-butanone, 4-(4-hydroxyphenyl)-3-hydroxy-2-butanone, 1-(4-hydroxyphenyl)-2,3-butanonedione, indolylethane, indolylethene, 2-(indole-3-)ethanol, n-pentane, 1-pentene, 1-pentanol, pentanal, pentanoate, 2-pentene, 2-pentanol, 3-pentanol, 2-pentanone, 3-pentanone, 4-methylpentanal, 4-methylpentanol, 2,3-pentanediol, 2-hydroxy-3-pentanone, 3-hydroxy-2-pentanone, 2,3-pentanedione, 2-methylpentane, 4-methyl-1-pentene, 4-methyl-2-pentene, 4-methyl-3-pentene, 4-methyl-2-pentanol, 2-methyl-3-pentanol, 4-methyl-2-pentanone, 2-methyl-3-pentanone, 4-methyl-2,3-pentanediol, 4-methyl-2-hydroxy-3-pentanone, 4-methyl-3-hydroxy-2-pentanone, 4-methyl-2,3-pentanedione, 1-phenylpentane, 1-phenyl-1-pentene, 1-phenyl-2-pentene, 1-phenyl-3-pentene, 1-phenyl-2-pentanol, 1-phenyl-3-pentanol, 1-phenyl-2-pentanone, 1-phenyl-3-pentanone, 1-phenyl-2,3-pentanediol, 1-phenyl-2-hydroxy-3-pentanone, 1-phenyl-3-hydroxy-2-pentanone, 1-phenyl-2,3-pentanedione, 4-methyl-1-phenylpentane, 4-methyl-1-phenyl-1-pentene, 4-methyl-1-phenyl-2-pentene, 4-methyl-1-phenyl-3-pentene, 4-methyl-1-phenyl-3-pentanol, 4-methyl-1-phenyl-2-pentanol, 4-methyl-1-phenyl-3-pentanone, 4-methyl-1-phenyl-2-pentanone, 4-methyl-1-phenyl-2,3-pentanediol, 4-methyl-1-phenyl-2,3-pentanedione, 4-methyl-1-phenyl-3-hydroxy-2-pentanone, 4-methyl-1-phenyl-2-hydroxy-3-pentanone, 1-(4-hydroxyphenyl)pentane, 1-(4-hydroxyphenyl)-1-pentene, 1-(4-hydroxyphenyl)-2-pentene, 1-(4-hydroxyphenyl)-3-pentene, 1-(4-hydroxyphenyl)-2-pentanol, 1-(4-hydroxyphenyl)-3-pentanol, 1-(4-hydroxyphenyl)-2-pentanone, 1-(4-hydroxyphenyl)-3-pentanone, 1-(4-hydroxyphenyl)-2,3-pentanediol, 1-(4-hydroxyphenyl)-2-hydroxy-3-pentanone, 1-(4-hydroxyphenyl)-3-hydroxy-2-pentanone, 1-(4-hydroxyphenyl)-2,3-pentanedione, 4-methyl-1-(4-hydroxyphenyl)pentane, 4-methyl-1-(4-hydroxyphenyl)-2-pentene, 4-methyl-1-(4-hydroxyphenyl)-3-pentene, 4-methyl-1-(4-hydroxyphenyl)-1-pentene, 4-methyl-1-(4-hydroxyphenyl)-3-pentanol, 4-methyl-1-(4-hydroxyphenyl)-2-pentanol, 4-methyl-1-(4-hydroxyphenyl)-3-pentanone, 4-methyl-1-(4-hydroxyphenyl)-2-pentanone, 4-methyl-1-(4-hydroxyphenyl)-2,3-pentanediol, 4-methyl-1-(4-hydroxyphenyl)-2,3-pentanedione, 4-methyl-1-(4-hydroxyphenyl)-3-hydroxy-2-pentanone, 4-methyl-1-(4-hydroxyphenyl)-2-hydroxy-3-pentanone, 1-indole-3-pentane, 1-(indole-3)-1-pentene, 1-(indole-3)-2-pentene, 1-(indole-3)-3-pentene, 1-(indole-3)-2-pentanol, 1-(indole-3)-3-pentanol, 1-(indole-3)-2-pentanone, 1-(indole-3)-3-pentanone, 1-(indole-3)-2,3-pentanediol, 1-(indole-3)-2-hydroxy-3-pentanone, 1-(indole-3)-3-hydroxy-2-pentanone, 1-(indole-3)-2,3-pentandione, 4-methyl-1-(indole-3-)pentane, 4-methyl-1-(indole-3)-2-pentene, 4-methyl-1-(indole-3)-3-pentene, 4-methyl-1-(indole-3)-1-pentene, 4-methyl-2-(indole-3)-3-pentanol, 4-methyl-1-(indole-3)-2-pentanol, 4-methyl-1-(indole-3)-3-pentanone, 4-methyl-1-(indole-3)-2-pentanone, 4-methyl-1-(indole-3)-2,3-pentanediol, 4-methyl-1-(indole-3)-2,3-pentanedione, 4-methyl-1-(indole-3)-3-hydroxy-2-pentanone, 4-methyl-1-(indole-3)-2-hydroxy-3-pentanone, n-hexane, 1-hexene, 1-hexanol, hexanal, hexanoate, 2-hexene, 3-hexene, 2-hexanol, 3-hexanol, 2-hexanone, 3-hexanone, 2,3-hexanediol, 2,3-hexanedione, 3,4-hexanediol, 3,4-hexanedione, 2-hydroxy-3-hexanone, 3-hydroxy-2-hexanone, 3-hydroxy-4-hexanone, 4-hydroxy-3-hexanone, 2-methylhexane, 3-methylhexane, 2-methyl-2-hexene, 2-methyl-3-hexene, 5-methyl-1-hexene, 5-methyl-2-hexene, 4-methyl-1-hexene, 4-methyl-2-hexene, 3-methyl-3-hexene, 3-methyl-2-hexene, 3-methyl-1-hexene, 2-methyl-3-hexanol, 5-methyl-2-hexanol, 5-methyl-3-hexanol, 2-methyl-3-hexanone, 5-methyl-2-hexanone, 5-methyl-3-hexanone, 2-methyl-3,4-hexanediol, 2-methyl-3,4-hexanedione, 5-methyl-2,3-hexanediol, 5-methyl-2,3-hexanedione, 4-methyl-2,3-hexanediol, 4-methyl-2,3-hexanedione, 2-methyl-3-hydroxy-4-hexanone, 2-methyl-4-hydroxy-3-hexanone, 5-methyl-2-hydroxy-3-hexanone, 5-methyl-3-hydroxy-2-hexanone, 4-methyl-2-hydroxy-3-hexanone, 4-methyl-3-hydroxy-2-hexanone, 2,5-dimethylhexane, 2,5-dimethyl-2-hexene, 2,5-dimethyl-3-hexene, 2,5-dimethyl-3-hexanol, 2,5-dimethyl-3-hexanone, 2,5-dimethyl-3,4-hexanediol, 2,5-dimethyl-3,4-hexanedione, 2,5-dimethyl-3-hydroxy-4-hexanone, 5-methyl-1-phenylhexane, 4-methyl-1-phenylhexane, 5-methyl-1-phenyl-1-hexene, 5-methyl-1-phenyl-2-hexene, 5-methyl-1-phenyl-3-hexene, 4-methyl-1-phenyl-1-hexene, 4-methyl-1-phenyl-2-hexene, 4-methyl-1-phenyl-3-hexene, 5-methyl-1-phenyl-2-hexanol, 5-methyl-1-phenyl-3-hexanol, 4-methyl-1-phenyl-2-hexanol, 4-methyl-1-phenyl-3-hexanol, 5-methyl-1-phenyl-2-hexanone, 5-methyl-1-phenyl-3-hexanone, 4-methyl-1-phenyl-2-hexanone, 4-methyl-1-phenyl-3-hexanone, 5-methyl-1-phenyl-2,3-hexanediol, 4-methyl-1-phenyl-2,3-hexanediol, 5-methyl-1-phenyl-3-hydroxy-2-hexanone, 5-methyl-1-phenyl-2-hydroxy-3-hexanone, 4-methyl-1-phenyl-3-hydroxy-2-hexanone, 4-methyl-1-phenyl-2-hydroxy-3-hexanone, 5-methyl-1-phenyl-2,3-hexanedione, 4-methyl-1-phenyl-2,3-hexanedione, 4-methyl-1-(4-hydroxyphenyl)hexane, 5-methyl-1-(4-hydroxyphenyl)-1-hexene, 5-methyl-1-(4-hydroxyphenyl)-2-hexene, 5-methyl-1-(4-hydroxyphenyl)-3-hexene, 4-methyl-1-(4-hydroxyphenyl)-1-hexene, 4-methyl-1-(4-hydroxyphenyl)-2-hexene, 4-methyl-1-(4-hydroxyphenyl)-3-hexene, 5-methyl-1-(4-hydroxyphenyl)-2-hexanol, 5-methyl-1-(4-hydroxyphenyl)-3-hexanol, 4-methyl-1-(4-hydroxyphenyl)-2-hexanol, 4-methyl-1-(4-hydroxyphenyl)-3-hexanol, 5-methyl-1-(4-hydroxyphenyl)-2-hexanone, 5-methyl-1-(4-hydroxyphenyl)-3-hexanone, 4-methyl-1-(4-hydroxyphenyl)-2-hexanone, 4-methyl-1-(4-hydroxyphenyl)-3-hexanone, 5-methyl-1-(4-hydroxyphenyl)-2,3-hexanediol, 4-methyl-1-(4-hydroxyphenyl)-2,3-hexanediol, 5-methyl-1-(4-hydroxyphenyl)-3-hydroxy-2-hexanone, 5-methyl-1-(4-hydroxyphenyl)-2-hydroxy-3-hexanone, 4-methyl-1-(4-hydroxyphenyl)-3-hydroxy-2-hexanone, 4-methyl-1-(4-hydroxyphenyl)-2-hydroxy-3-hexanone, 5-methyl-1-(4-hydroxyphenyl)-2,3-hexanedione, 4-methyl-1-(4-hydroxyphenyl)-2,3-hexanedione, 4-methyl-1-(indole-3-)hexane, 5-methyl-1-(indole-3)-1-hexene, 5-methyl-1-(indole-3)-2-hexene, 5-methyl-1-(indole-3)-3-hexene, 4-methyl-1-(indole-3)-1-hexene, 4-methyl-1-(indole-3)-2-hexene, 4-methyl-1-(indole-3)-3-hexene, 5-methyl-1-(indole-3)-2-hexanol, 5-methyl-1-(indole-3)-3-hexanol, 4-methyl-1-(indole-3)-2-hexanol, 4-methyl-1-(indole-3)-3-hexanol, 5-methyl-1-(indole-3)-2-hexanone, 5-methyl-1-(indole-3)-3-hexanone, 4-methyl-1-(indole-3)-2-hexanone, 4-methyl-1-(indole-3)-3-hexanone, 5-methyl-1-(indole-3)-

2,3-hexanediol, 4-methyl-1-(indole-3)-2,3-hexanediol, 5-methyl-1-(indole-3)-3-hydroxy-2-hexanone, 5-methyl-1-(indole-3)-2-hydroxy-3-hexanone, 4-methyl-1-(indole-3)-3-hydroxy-2-hexanone, 4-methyl-1-(indole-3)-2-hydroxy-3-hexanone, 5-methyl-1-(indole-3)-2,3-hexanedione, 4-methyl-1-(indole-3)-2,3-hexanedione, n-heptane, 1-heptene, 1-heptanol, heptanal, heptanoate, 2-heptene, 3-heptene, 2-heptanol, 3-heptanol, 4-heptanol, 2-heptanone, 3-heptanone, 4-heptanone, 2,3-heptanediol, 2,3-heptanedione, 3,4-heptanediol, 3,4-heptanedione, 2-hydroxy-3-heptanone, 3-hydroxy-2-heptanone, 3-hydroxy-4-heptanone, 4-hydroxy-3-heptanone, 2-methylheptane, 3-methylheptane, 6-methyl-2-heptene, 6-methyl-3-heptene, 2-methyl-3-heptene, 2-methyl-2-heptene, 5-methyl-2-heptene, 5-methyl-3-heptene, 3-methyl-3-heptene, 2-methyl-3-heptanol, 2-methyl-4-heptanol, 6-methyl-3-heptanol, 5-methyl-3-heptanol, 3-methyl-4-heptanol, 2-methyl-3-heptanone, 2-methyl-4-heptanone, 6-methyl-3-heptanone, 5-methyl-3-heptanone, 3-methyl-4-heptanone, 2-methyl-3,4-heptanediol, 2-methyl-3,4-heptanedione, 6-methyl-3,4-heptanediol, 6-methyl-3,4-heptanedione, 5-methyl-3,4-heptanediol, 5-methyl-3,4-heptanedione, 2-methyl-3-hydroxy-4-heptanone, 2-methyl-4-hydroxy-3-heptanone, 6-methyl-3-hydroxy-4-heptanone, 6-methyl-4-hydroxy-3-heptanone, 5-methyl-3-hydroxy-4-heptanone, 5-methyl-4-hydroxy-3-heptanone, 2,6-dimethyl-heptane, 2,5-dimethylheptane, 2,6-dimethyl-2-heptene, 2,6-dimethyl-3-heptene, 2,5-dimethyl-2-heptene, 2,5-dimethyl-3-heptene, 3,6-dimethyl-3-heptene, 2,6-dimethyl-3-heptanol, 2,6-dimethyl-4-heptanol, 2,5-dimethyl-3-heptanol, 2,5-dimethyl-4-heptanol, 2,6-dimethyl-3,4-heptanediol, 2,6-dimethyl-3,4-heptanedione, 2,5-dimethyl-3,4-heptanediol, 2,5-dimethyl-3,4-heptanedione, 2,6-dimethyl-3-hydroxy-4-heptanone, 2,6-dimethyl-4-hydroxy-3-heptanone, 2,5-dimethyl-3-hydroxy-4-heptanone, 2,5-dimethyl-4-hydroxy-3-heptanone, n-octane, 1-octene, 2-octene, 1-octanol, octanal, octanoate, 3-octene, 4-octene, 4-octanol, 4-octanone, 4,5-octanediol, 4,5-octanedione, 4-hydroxy-5-octanone, 2-methyloctane, 2-methyl-3-octene, 2-methyl-4-octene, 7-methyl-3-octene, 3-methyl-3-octene, 3-methyl-4-octene, 6-methyl-3-octene, 2-methyl-4-octanol, 7-methyl-4-octanol, 3-methyl-4-octanol, 6-methyl-4-octanol, 2-methyl-4-octanone, 7-methyl-4-octanone, 3-methyl-4-octanone, 6-methyl-4-octanone, 2-methyl-4,5-octanediol, 2-methyl-4,5-octanedione, 3-methyl-4,5-octanediol, 3-methyl-4,5-octanedione, 2-methyl-4-hydroxy-5-octanone, 2-methyl-5-hydroxy-4-octanone, 3-methyl-4-hydroxy-5-octanone, 3-methyl-5-hydroxy-4-octanone, 2,7-dimethyloctane, 2,7-dimethyl-3-octene, 2,7-dimethyl-4-octene, 2,7-dimethyl-4-octanol, 2,7-dimethyl-4-octanone, 2,7-dimethyl-4,5-octanediol, 2,7-dimethyl-4,5-octanedione, 2,7-dimethyl-4-hydroxy-5-octanone, 2,6-dimethyloctane, 2,6-dimethyl-3-octene, 2,6-dimethyl-4-octene, 3,7-dimethyl-3-octene, 2,6-dimethyl-4-octanol, 3,7-dimethyl-4-octanol, 2,6-dimethyl-4-octanone, 3,7-dimethyl-4-octanone, 2,6-dimethyl-4,5-octanediol, 2,6-dimethyl-4,5-octanedione, 2,6-dimethyl-4-hydroxy-5-octanone, 2,6-dimethyl-5-hydroxy-4-octanone, 3,6-dimethyloctane, 3,6-dimethyl-3-octene, 3,6-dimethyl-4-octene, 3,6-dimethyl-4-octanol, 3,6-dimethyl-4-octanone, 3,6-dimethyl-4,5-octanediol, 3,6-dimethyl-4,5-octanedione, 3,6-dimethyl-4-hydroxy-5-octanone, n-nonane, 1-nonene, 1-nonanol, nonanal, nonanoate, 2-methylnonane, 2-methyl-4-nonene, 2-methyl-5-nonene, 8-methyl-4-nonene, 2-methyl-5-nonanol, 8-methyl-4-nonanol, 2-methyl-5-nonanone, 8-methyl-4-nonanone, 8-methyl-4,5-nonanediol, 8-methyl-4,5-nonanedione, 8-methyl-4-hydroxy-5-nonanone, 8-methyl-5-hydroxy-4-nonanone, 2,8-dimethylnonane, 2,8-dimethyl-3-nonene, 2,8-dimethyl-4-nonene, 2,8-dimethyl-5-nonene, 2,8-dimethyl-4-nonanol, 2,8-dimethyl-5-nonanol, 2,8-dimethyl-4-nonanone, 2,8-dimethyl-5-nonanone, 2,8-dimethyl-4,5-nonanediol, 2,8-dimethyl-4,5-nonanedione, 2,8-dimethyl-4-hydroxy-5-nonanone, 2,8-dimethyl-5-hydroxy-4-nonanone, 2,7-dimethylnonane, 3,8-dimethyl-3-nonene, 3,8-dimethyl-4-nonene, 3,8-dimethyl-5-nonene, 3,8-dimethyl-4-nonanol, 3,8-dimethyl-5-nonanol, 3,8-dimethyl-4-nonanone, 3,8-dimethyl-5-nonanone, 3,8-dimethyl-4,5-nonanediol, 3,8-dimethyl-4,5-nonanedione, 3,8-dimethyl-4-hydroxy-5-nonanone, 3,8-dimethyl-5-hydroxy-4-nonanone, n-decane, 1-decene, 1-decanol, decanoate, 2,9-dimethyldecane, 2,9-dimethyl-3-decene, 2,9-dimethyl-4-decene, 2,9-dimethyl-5-decanol, 2,9-dimethyl-5-decanone, 2,9-dimethyl-5,6-decanediol, 2,9-dimethyl-6-hydroxy-5-decanone, 2,9-dimethyl-5,6-decanedionen-undecane, 1-undecene, 1-undecanol, undecanal. undecanoate, n-dodecane, 1-dodecene, 1-dodecanol, dodecanal, dodecanoate, n-dodecane, 1-decadecene, n-tridecane, 1-tridecene, 1-tridecanol, tridecanal, tridecanoate, n-tetradecane, 1-tetradecene, 1-tetradecanol, tetradecanal, tetradecanoate, n-pentadecane, 1-pentadecene, 1-pentadecanol, pentadecanal, pentadecanoate, n-hexadecane, 1-hexadecene, 1-hexadecanol, hexadecanal, hexadecanoate, n-heptadecane, 1-heptadecene, 1-heptadecanol, heptadecanal, heptadecanoate, n-octadecane, 1-octadecene, 1-octadecanol, octadecanal, octadecanoate, n-nonadecane, 1-nonadecene, 1-nonadecanol, nonadecanal, nonadecanoate, eicosane, 1-eicosene, 1-eicosanol, eicosanal, eicosanoate, 3-hydroxy propanal, 1,3-propanediol, 4-hydroxybutanal, 1,4-butanediol, 3-hydroxy-2-butanone, 2,3-butandiol, 1,5-pentane diol, homocitrate, homoisocitorate, b-hydroxy adipate, glutarate, glutarsemialdehyde, glutaraldehyde, 2-hydroxy-1-cyclopentanone, 1,2-cyclopentanediol, cyclopentanone, cyclopentanol, (S)-2-acetolactate, (R)-2,3-Dihydroxy-isovalerate, 2-oxoisovalerate, isobutyryl-CoA, isobutyrate, isobutyraldehyde, 5-amino pentaldehyde, 1,10-diaminodecane, 1,10-diamino-5-decene, 1,10-diamino-5-hydroxydecane, 1,10-diamino-5-decanone, 1,10-diamino-5,6-decanediol, 1,10-diamino-6-hydroxy-5-decanone, phenylacetoaldehyde, 1,4-diphenylbutane, 1,4-diphenyl-1-butene, 1,4-diphenyl-2-butene, 1,4-diphenyl-2-butanol, 1,4-diphenyl-2-butanone, 1,4-diphenyl-2,3-butanediol, 1,4-diphenyl-3-hydroxy-2-butanone, 1-(4-hydeoxyphenyl)-4-phenylbutane, 1-(4-hydeoxyphenyl)-4-phenyl-1-butene, 1-(4-hydeoxyphenyl)-4-phenyl-2-butene, 1-(4-hydeoxyphenyl)-4-phenyl-2-butanol, 1-(4-hydeoxyphenyl)-4-phenyl-2-butanone, 1-(4-hydeoxyphenyl)-4-phenyl-2,3-butanediol, 1-(4-hydeoxyphenyl)-4-phenyl-3-hydroxy-2-butanone, 1-(indole-3)-4-phenylbutane, 1-(indole-3)-4-phenyl-1-butene, 1-(indole-3)-4-phenyl-2-butene, 1-(indole-3)-4-phenyl-2-butanol, 1-(indole-3)-4-phenyl-2-butanone, 1-(indole-3)-4-phenyl-2,3-butanediol, 1-(indole-3)-4-phenyl-3-hydroxy-2-butanone, 4-hydroxyphenylacetoaldehyde, 1,4-di(4-hydroxyphenyl)butane, 1,4-di(4-hydroxyphenyl)-1-butene, 1,4-di(4-hydroxyphenyl)-2-butene, 1,4-di(4-hydroxyphenyl)-2-butanol, 1,4-di(4-hydroxyphenyl)-2-butanone, 1,4-di(4-hydroxyphenyl)-2,3-butanediol, 1,4-di(4-hydroxyphenyl)-3-hydroxy-2-butanone, 1-(4-hydroxyphenyl)-4-(indole-3-)butane, 1-(4-hydroxyphenyl)-4-(indole-3)-1-butene, 1-di(4-hydroxyphenyl)-4-(indole-3)-2-butene, 1-(4-hydroxyphenyl)-4-(indole-3)-2-butanol, 1-(4-hydroxyphenyl)-4-(indole-3)-2-butanone, 1-(4-hydroxyphenyl)-4-(indole-3)-2,3-butanediol, 1-(4-hydroxyphenyl)-4-(indole-3)-3-hydroxy-2-butanone, indole-3-acetoaldehyde, 1,4-di(indole-3-)butane, 1,4-di(indole-3)-1-butene, 1,4-di(indole-3)-2-butene, 1,4-di(indole-3)-2-butanol, 1,4-di(indole-3)-2-butanone, 1,4-di(indole-3)-2,3- butanediol, 1,4-di(indole-3)-3-hydroxy-2-butanone, succinate semialdehyde, hexane-1,8-dicarboxylic acid, 3-hexene-1,8-dicarboxylic acid, 3-hydroxy-hexane-1,8-dicarboxylic acid, 3-hexanone-1,8-dicarboxylic acid, 3,4-hexanediol-1,8-dicarboxylic acid, 4-hydroxy-3-hexanone-1,8-dicarboxylic acid, glycerol, fucoidan, iodine, chlorophyll, carotenoid, calcium, magnesium, iron, sodium, potassium, phosphate, lactic acid, acetic acid, formic acid, isoprenoids, and polyisoprenes, including rubber. Further, such products can include succinic acid, pyruvic acid, enzymes such as cellulases, polysaccharases, lipases, proteases, ligninases, and hemicellulases and may be present as a pure compound, a mixture, or an impure or diluted form.

Fermentation end-products can include polyols or sugar alcohols; for example, methanol, glycol, glycerol, erythritol, threitol, arabitol, xylitol, ribitol, mannitol, sorbitol, dulcitol, fucitol, iditol, inositol, volemitol, isomalt, maltitol, lactitol, and/or polyglycitol.

The term "fatty acid comprising material" as used herein has its ordinary meaning as known to those skilled in the art and can comprise one or more chemical compounds that include one or more fatty acid moieties as well as derivatives of these compounds and materials that comprise one or more of these compounds. Common examples of compounds that include one or more fatty acid moieties include triacylglycerides, diacylglycerides, monoacylglycerides, phospholipids, lysophospholipids, free fatty acids, fatty acid salts, soaps, fatty acid comprising amides, esters of fatty acids and monohydric alcohols, esters of fatty acids and polyhydric alcohols including glycols (e.g. ethylene glycol, propylene glycol, etc.), esters of fatty acids and polyethylene glycol, esters of fatty acids and polyethers, esters of fatty acids and polyglycol, esters of fatty acids and saccharides, esters of fatty acids with other hydroxyl-containing compounds, etc. A fatty acid comprising material can be one or more of these compounds in an isolated or purified form. It can be a material that includes one or more of these compounds that is combined or blended with other similar or different materials. It can be a material where the fatty acid comprising material occurs with or is provided with other similar or different materials, such as vegetable and animal oils; mixtures of vegetable and animal oils; vegetable and animal oil byproducts; mixtures of vegetable and animal oil byproducts; vegetable and animal wax esters; mixtures, derivatives and byproducts of vegetable and animal wax esters; seeds; processed seeds; seed byproducts; nuts; processed nuts; nut byproducts; animal matter; processed animal matter; byproducts of animal matter; corn; processed corn; corn byproducts; distiller's grains; beans; processed beans; bean byproducts; soy products; lipid containing plant, fish or animal matter; processed lipid containing plant or animal matter; byproducts of lipid containing plant, fish or animal matter; lipid containing microbial material; processed lipid containing microbial material; and byproducts of lipid containing microbial matter. Such materials can be utilized in liquid or solid forms. Solid forms include whole forms, such as cells, beans, and seeds; ground, chopped, slurried, extracted, flaked, milled, etc. The fatty acid portion of the fatty acid comprising compound can be a simple fatty acid, such as one that includes a carboxyl group attached to a substituted or un-substituted alkyl group. The substituted or unsubstituted alkyl group can be straight or branched, saturated or unsaturated. Substitutions on the alkyl group can include hydroxyls, phosphates, halogens, alkoxy, or aryl groups. The substituted or unsubstituted alkyl group can have 7 to 29 carbons and preferably 11 to 23 carbons (e.g., 8 to 30 carbons and preferably 12 to 24 carbons counting the carboxyl group) arranged in a linear chain with or without side chains and/or substitutions. Addition of the fatty acid comprising compound can be by way of adding a material comprising the fatty acid comprising compound.

The term "pH modifier" as used herein has its ordinary meaning as known to those skilled in the art and can include any material that will tend to increase, decrease or hold steady the pH of the broth or medium. A pH modifier can be an acid, a base, a buffer, or a material that reacts with other materials present to serve to raise, lower, or hold steady the pH. In one embodiment, more than one pH modifier can be used, such as more than one acid, more than one base, one or more acid with one or more bases, one or more acids with one or more buffers, one or more bases with one or more buffers, or one or more acids with one or more bases with one or more buffers. In one embodiment, a buffer can be produced in the broth or medium or separately and used as an ingredient by at least partially reacting in acid or base with a base or an acid, respectively. When more than one pH modifiers are utilized, they can be added at the same time or at different times. In one embodiment, one or more acids and one or more bases are combined, resulting in a buffer. In one embodiment, media components, such as a carbon source or a nitrogen source serve as a pH modifier; suitable media components include those with high or low pH or those with buffering capacity. Exemplary media components include acid- or base-hydrolyzed plant polysaccharides having residual acid or base, ammonia fiber explosion (AFEX) treated plant material with residual ammonia, lactic acid, corn steep solids or liquor.

"Growth phase" is used herein to describe the type of cellular growth that occurs after the "Initiation phase" and before the "Stationary phase" and the "Death phase." The growth phase is sometimes referred to as the exponential phase or log phase or logarithmic phase.

The term "plant polysaccharide" as used herein has its ordinary meaning as known to those skilled in the art and can comprise one or more polymers of sugars and sugar derivatives as well as derivatives of sugar polymers and/or other polymeric materials that occur in plant matter. Exemplary plant polysaccharides include lignin, cellulose, starch, pectin, and hemicellulose. Others are chitin, sulfonated polysaccharides such as alginic acid, agarose, carrageenan, porphyran, furcelleran and funoran. Generally, the polysaccharide can have two or more sugar units or derivatives of sugar units. The sugar units and/or derivatives of sugar units can repeat in a regular pattern, or otherwise. The sugar units can be hexose units or pentose units, or combinations of these. The derivatives of sugar units can be sugar alcohols, sugar acids, amino sugars, etc. The polysaccharides can be linear, branched, cross-linked, or a mixture thereof. One type or class of polysaccharide can be cross-linked to another type or class of polysaccharide. The concentration of saccharides in a biomass containing plant polysaccharides such as cellulose, hemicellulose, starch, or pectin can be given in terms of monosaccharide equivalents. A monosaccharide equivalent concentration is the concentration of saccharides assuming complete hydrolysis of polysaccharides to monosaccharides.

The term "saccharification" as used herein has its ordinary meaning as known to those skilled in the art and can include conversion of plant polysaccharides to lower molecular weight species that can be utilized by the organism at hand. For some organisms, this would include conversion to monosaccharides, disaccharides, trisaccharides, and oligosaccharides of up to about seven monomer units, as well as similar sized chains of sugar derivatives and combinations of sugars and sugar derivatives.

The terms "SSF" and "SHF" are known to those skilled in the art; SSF meaning simultaneous saccharification and fermentation, or the conversion from polysaccharides or oligosaccharides into monosaccharides at the same time and in the same fermentation vessel wherein monosaccharides are converted to another chemical product such as ethanol. "SHF" indicates a physical separation of the polymer hydrolysis or saccharification and fermentation processes.

The term "biomass" as used herein has its ordinary meaning as known to those skilled in the art and can include one or more biological materials that can be converted into a biofuel, chemical or other product. Biomass as used herein is synonymous with the term "feedstock" and includes corn syrup, molasses, silage, agricultural residues (corn stalks, grass, straw, grain hulls, bagasse, etc.), animal waste (manure from cattle, poultry, and hogs), Distillers Dried Solubles (DDS), Distillers Dried Grains (DDG), Condensed Distillers Solubles (CDS), Distillers Wet Grains (DWG), Distillers Dried Grains with Solubles (DDGS), woody materials (wood or bark, sawdust, timber slash, and mill scrap), municipal waste (waste paper, recycled toilet papers, yard clippings, etc.), and energy crops (poplars, willows, switchgrass, alfalfa, prairie bluestem, algae, including macroalgae, etc.). One exemplary source of biomass is plant matter. Plant matter can be, for example, woody plant matter, non-woody plant matter, cellulosic material, lignocellulosic material, hemicellulosic material, carbohydrates, pectin, starch, inulin, fructans, glucans, corn, sugar cane, grasses, switchgrass, sorghum, high biomass sorghum, bamboo, algae and material derived from these. Plants can be in their natural state or genetically modified, e.g., to increase the cellulosic or hemicellulosic portion of the cell wall, or to produce additional exogenous or endogenous enzymes to increase the separation of cell wall components. Plant matter can also include plant cell culture or plant cell tissue culture. Plant matter can be further described by reference to the chemical species present, such as proteins, polysaccharides and oils. Polysaccharides include polymers of various monosaccharides and derivatives of monosaccharides including glucose, fructose, lactose, galacturonic acid, rhamnose, etc. Plant matter also includes agricultural waste byproducts or side streams such as pomace, corn steep liquor, corn steep solids, distillers grains, peels, pits, fermentation waste, straw, lumber, sewage, garbage and food leftovers. Peels can be citrus which include, but are not limited to, tangerine peel, grapefruit peel, orange peel, tangerine peel, lime peel and lemon peel. These materials can come from farms, forestry, industrial sources, households, etc. Another non-limiting example of biomass is animal matter, including, for example milk, meat, fat, animal processing waste, and animal waste. "Feedstock" is frequently used to refer to biomass being used for a process, such as those described herein.

A "first biomass" as used herein includes starch-containing materials. For example, a first biomass includes corn, corn mash, sugar cane, sugar beets, sugar palms, sweet sorghum, nypa palm, cassava, rice, milo, sorghum, sweet potatoes, wheat, molasses, tubers, roots, stems, whole grains, barley, rye, milo, sago, cassava, tapioca, rice peas, beans, potatoes, beets, fruits, or any other starch containing materials, or combination of starch containing materials or starch containing biomasses.

"Broth" is used herein to refer to inoculated medium at any stage of growth, including the point immediately after inoculation and the period after any or all cellular activity has ceased and can include the material after post-fermentation processing. It includes the entire contents of the combination of soluble and insoluble matter, suspended matter, cells and medium, as appropriate.

The term "productivity" as used herein has its ordinary meaning as known to those skilled in the art and can include the mass of a material of interest produced in a given time in a given volume. Units can be, for example, grams per liter-hour, or some other combination of mass, volume, and time. In fermentation, productivity is frequently used to characterize how fast a product can be made within a given fermentation volume. The volume can be referenced to the total volume of the fermentation vessel, the working volume of the fermentation vessel, or the actual volume of broth being fermented. The context of the phrase will indicate the meaning intended to one of skill in the art. Productivity is different from "titer" in that productivity includes a time term, and titer is analogous to concentration. Titer and Productivity can generally be measured at any time during the fermentation, such as at the beginning, the end, or at some intermediate time, with titer relating the amount of a particular material present or produced at the point in time of interest and the productivity relating the amount of a particular material produced per liter in a given amount of time. The amount of time used in the productivity determination can be from the beginning of the fermentation or from some other time, and go to the end of the fermentation, such as when no additional material is produced or when harvest occurs, or some other time as indicated by the context of the use of the term. "Overall productivity" refers to the productivity determined by utilizing the final titer and the overall fermentation time.

"Titer" refers to the amount of a particular material present in a fermentation broth. It is similar to concentration and can refer to the amount of material made by the organism in the broth from all fermentation cycles, or the amount of material made in the current fermentation cycle or over a given period of time, or the amount of material present from whatever source, such as produced by the organism or added to the broth. Frequently, the titer of soluble species will be referenced to the liquid portion of the broth, with insolubles removed, and the titer of insoluble species will be referenced to the total amount of broth with insoluble species being present, however, the titer of soluble species can be referenced to the total broth volume and the titer of insoluble species can be referenced to the liquid portion, with the context indicating the which system is used with both reference systems intended in some cases. Frequently, the value determined referenced to one system will be the same or a sufficient approximation of the value referenced to the other.

"Concentration" when referring to material in the broth generally refers to the amount of a material present from all sources, whether made by the organism or added to the broth. Concentration can refer to soluble species or insoluble species, and is referenced to either the liquid portion of the broth or the total volume of the broth, as for "titer."

The term "biocatalyst" as used herein has its ordinary meaning as known to those skilled in the art and can include one or more enzymes and/or microorganisms, including solutions, suspensions, and mixtures of enzymes and microorganisms. In some contexts this word will refer to the possible use of either enzymes or microorganisms to serve a particular function, in other contexts the word will refer to the combined use of the two, and in other contexts the word will refer to only one of the two. The context of the phrase will indicate the meaning intended to one of skill in the art. For example, a biocatalyst can be a fermenting microorganism. The term biocatalyst includes fermenting microorganisms such as yeast, bacteria, or algae.

The terms "conversion efficiency" or "yield" as used herein have their ordinary meaning as known to those skilled in the art and can include the mass of product made from a mass of substrate. The term can be expressed as a percentage yield of the product from a starting mass of substrate. For the production of ethanol from glucose, the net reaction is generally accepted as:

$$C_6H_{12}O_6 \rightarrow 2C_2H_5OH + 2CO_2$$

and the theoretical maximum conversion efficiency, or yield, is 51% (wt.). Frequently, the conversion efficiency will be referenced to the theoretical maximum, for example, "80% of the theoretical maximum." In the case of conversion of glucose to ethanol, this statement would indicate a conversion efficiency of 41% (wt.). The context of the phrase will indicate the substrate and product intended to one of skill in the art.

"Pretreatment" or "pretreated" is used herein to refer to any mechanical, chemical, thermal, biochemical processor combination of these processes whether in a combined step or performed sequentially, that achieves disruption or expansion of the biomass so as to render the biomass more susceptible to attack by enzymes and/or microbes. In one embodiment, pretreatment includes removal or disruption of lignin so as to make the cellulose and hemicellulose polymers in the plant biomass more available to cellulolytic enzymes and/or microbes, for example, by treatment with acid or base. In one embodiment, pretreatment includes disruption or expansion of cellulosic and/or hemicellulosic material. Steam explosion, and ammonia fiber expansion (or explosion) (AFEX) are well known thermal/chemical techniques. Hydrolysis, including methods that utilize acids, bases, and/or enzymes can be used. Other thermal, chemical, biochemical, enzymatic techniques can also be used.

"Fed-batch" or "fed-batch fermentation" is used herein to include methods of culturing microorganisms where nutrients, other medium components, or biocatalysts (including, for example, enzymes, fresh organisms, extracellular broth, genetically modified plants and/or organisms, etc.) are supplied to the fermentor during cultivation, but culture broth is not harvested from the fermentor until the end of the fermentation, although it can also include "self seeding" or "partial harvest" techniques where a portion of the fermentor volume is harvested and then fresh medium is added to the remaining broth in the fermentor, with at least a portion of the inoculum being the broth that was left in the fermentor. During a fed-batch fermentation, the broth volume can increase, at least for a period, by adding medium or nutrients to the broth while fermentation organisms are present. Suitable nutrients which can be utilized include those that are soluble, insoluble, and partially soluble, including gasses, liquids and solids. In one embodiment, a fed-batch process is referred to with a phrase such as, "fed-batch with cell augmentation." This phrase can include an operation where nutrients and cells are added or one where cells with no substantial amount of nutrients are added. The more general phrase "fed-batch" encompasses these operations as well. The context where any of these phrases is used will indicate to one of skill in the art the techniques being considered.

"Sugar compounds" or "sugar streams" is used herein to indicate mostly monosaccharide sugars, dissolved, crystallized, evaporated, or partially dissolved, including but not limited to hexoses and pentoses; sugar alcohols; sugar acids; sugar amines; compounds containing two or more of these linked together directly or indirectly through covalent or ionic bonds; and mixtures thereof. Included within this description are disaccharides; trisaccharides; oligosaccharides; polysaccharides; and sugar chains, branched and/or linear, of any length. A sugar stream can consist of primarily or substantially C6 sugars, C5 sugars, or mixtures of both C6 and C5 sugars in varying ratios of said sugars. C6 sugars have a six-carbon molecular backbone and C5 sugars have a five-carbon molecular backbone.

"C5-rich" composition means that one or more steps have been taken to remove at least some of the C6 sugars originally in the composition. For example, a C5-rich composition can include no more than about 50% C6 sugars, no more than about 40% C6 sugars, no more than about 30% C6 sugars, no more than about 20% C6 sugars, no more than about 10% C6 sugars, no more than about 5% C6 sugars, or it can include from about 2% to about 10% C6 sugars by weight. Likewise, a "C6-rich" composition is one in which at least some of the originally-present C5 sugars have been removed. For example, a C6-rich composition can include no more than about 50% C5 sugars, nor more than about 40% C5 sugars, no more than about 30% C5 sugars, no more than about 20% C5 sugars, no more than about 10% C5 sugars, no more than about 5% C5 sugars, or it can include from about 2% to about 10% C5 sugars by weight.

A "liquid" composition may contain solids and a "solids" composition may contain liquids. A liquid composition refers to a composition in which the material is primarily liquid, and a solids composition is one in which the material is primarily solid.

"Gentle Pretreatment" generally refers to the collection of processes upstream of hydrolysis, which result in composition that, when hydrolyzed, produces a fermentable sugar composition. The fermentable sugar composition can be used to enhance a non-cellulosic fermentation process, such as a corn mash fermentation process. In some embodiments, the gentle pretreatment process provides a fermentable sugar composition having a favorable nutrient balance (e.g. plant-derived extracted nutrients, which are part of the composition as a result of the pretreatment process) and/or an amount of toxic compounds (e.g. phenolics and sugar degradation products, organic acids and furans, which inhibit and/or inactivate the performance of enzymes and or fermentation organisms), which is limited such that the resultant fermentable sugar composition can enhance a non-cellulosic fermentation process, such as a corn mash fermentation process. For example, a gentle pretreatment is one that results in a sugar stream that is about 25% (w/v)C6 sugars or more, about 4 g/L hydroxymethyl furfural or less, about 4 g/L furfural or less, about 10 g/L acetic acid or less, about 10 g/L formic acid or less for example as measured by typical HPLC methods referred to herein. ("About X amount of a substance or less" means the same as "no more than about" and includes zero—i.e. includes the possibility that none of that substance is present in the composition.) "Gentle pretreatment" can include one or more of: pre-processing biomass to reduce size and/or create size uniformity; pretreatment itself (process for making cellulose more accessible to hydrolysis); and post-processing steps such as washing steps.

The terms "non-cellulosic" and "sugar- or starch-based" are used interchangeably and have the same meaning. For example "non-cellulosic fermentation process" is used interchangeably and means the same thing as "sugar- and starch-based fermentation process." Starch is a carbohydrate consisting of consisting of a large number of glucose units joined by glycosidic bonds. The glycosidic bonds are typically the easily hydrolysable alpha glycosidic bonds. This polysaccharide can be produced by all green plants as an energy store. There can be two types of starch molecules: the linear and helical amylose and the branched amylopectin, although amylase can also contain branches.

Description

The following description and examples illustrate some exemplary embodiments of the disclosure in detail. Those of skill in the art will recognize that there are numerous variations and modifications of this disclosure that are encompassed by its scope. Accordingly, the description of a certain exemplary embodiment, should not be deemed to limit the scope of the present disclosure.

Corn Fermentation

To overcome the cost of corn, and issues of glycerol production and slow fermentation, several entities have tried adding mixed cellulosic-derived sugars either with or without the pretreatment liquor. There has been little or no success using such methods. One reason is that the industrial yeasts used to ferment starch are primarily C6-fermenting species. In fact, almost all yeasts require C6 sugars as a feedstock and cannot ferment pentose (C5) sugar as rapidly as C6 sugar or cannot ferment C5 sugar at all. Those that can ferment C5 sugars do not tolerate high levels of ethanol, thus are not useful in the industrial production of biofuels.

In the production of sugar-derived products through fermentation, it is important to carry out the fermentation as quickly as possible. The risk of contamination increases as the fermentation lengthens. Furthermore, the energy requirements increase the cost of fermentation, thus raising the price of the product.

Feedstock and Pretreatment of Feedstock

In one embodiment, the feedstock (biomass) contains cellulosic, hemicellulosic, and/or lignocellulosic material. The feedstock can be derived from agricultural crops, crop residues, trees, woodchips, sawdust, paper, cardboard, grasses, algae, municipal waste and other sources.

Cellulose is a linear polymer of glucose where the glucose units are connected via β (1→4) linkages. Hemicellulose is a branched polymer of a number of sugar monomers including glucose, xylose, mannose, galactose, rhamnose and arabinose, and can have sugar acids such as mannuronic acid and galacturonic acid present as well. Lignin is a cross-linked, racemic macromolecule of mostly p-coumaryl alcohol, conferyl alcohol and sinapyl alcohol. These three polymers occur together in lignoclusic materials in plant biomass. The different characteristics of the three polymers can make hydrolysis of the combination difficult as each polymer tends to shield the others from enzymatic attack.

In one embodiment, methods are provided for the pretreatment of feedstock used in the fermentation and production of the biofuels and chemicals. The pretreatment steps can include mechanical, thermal, pressure, chemical, thermochemical, and/or biochemical tests pretreatment prior to being used in a bioprocess for the production of fuels and chemicals, but untreated biomass material can be used in the process as well. Mechanical processes can reduce the particle size of the biomass material so that it can be more conveniently handled in the bioprocess and can increase the surface area of the feedstock to facilitate contact with chemicals/biochemicals/biocatalysts. Mechanical processes can also separate one type of biomass material from another. The biomass material can also be subjected to thermal and/or chemical pretreatments to render plant polymers more accessible. Multiple steps of treatment can also be used.

Mechanical processes include, are not limited to, washing, soaking, milling, size reduction, screening, shearing, size classification and density classification processes. Chemical processes include, but are not limited to, bleaching, oxidation, reduction, acid treatment, base treatment, sulfite treatment, acid sulfite treatment, basic sulfite treatment, ammonia treatment, and hydrolysis. Thermal processes include, but are not limited to, sterilization, ammonia fiber expansion or explosion ("AFEX"), steam explosion, holding at elevated temperatures, pressurized or unpressurized, in the presence or absence of water, and freezing. Biochemical processes include, but are not limited to, treatment with enzymes, including enzymes produced by genetically-modified plants, and treatment with microorganisms. Various enzymes that can be utilized include cellulase, amylase, β-glucosidase, xylanase, gluconase, and other polysaccharases; lysozyme; laccase, and other lignin-modifying enzymes; lipoxygenase, peroxidase, and other oxidative enzymes; proteases; and lipases. One or more of the mechanical, chemical, thermal, thermochemical, and biochemical processes can be combined or used separately. Such combined processes can also include those used in the production of paper, cellulose products, microcrystalline cellulose, and cellulosics and can include pulping, kraft pulping, acidic sulfite processing. The feedstock can be a side stream or waste stream from a facility that utilizes one or more of these processes on a biomass material, such as cellulosic, hemicellulosic or lignocellulosic material. Examples include paper plants, cellulosics plants, distillation plants, cotton processing plants, and microcrystalline cellulose plants. The feedstock can also include cellulose-containing or cellulosic containing waste materials. The feedstock can also be biomass materials, such as wood, grasses, corn, starch, or sugar, produced or harvested as an intended feedstock for production of ethanol or other products such as by biocatalysts.

In another embodiment, a method can utilize a pretreatment process disclosed in U.S. Patents and Patent Applications US20040152881, US20040171136, US20040168960, US20080121359, US20060069244, US20060188980, US20080176301, 5693296, 6262313, US20060024801, 5969189, 6043392, US20020038058, US5865898, US5865898, US6478965, 5986133, or US20080280338, each of which is incorporated by reference herein in its entirety.

In another embodiment, the AFEX process is be used for pretreatment of biomass. In a preferred embodiment, the AFEX process is used in the preparation of cellulosic, hemicellulosic or lignocellulosic materials for fermentation to ethanol or other products. The process generally includes combining the feedstock with ammonia, heating under pressure, and suddenly releasing the pressure. Water can be present in various amounts. The AFEX process has been the subject of numerous patents and publications.

In another embodiment, the pretreatment of biomass comprises the addition of calcium hydroxide to a biomass to render the biomass susceptible to degradation. Pretreatment comprises the addition of calcium hydroxide and water to the biomass to form a mixture, and maintaining the mixture at a relatively high temperature. Alternatively, an oxidizing agent, selected from the group consisting of oxygen and oxygen-containing gasses, can be added under pressure to the mixture. Examples of carbon hydroxide treatments are disclosed in U.S. Pat. No. 5,865,898 to Holtzapple and S. Kim and M. T. Holzapple, Bioresource Technology, 96, (2005) 1994, incorporated by reference herein in its entirety.

In one embodiment, pretreatment of biomass comprises dilute acid hydrolysis. Example of dilute acid hydrolysis treatment are disclosed in T. A. Lloyd and C. E Wyman, Bioresource Technology, (2005) 96, 1967, incorporated by reference herein in its entirety.

In another embodiment, pretreatment of biomass comprises pH controlled liquid hot water treatment. Examples of pH controlled liquid hot water treatments are disclosed in N.

Mosier et al., Bioresource Technology, (2005) 96, 1986, incorporated by reference herein in its entirety.

In one embodiment, pretreatment of biomass comprises aqueous ammonia recycle process (ARP). Examples of aqueous ammonia recycle process are described in T. H. Kim and Y. Y. Lee, Bioresource Technology, (2005) 96, 2007, incorporated by reference herein in its entirety.

In one embodiment, the above mentioned methods have two steps: a pretreatment step that leads to a wash stream, and an enzymatic hydrolysis step of pretreated-biomass that produces a hydrolysate stream. In the above methods, the pretreatment step can include acid hydrolysis, hot water pretreatment, steam explosion or alkaline reagent based methods (AFEX, ARP, and lime pretreatments). Dilute acid and hot water treatment methods can be used to solubilize all or a portion of the hemicellulose. Methods employing alkaline reagents can be used remove all, most, or a portion of the lignin during the pretreatment step. As a result, the wash stream from the pretreatment step in the former methods contains mostly hemicellulose-based sugars, whereas this stream has mostly lignin for the high-pH methods. The subsequent enzymatic hydrolysis of the residual biomass leads to mixed sugars (C5 and C6) in the alkali based pretreatment methods, while glucose is the major product in the hydrolysate from the low and neutral pH methods. Such a hydrolysate can be referred to as a C6-enriched hydrolysate. In one embodiment, the treated material is additionally treated with catalase or another similar chemical, chelating agents, surfactants, and other compounds to remove impurities or toxic chemicals or further release polysaccharides.

In one embodiment, one or more monosaccharides are produced by pretreating and/or hydrolyzing a biomass comprising cellulose, hemicellulose, and/or lignocellulose. The biomass can be pretreated according to any of the methods disclosed herein; for example, by dilute acid, hot water treatment, stream explosion, or an alkaline pretreatment. The biomass can be pretreated using a combination of techniques; for example, the biomass can be pretreated using hot water or stream explosion followed by alkaline treatment. The one or more monosaccharides can include C6 and/or C5 monosaccharides. The one or more monosaccharides can be in a C6-enriched hydrolysate. The one or more monosaccharides can be cellulosic-derived C6 monosaccharides. The cellulosic-derived C6 monosaccharides can include glucose.

A C6-enriched hydrolysate is enriched for C6 sugars; however, the C6-enriched hydrolysate can comprise C5 sugars. In one embodiment, less than about 50%, 40%, 30%, 20%, 10%, or 1% of the sugars in the C6-enriched hydrolysate are C5 sugars. In another embodiment, about 0-50%, 0-40%, 0-30%, 0-20%, 0-10%, 0-1%, 0-0.1%, 0.1-50%, 0.1-40%, 0.1-30%, 0.1-20%, 0.1-10%, 0.1-1%, 1-50%, 1-40%, 1-30%, 1-20%, 1-10%, 10-50%, 10-40%, 10-30%, 10-20%, 20-50%, 20-40%, 20-30%, 30-50%, 30-40%, of 40-50% of the sugars in a C6-enriched hydrolysate are C5 sugars. The C6-enriched hydrolysate can comprise one or more cellulosic-derived C6 monosaccharides (e.g., glucose).

In one embodiment, pretreatment of biomass comprises ionic liquid (IL) pretreatment. Biomass can be pretreated by incubation with an ionic liquid, followed by IL extraction with a wash solvent such as alcohol or water. The treated biomass can then be separated from the ionic liquid/wash-solvent solution by centrifugation or filtration, and sent to the saccharification reactor or vessel. Examples of ionic liquid pretreatment are disclosed in US publication No. 2008/0227162, incorporated herein by reference in its entirety.

In another embodiment, a method can utilize a pretreatment process disclosed in U.S. Pat. No. 4,600,590 to Dale, U.S. Pat. No. 4,644,060 to Chou, U.S. Pat. No. 5,037,663 to Dale. U.S. Pat. No. 5,171,592 to Holtzapple, et al., U.S. Pat. No. 5,939,544 to Karstens, et al., U.S. Pat. No. 5,473,061 to Bredereck, et al., U.S. Pat. No. 6,416,621 to Karstens, U.S. Pat. No. 6,106,888 to Dale, et al., U.S. Pat. No. 6,176,176 to Dale, et al., PCT publication WO2008/020901 to Dale, et al., Felix, A., et al., Anim. Prod. 51, 47-61 (1990)., Wais, A. C., Jr., et al., Journal of Animal Science, 35, No. 1,109-112 (1972), which are incorporated herein by reference in their entireties.

Alteration of the pH of a pretreated feedstock can be accomplished by washing the feedstock (e.g., with water) one or more times to remove an alkaline or acidic substance, or other substance used or produced during pretreatment. Washing can comprise exposing the pretreated feedstock to an equal volume of water 2, 3, 4, 5, 6, 7, 8, 9, 10, 11, 12, 13, 14, 15, 16, 17, 18, 19, 20, 21, 22, 23, 24, 25 or more times. In another embodiment, a pH modifier can be added. For example, an acid, a buffer, or a material that reacts with other materials present can be added to modulate the pH of the feedstock. In one embodiment, more than one pH modifier can be used, such as one or more bases, one or more bases with one or more buffers, one or more acids, one or more acids with one or more buffers, or one or more buffers. When more than one pH modifiers are utilized, they can be added at the same time or at different times. Other non-limiting exemplary methods for neutralizing feedstocks treated with alkaline substances have been described, for example in U.S. Pat. Nos. 4,048,341; 4,182,780; and 5,693,296.

In one embodiment, one or more acids can be combined, resulting in a buffer. Suitable acids and buffers that can be used as pH modifiers include any liquid or gaseous acid that is compatible with the microorganism. Non-limiting examples include peroxyacetic acid, sulfuric acid, sulfurous acid, lactic acid, citric acid, phosphoric acid, and hydrochloric acid. In some instances, the pH can be lowered to neutral pH or acidic pH, for example a pH of 7.0, 6.5, 6.0, 5.5, 5.0, 4.5, 4.0, or lower. In some embodiments, the pH is lowered and/or maintained within a range of about pH 4.5 to about 7.1, or about 4.5 to about 6.9, or about pH 5.0 to about 6.3, or about pH 5.5 to about 6.3, or about pH 6.0 to about 6.5, or about pH 5.5 to about 6.9 or about pH 6.2 to about 6.7.

In another embodiment, biomass can be pre-treated at an elevated temperature and/or pressure. In one embodiment, biomass is pre treated at a temperature range of 20° C. to 400° C. In another embodiment, biomass is pretreated at a temperature of about 20° C., 25° C., 30° C., 35° C., 40° C., 45° C., 50° C., 55° C., 60° C., 65° C., 80° C., 90° C., 100° C., 120° C., 150° C., 200° C., 250° C., 300° C., 350° C., 400° C. or higher. In another embodiment, elevated temperatures are provided by the use of steam, hot water, or hot gases. In one embodiment, steam can be injected into a biomass containing vessel. In another embodiment, the steam, hot water, or hot gas can be injected into a vessel jacket such that it heats, but does not directly contact the biomass.

In another embodiment, a biomass can be treated at an elevated pressure. In one embodiment, biomass is pre treated at a pressure range of about 1 psi to about 30 psi. In another embodiment, biomass is pre treated at a pressure or about 1 psi, 2 psi, 3 psi, 4 psi, 5 psi, 6 psi, 7 psi, 8 psi, 9 psi, 10 psi, 12 psi, 15 psi, 18 psi, 20 psi, 22 psi, 24 psi, 26 psi, 28 psi, 30 psi or more. In some embodiments, biomass can be treated with elevated pressures by the injection of steam into a biomass containing vessel. In one embodiment, the biomass can be treated to vacuum conditions prior or subsequent to alkaline or acid treatment or any other treatment methods provided herein.

In one embodiment, alkaline or acid pretreated biomass is washed (e.g. with water (hot or cold) or other solvent such as alcohol (e.g. ethanol)), pH neutralized with an acid, base, or buffering agent (e.g. phosphate, citrate, borate, or carbonate salt) or dried prior to fermentation. In one embodiment, the drying step can be performed under vacuum to increase the rate of evaporation of water or other solvents. Alternatively, or additionally, the drying step can be performed at elevated temperatures such as about 20° C., 25° C., 30° C., 35° C., 40° C., 45° C., 50° C., 55° C., 60° C., 65° C., 80° C., 90° C., 100° C., 120° C., 150° C., 200° C., 250° C., 300° C. or more.

In one embodiment, the pretreatment step includes a step of solids recovery. The solids recovery step can be during or after pretreatment (e.g., acid or alkali pretreatment), or before the drying step. In one embodiment, the solids recovery step can include the use of a sieve, filter, screen, or a membrane for separating the liquid and solids fractions. In one embodiment, a suitable sieve pore diameter size ranges from about 0.001 microns to 8 mm, such as about 0.005 microns to 3 mm or about 0.01 microns to 1 mm. In one embodiment, a sieve pore size has a pore diameter of about 0.01 microns, 0.02 microns, 0.05 microns, 0.1 microns, 0.5 microns, 1 micron, 2 microns, 4 microns, 5 microns, 10 microns, 20 microns, 25 microns, 50 microns, 75 microns, 100 microns, 125 microns, 150 microns, 200 microns, 250 microns, 300 microns, 400 microns, 500 microns, 750 microns, 1 mm or more. In one embodiment, biomass (e.g. corn stover) is processed or pretreated prior to fermentation. In one embodiment, a method of pre-treatment includes but is not limited to, biomass particle size reduction, such as for example shredding, milling, chipping, crushing, grinding, or pulverizing. In one embodiment, biomass particle size reduction can include size separation methods such as sieving, or other suitable methods known in the art to separate materials based on size. In one embodiment, size separation can provide for enhanced yields. In one embodiment, separation of finely shredded biomass (e.g. particles smaller than about 8 mm in diameter, such as, 8, 7.9, 7.7, 7.5, 7.3, 7, 6.9, 6.7, 6.5, 6.3, 6, 5.9, 5.7, 5.5, 5.3, 5, 4.9, 4.7, 4.5, 4.3, 4, 3.9, 3.7, 3.5, 3.3, 3, 2.9, 2.7, 2.5, 2.3, 2, 1.9, 1.7, 1.5, 1.3, 1, 0.9, 0.8, 0.7, 0.6, 0.5, 0.4, 0.3, 0.2, or 0.1 mm) from larger particles allows the recycling of the larger particles back into the size reduction process, thereby increasing the final yield of processed biomass. In one embodiment, a fermentative mixture is provided which comprises a pretreated lignocellulosic feedstock comprising less than about 50% of a lignin component present in the feedstock prior to pretreatment and comprising more than about 60% of a hemicellulose component present in the feedstock prior to pretreatment; and a microorganism capable of fermenting a five-carbon sugar, such as xylose, arabinose or a combination thereof, and a six-carbon sugar, such as glucose, galactose, mannose or a combination thereof. In some instances, pretreatment of the lignocellulosic feedstock comprises adding an alkaline substance which raises the pH to an alkaline level, for example NaOH. In one embodiment, NaOH is added at a concentration of about 0.5% to about 2% by weight of the feedstock. In one embodiment, pretreatment also comprises addition of a chelating agent.

Hydrolysis

In one embodiment, the biomass hydrolyzing unit provides useful advantages for the conversion of biomass to biofuels and chemical products. One advantage of this unit is its ability to produce monomeric sugars from multiple types of biomass, including mixtures of different biomass materials, and is capable of hydrolyzing polysaccharides and higher molecular weight saccharides to lower molecular weight saccharides. In one embodiment, the hydrolyzing unit utilizes a pretreatment process and a hydrolytic enzyme which facilitates the production of a sugar stream containing a concentration of a monomeric sugar or several monomeric sugars derived from cellulosic and/or hemicellulosic polymers. Examples of biomass material that can be pretreated and hydrolyzed to manufacture sugar monomers include, but are not limited to, cellulosic, hemicellulosic, lignocellulosic materials; pectins; starches; wood; paper; agricultural products; forest waste; tree waste; tree bark; leaves; grasses; sawgrass; woody plant matter; non-woody plant matter; carbohydrates; starch; inulin; fructans; glucans; corn; sugar cane; sorghum, other grasses; bamboo, algae, and material derived from these materials. This ability to use a very wide range of pretreatment methods and hydrolytic enzymes gives distinct advantages in biomass fermentations. Various pretreatment conditions and enzyme hydrolysis can enhance the extraction of sugars from biomass, resulting in higher yields, higher productivity, greater product selectivity, and/or greater conversion efficiency.

In one embodiment, the enzyme treatment is used to hydrolyze various higher saccharides (higher molecular weight) present in biomass to lower saccharides (lower molecular weight), such as in preparation for fermentation by biocatalysts such as yeasts to produce ethanol, hydrogen, or other chemicals such as organic acids including succinic acid, formic acid, acetic acid, and lactic acid. These enzymes and/or the hydrolysate can be used in fermentations to produce various products including fuels, and other chemicals.

In one example, the process for converting biomass material into ethanol includes pretreating the biomass material (e.g., "feedstock"), hydrolyzing the pretreated biomass to convert polysaccharides to oligosaccharides, further hydrolyzing the oligosaccharides to monosaccharides, and converting the monosaccharides to biofuels and chemical products. Enzymes such as cellulases, polysaccharases, lipases, proteases, ligninases, and hemicellulases, help produce the monosaccharides can be used in the biosynthesis of fermentation end-products. Biomass material that can be utilized includes woody plant matter, non-woody plant matter, cellulosic material, lignocellulosic material, hemicellulosic material, carbohydrates, pectin, starch, inulin, fructans, glucans, corn, algae, sugarcane, other grasses, switchgrass, bagasse, wheat straw, barley straw, rice straw, corncobs, bamboo, citrus peels, sorghum, high biomass sorghum, seed hulls, and material derived from these. The final product can then be separated and/or purified, as indicated by the properties for the desired final product. In some instances, compounds related to sugars such as sugar alcohols or sugar acids can be utilized as well.

Chemicals that can be used in the methods disclosed herein can be purchased from a commercial supplier, such as Sigma-Aldrich. Additionally, commercial enzyme cocktails (e.g. Accellerase™ 1000, CelluSeb-TL, CelluSeb-TS, Cellic™ CTec, STARGEN™, Maxalig™, Spezyme®, Distillase®, G-Zyme®, Fermenzyme®, Fermgen™, GC 212, or Optimash™) or any other commercial enzyme cocktail can be purchased from vendors such as Specialty Enzymes & Biochemicals Co., Genencor, or Novozymes. Alternatively, enzyme cocktails can be prepared by growing one or more organisms such as for example a fungi (e.g. a *Trichoderma*, a *Saccharomyces*, a *Pichia*, a White Rot Fungus etc.), a bacteria (e.g. a *Clostridium*, or a coliform bacterium, a *Zymomonas* bacterium, *Sacharophagus degradans* etc.) in a suitable medium and harvesting enzymes produced therefrom. In some embodiments, the harvesting can include one or more steps of purification of enzymes.

In one embodiment, treatment of biomass comprises enzyme hydrolysis. In one embodiment, a biomass is treated with an enzyme or a mixture of enzymes, e.g., endoglucanases, exoglucanases, cellobiohydrolases, cellulase, beta-glucosidases, glycoside hydrolases, glycosyltransferases, lyases, esterases, amylases, glucoamylases, and proteins containing carbohydrate-binding modules. In one embodiment, the enzyme or mixture of enzymes is one or more individual enzymes with distinct activities. In another embodiment, the enzyme or mixture of enzymes can be enzyme domains with a particular catalytic activity. For example, an enzyme with multiple activities can have multiple enzyme domains, including for example glycoside hydrolases, glycosyltransferases, lyases and/or esterases catalytic domains.

In one embodiment, enzymes that degrade polysaccharides are used for the hydrolysis of biomass and can include enzymes that degrade cellulose, namely, cellulases. Examples of some cellulases include endocellulases and exocellulases that hydrolyze beta-1,4-glucosidic bonds.

In one embodiment, enzymes that degrade polysaccharides are used for the hydrolysis of biomass and can include enzymes that have the ability to degrade hemicellulose, namely, hemicellulases. Hemicellulose can be a major component of plant biomass and can contain a mixture of pentoses and hexoses, for example, D-xylopyranose, L-arabinofuranose, D-mannopyranose, Dglucopyranose, D-galactopyranose, D-glucopyranosyluronic acid and other sugars. In one embodiment, enzymes that degrade polysaccharides are used for the hydrolysis of biomass and can include enzymes that have the ability to degrade pectin, namely, pectinases. In plant cell walls, the cross-linked cellulose network can be embedded in a matrix of pectins that can be covalently cross-linked to xyloglucans and certain structural proteins. Pectin can comprise homogalacturonan (HG) or rhamnogalacturonan (RH).

In one embodiment, hydrolysis of biomass includes enzymes that can hydrolyze starch. Enzymes that hydrolyze starch include alpha-amylase, glucoamylase, beta-amylase, exo-alpha-1,4-glucanase, and pullulanase.

In one embodiment, hydrolysis of biomass comprises hydrolases that can include enzymes that hydrolyze chitin. In another embodiment, hydrolases can include enzymes that hydrolyze lichen, namely, lichenase.

In one embodiment, after pretreatment and/or hydrolysis by any of the above methods the feedstock contains cellulose, hemicellulose, soluble oligomers, simple sugars, lignin, volatiles and ash. The parameters of the hydrolysis can be changed to vary the concentration of the components of the pretreated feedstock. For example, a hydrolysis can be chosen so that the concentration of soluble C5 saccharides is high and the concentration of lignin is low after hydrolysis. Examples of parameters of the hydrolysis include temperature, pressure, time, concentration, composition and pH.

In one embodiment, the parameters of the pretreatment and hydrolysis are changed to vary the concentration of the components of the pretreated feedstock such that concentration of the components in the pretreated and hydrolyzed feedstock is optimal for fermentation with a microbe such as a yeast or bacterium microbe.

In one embodiment, the parameters of the pretreatment are changed to encourage the release of the components of a genetically modified feedstock such as enzymes stored within a vacuole to increase or complement the enzymes synthesized by biocatalyst to produce optimal release of the fermentable components during hydrolysis and fermentation.

In one embodiment, the parameters of the pretreatment and hydrolysis are changed such that concentration of accessible cellulose in the pretreated feedstock is 1%, 5%, 10%, 12%, 13%, 14%, 15%, 16%, 17%, 19%, 20%, 30%, 40% or 50%. In one embodiment, the parameters of the pretreatment are changed such that concentration of accessible cellulose in the pretreated feedstock is 5% to 30%. In one embodiment, the parameters of the pretreatment are changed such that concentration of accessible cellulose in the pretreated feedstock is 10% to 20%.

In one embodiment, the parameters of the pretreatment are changed such that concentration of hemicellulose in the pretreated feedstock is 1%, 5%, 10%, 12%, 13%, 14%, 15%, 16%, 17%, 19%, 20%, 21%, 22%, 23%, 24%, 25%, 26%, 27%, 28%, 29%, 30%, 40% or 50%. In one embodiment, the parameters of the pretreatment are changed such that concentration of hemicellulose in the pretreated feedstock is 5% to 40%. In one embodiment, the parameters of the pretreatment are changed such that concentration of hemicellulose in the pretreated feedstock is 10% to 30%.

In one embodiment, the parameters of the pretreatment and hydrolysis are changed such that concentration of soluble oligomers in the pretreated feedstock is 1%, 10%, 15%, 20%, 25%, 30%, 35%, 40%, 45%, 50%, 55%, 60%, 65%, 70%, 75%, 80%, 85%, 90%, 95%, or 99%. Examples of soluble oligomers include, but are not limited to, cellobiose and xylobiose. In one embodiment, the parameters of the pretreatment are changed such that concentration of soluble oligomers in the pretreated feedstock is 30% to 90%. In one embodiment, the parameters of the pretreatment and/or hydrolysis are changed such that concentration of soluble oligomers in the pretreated feedstock is 45% to 80%.

In one embodiment, the parameters of the pretreatment and hydrolysis are changed such that concentration of simple sugars in the pretreated feedstock is 1%, 5%, 10%, 12%, 13%, 14%, 15%, 16%, 17%, 19%, 20%, 30%, 40% or 50%. In one embodiment, the parameters of the pretreatment and hydrolysis are changed such that concentration of simple sugars in the pretreated feedstock is 0% to 20%. In one embodiment, the parameters of the pretreatment and hydrolysis are changed such that concentration of simple sugars in the pretreated feedstock is 0% to 5%. Examples of simple sugars include, but are not limited to, C5 and C6 monomers and dimers.

In one embodiment, the parameters of the pretreatment are changed such that concentration of lignin in the pretreated and/or hydrolyzed feedstock is 1%, 5%, 10%, 12%, 13%, 14%, 15%, 16%, 17%, 19%, 20%, 30%, 40% or 50%. In one embodiment, the parameters of the pretreatment and/or hydrolysis are changed such that concentration of lignin in the pretreated feedstock is 0% to 20%. In one embodiment, the parameters of the pretreatment and/or hydrolysis are changed such that concentration of lignin in the pretreated feedstock is 0% to 5%. In one embodiment, the parameters of the pretreatment and hydrolysis are changed such that concentration of lignin in the pretreated and/or hydrolyzed feedstock is less than 1% to 2%. In one embodiment, the parameters of the pretreatment and/or hydrolysis are changed such that the concentration of phenolics is minimized.

In one embodiment, the parameters of the pretreatment and/or hydrolysis are changed such that concentration of furfural and low molecular weight lignin in the pretreated and/or hydrolyzed feedstock is less than 10%, 9%, 8%, 7%, 6%, 5%, 4%, 3%, 2%, or 1%. In one embodiment, the parameters of the pretreatment and/or hydrolysis are changed such that concentration of furfural and low molecular weight lignin in the pretreated and/or hydrolyzed feedstock is less than 1% to 2%.

In one embodiment, the parameters of the pretreatment and/or hydrolysis are changed such that the concentration of simple sugars is at least 75% to 85%, and the concentration of lignin is 0% to 5% and the concentration of furfural and low molecular weight lignin in the pretreated feedstock is less than 1% to 2%.

In one embodiment, the parameters of the pretreatment and/or hydrolysis are changed to obtain a high concentration of hemicellulose and a low concentration of lignin. In one embodiment, the parameters of the pretreatment and/or hydrolysis are changed to obtain a high concentration of hemicellulose and a low concentration of lignin such that concentration of the components in the pretreated stock is optimal for fermentation with a microbe such as biocatalyst.

In one embodiment, more than one of these steps can occur at any given time. For example, hydrolysis of the pretreated feedstock and hydrolysis of the oligosaccharides can occur simultaneously, and one or more of these can occur simultaneously to the conversion of monosaccharides to a fuel or chemical.

In another embodiment, an enzyme can directly convert the polysaccharide to monosaccharides. In some instances, an enzyme can hydrolyze the polysaccharide to oligosaccharides and the enzyme or another enzyme can hydrolyze the oligosaccharides to monosaccharides.

In another embodiment, the enzymes can be added to the fermentation or they can be produced by microorganisms present in the fermentation. In one embodiment, the microorganism present in the fermentation produces some enzymes. In another embodiment, enzymes are produced separately and added to the fermentation.

For the overall conversion of pretreated biomass to final product to occur at high rates, the enzymes for each conversion step can be present with sufficiently high activity. If one of these enzymes is missing or is present in insufficient quantities, the production rate of an end product can be reduced. The production rate can also be reduced if the microorganisms responsible for the conversion of monosaccharides to product only slowly take up monosaccharides and/or have only limited capability for translocation of the monosaccharides and intermediates produced during the conversion to end product. Additions of fractions obtained from pretreatment and/or pretreatment and hydrolysis can increase initial or overall growth rates. In another embodiment, oligomers are taken up slowly by a biocatalyst, necessitating an almost complete conversion of polysaccharides and oligomers to monomeric sugars.

In another embodiment, the enzymes of the method are produced by a biocatalyst, including a range of hydrolytic enzymes suitable for the biomass materials used in the fermentation methods. In one embodiment, a biocatalyst is grown under conditions appropriate to induce and/or promote production of the enzymes needed for the saccharification of the polysaccharide present. The production of these enzymes can occur in a separate vessel, such as a seed fermentation vessel or other fermentation vessel, or in the production fermentation vessel where ethanol production occurs. When the enzymes are produced in a separate vessel, they can, for example, be transferred to the production fermentation vessel along with the cells, or as a relatively cell free solution liquid containing the intercellular medium with the enzymes. When the enzymes are produced in a separate vessel, they can also be dried and/or purified prior to adding them to the hydrolysis or the production fermentation vessel. The conditions appropriate for production of the enzymes are frequently managed by growing the cells in a medium that includes the biomass that the cells will be expected to hydrolyze in subsequent fermentation steps. Additional medium components, such as salt supplements, growth factors, and cofactors including, but not limited to phytate, amino acids, and peptides can also assist in the production of the enzymes utilized by the microorganism in the production of the desired products.

Fermentation

Provided herein are methods and compositions for producing one or more fermentation products from blended feedstocks. The blended feedstocks can comprise a first biomass and one or more cellulosic-derived C6 monosaccharides. The first biomass can comprise non-cellulosic polysaccharides (e.g., starch). The source of the one or more cellulosic-derived C6 monosaccharides can be a C6-enriched hydrolysate. The C6-enriched hydrolysate can be produced by pretreating and/or hydrolyzing a biomass comprising cellulose, hemicellulose, or lignocellulose.

A blended feedstock can comprise from about 1% to about 50% solids from a first biomass. For example, the blended feedstock can comprise about 1-50%, 10-50%, 20-40%, 20-36%, 20-35%, 20-34%, 20-33%, 20-32%, 20-31%, 20-30%, 25-36%, 25-35%, 25-34%, 25-33%, 25-32%, 25-31%, 25-30%, 30-36%, 30-35%, 30-34%, 30-33%, 30-32%, or 30-31% solids from the first biomass. In one embodiment, the first biomass comprises non-cellulosic saccharides. In embodiment, the non-cellulosic saccharides comprise starch.

A blended feedstock can be produced by combining a first biomass (e.g., containing non-cellulosic saccharides such as starch) with one or more cellulosic-derived C6 monosaccharides. The one or more cellulosic-derived C6 monosaccharides can be at a concentration of from about 1% to about 70% w/v prior to combining with the first biomass. For example, the one or more cellulosic-derived C6 monosaccharides can be at a concentration of about 1-70% w/v, 1-60% w/v, 1-55% w/v, 1-50% w/v, 1-40% w/v, 1-30% w/v, 1-20% w/v, 1-10% w/v, 10-70% w/v, 10-60% w/v, 10-55% w/v, 10-50% w/v, 10-40% w/v, 10-30% w/v, 10-20% w/v, 20-70% w/v, 20-60% w/v, 20-55% w/v, 20-50% w/v, 20-40% w/v, 20-30% w/v, 30-70% w/v, 30-60% w/v, 30-55% w/v, 30-50% w/v, 30-40% w/v, 40-70% w/v, 40-60% w/v, 40-55% w/v, 40-50% w/v, 50-70% w/v, 50-60% w/v, 50-55% w/v, 55-70% w/v, 55-60% w/v, or 60-70% w/v prior to combining with the first biomass.

A blended feedstock can be produced by combining a first biomass (e.g., containing non-cellulosic saccharides such as starch) with one or more cellulosic-derived monosaccharides. The one or more cellulosic-derived monosaccharides can be C6 saccharides and/or C5 saccharides. The one or more cellulosic-derived monosaccharides can be in a crude-lysate from the pretreatment and/or hydrolysis of cellulose, hemicellulose, and/or lignocellulosic material. The one or more cellulosic-derived monosaccharides can comprise less than 50%, 45%, 40%, 35%, 30%, 25%, 20%, 15%, 10%, 5%, 4%, 3%, 2%, 1.5%, 1%, 0.9%, 0.8%, 0.7%, 0.6%, 0.5%, 0.4%, 0.3%, 0.2%, 0.1% or less w/v of one or more inhibitory compounds. The one or more inhibitory compounds can be one or more byproducts of the pretreatment and/or hydrolysis of cellulose, hemicellulose, and/or lignocellulose. The one or more inhibitory compounds can comprise one or more organic acids such as acetic acid, lactic acid, or formic acid, and/or one or more furans such as hydroxy methyl furfural or furfural, or a combination thereof.

Enhanced rates of fermentation can be achieved using blended feedstocks comprising a first biomass containing non-cellulosic polysaccharides (e.g., starch) and one or more cellulosic-derived C6 monosaccharides (e.g., in a C6-enriched hydrolysate) in comparison to fermentation of the first biomass without the one or more cellulosic-derived C6 monosaccharides. The enhanced rates of fermentation can be from about 1% higher to about 100% higher; for example, about 1-100%, 1-75%, 1-50%, 1-25%, 1-10%, 10-100%, 10-75%, 10-50%, 10-25%, 25-100%, 25-75%, 25-50%, 50-100%, 50-75%, 75-100%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 55%, 60%, 65%, 70%, 75%, 80%, 85%, 90%, 95%, or 100% higher.

Increased yields of one or more fermentation end-products can be achieved using blended feedstocks comprising a first biomass containing non-cellulosic polysaccharides (e.g., starch) and one or more cellulosic-derived C6 monosaccharides (e.g., from a C6-enriched hydrolysate) in comparison to fermentation of the first biomass without the one or more cellulosic-derived C6 monosaccharides. The increased yields of one or more fermentation end-products can be from about 1% higher to about 100% higher; for example, about 1-100%, 1-75%, 1-50%, 1-25%, 1-10%, 10-100%, 10-75%, 10-50%, 10-25%, 25-100%, 25-75%, 25-50%, 50-100%, 50-75%, 75-100%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 55%, 60%, 65%, 70%, 75%, 80%, 85%, 90%, 95%, or 100% higher.

A blended feedstock can be prepared by combining a first biomass with one or more cellulosic-derived C6 monosaccharides. The first biomass can comprise non-cellulosic polysaccharides such as starch. The one or more cellulosic-derived monosaccharides can be produced by the pretreatment and/or hydrolysis of a second biomass. The second biomass can comprise cellulose, hemicellulose, or lignocellulose. The pretreatment and/or hydrolysis of the second biomass can produce a C6-enriched hydrolysate. In one embodiment, the one or more cellulosic-derived C6 monosaccharides (e.g., from a C6-enriched hydrolysate) are at a concentration that differs from the concentration of saccharides in the first biomass by less than about +/−50%, 40%, 30%, 20%, 15%, 10%, 5%, or 1%, wherein the concentration of saccharides in the first biomass assumes complete hydrolysis of the first biomass to monomers (e.g., is in monosaccharide equivalents).

A blended feedstock can be prepared by combining a first biomass with one or more cellulosic-derived C6 monosaccharides. The first biomass can comprise non-cellulosic polysaccharides such as starch. The one or more monosaccharides can be produced by the pretreatment and/or hydrolysis of a second biomass. The second biomass can comprise cellulose, hemicellulose, or lignocellulose. The pretreatment and/or hydrolysis of the second biomass can produce a C6-enriched hydrolysate. In one embodiment, the first biomass and the one or more cellulosic-derived C6 monosaccharides (e.g., from a C6-enriched hydrolysate) are combined in about a 50:50, 55:45, 60:40, 65:35, 70:30, 75:35, 80:20, 85:15, 90:10, 95:5, or 99:1 ratio. The ratio can be a weight to weight ratio, a weight to volume ratio, or a volume to volume ratio.

Exposing microorganisms such as bacteria or yeast to hypertonic solution can cause an efflux of cellular water into the medium. In order to counteract the outflow of water molecules during growth, microorganisms can produce and accumulate one or more osmoregulatory molecules such as polyhydroxy compounds. (e.g., see Nevoit and Stahl (1997) FEMS Microbiology Review 21:231-241 and Parekh and Pandey (1985) Biotechnology and Bioengineering 27: 1089-1091, each of which is incorporated by reference in its entirety). During ethanolic fermentation of starch-containing compounds, microorganisms such as yeast can redirect part of the carbon released during enzymatic hydrolysis of starch to one or more other products such as polyols or sugar alcohols (e.g., glycerol) instead of fermentation end-products such as ethanol. This can occur, for example, when glucose is overly abundant during the fermentation reaction, for example, due to the conversion of starch to glucose monomers or the addition of one or more cellulosic-derived C6 monosaccharides. Environmental factors affecting these pathways can include oxygen availability, type of nitrogen source, osmotic pressure, heat and pH. For example, when glucose is overly abundant, a high osmotic pressure can shift metabolism to the production of glycerol. Therefore, it may be possible to maintain high ethanol production using fed-batch fermentations. In one embodiment, one or more cellulosic-derived C6 monosaccharides are added over time in a fed-batch fermentation reaction comprising a first biomass containing non-cellulosic saccharides such as starch.

Provided herein are methods and compositions for producing one or more-fermentation end-products wherein the production of one or more other products (e.g., osmoregulatory molecules) such as polyols or sugar alcohols (e.g., glycerol) is reduced. Reduced production of polyols such as glycerol can be achieved using blended feedstocks comprising a first biomass and one or more cellulosic-derived C6 monosaccharides. The first biomass can comprise non-cellulosic polysaccharides such as starch. The one or more cellulosic-derived C6 monosaccharides can be produced by the pretreatment and/or hydrolysis of a second biomass. The second biomass can comprise cellulose, hemicellulose, or lignocellulose. The one or more cellulosic-derived C6 monosaccharides can be in a C6-enriched hydrolysate. The amount of one or more other products produced can be from about 1% to about 100% lower; for example, about 1-100%, 1-75%, 1-50%, 1-25%, 1-10%, 10-100%, 10-75%, 10-50%, 10-25%, 25-100%, 25-75%, 25-50%, 50-100%, 50-75%, 75-100%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 55%, 60%, 65%, 70%, 75%, 80%, 85%, 90%, 95%, or 100% lower. In one embodiment, the one or more cellulosic-derived C6 monosaccharides are added in a fed batch manner and the reduced production of the one or more other products is in comparison to a non-fed batch fermentation reaction.

Disclosed herein are fed-batch fermentation reactions in which a first biomass (e.g., containing non-cellulosic saccharides such as starch) and one or more cellulosic-derived C6 monosaccharides are combined to produce a blended feedstock in a broth. In a fed-batch reaction, the one or more cellulosic-derived C6 monosaccharides can be added at a rate of from about 0.001 mL/min/L of broth to about 50 mL/min/L of broth. For example, the one or more cellulosic-derived C6 monosaccharides can be added at a rate of about 0.001-50 mL/min/L, 0.001-25 mL/min/L, 0.001-10 mL/min/L, 0.001-5 mL/min/L, 0.001-1 mL/min/L, 0.001-0.7 mL/min/L, 0.001-0.5 mL/min/L, 0.001-0.1 mL/min/L, 0.001-0.01 mL/min/L, 0.01-50 mL/min/L, 0.01-25 mL/min/L, 0.01-10 mL/min/L, 0.01-5 mL/min/L, 0.01-1 mL/min/L, 0.01-0.7 mL/min/L, 0.01-0.5 mL/min/L, 0.01-0.1 mL/min/L, 0.1-50 mL/min/L, 0.1-25 mL/min/L, 0.1-10 mL/min/L, 0.1-5 mL/min/L, 0.1-1 mL/min/L, 0.1-0.7 mL/min/L, 0.1-0.5 mL/min/L, 0.5-50 mL/min/L, 0.5-25 mL/min/L, 0.5-10 mL/min/L, 0.5-5 mL/min/L, 0.5-1 mL/min/L, 0.5-0.7 mL/min/L, 0.7-50 mL/min/L, 0.7-25 mL/min/L, 0.7-10 mL/min/L, 0.7-5 mL/min/L, 0.7-1 mL/min/L, 1-50 mL/min/L, 1-25 mL/min/L, 1-10 mL/min/L, 1-5 mL/min/L, 5-50 mL/min/L, 5-25 mL/min/L, 5-10 mL/min/L, 10-50 mL/min/L, 10-25 mL/min/L, 25-50 mL/min/L, 0.001 mL/min/L, 0.002 mL/min/L, 0.003 mL/min/L, 0.004 mL/min/L, 0.005 mL/min/L, 0.006 mL/min/L, 0.007 mL/min/L, 0.008 mL/min/L, 0.009 mL/min/L, 0.01 mL/min/L, 0.02 mL/min/L, 0.03 mL/min/L, 0.04 mL/min/L, 0.05 mL/min/L, 0.06 mL/min/L, 0.07 mL/min/L, 0.08 mL/min/L, 0.09 mL/min/L, 0.1 mL/min/L, 0.2 mL/min/L, 0.3 mL/min/L, 0.4 mL/min/L, 0.5 mL/min/L, 0.6 mL/min/L, 0.7 mL/min/L, 0.8 mL/min/L, 0.9 mL/min/L, 1 mL/min/L, 1.1 mL/min/L, 1.2 mL/min/L, 1.3 mL/min/L, 1.4 mL/min/L, 1.5 mL/min/L, 1.6 mL/min/L, 1.7 mL/min/L, 1.8 mL/min/L, 1.9 mL/min/L, 2 mL/min/L, 2.5 mL/min/L, 3 mL/min/L, 3.5 mL/min/L, 4 mL/min/L, 4.5 mL/min/L, 5 mL/min/L, 5.5 mL/min/L, 6 mL/min/L, 6.5 mL/min/L, 7 mL/min/L, 7.5 mL/min/L, 8 mL/min/L, 8.5 mL/min/L, 9 mL/min/L, 9.5 mL/min/L, 10 mL/min/L, 11 mL/min/L, 12 mL/min/L, 13 mL/min/L, 14 mL/min/L, 15 mL/min/L, 16 mL/min/L, 17 mL/min/L, 18 mL/min/L, 19 mL/min/L, 20 mL/min/L, 21 mL/min/L, 22 mL/min/L, 23 mL/min/L, 24 mL/min/L, 25 mL/min/L, 26 mL/min/L, 27 mL/min/L, 28 mL/min/L, 29 mL/min/L, 30 mL/min/L, 31 mL/min/L, 32 mL/min/L, 33 mL/min/L, 34 mL/min/L, 35 mL/min/L, 36 mL/min/L, 37 mL/min/L, 38 mL/min/L, 39 mL/min/L, 40 mL/min/L, 41 mL/min/L, 42 mL/min/L, 43 mL/min/L, 44 mL/min/L, 45 mL/min/L, 46 mL/min/L, 47 mL/min/L, 48 mL/min/L, 49 mL/min/L, or 50 mL/min/L of broth.

In one embodiment, the concentration of monosaccharides in a blended feedstock prior to contacting with one or more biocatalysts (e.g., at the start of a fermentation or simultaneous saccharification and fermentation reaction) can be less than about 100 g/L; for example, less than about 100 g/L, 90 g/L, 80 g/L, 70 g/L, 60 g/L, 50 g/L, 40 g/L, 30 g/L, 25 g/L, 20 g/L, 15 g/L, 10 g/L, 9 g/L, 8 g/L, 7 g/L, 6 g/L, 5 g/L, 4 g/L, 3 g/L, 2 g/L, or 1 g/L. In another embodiment, the concentration of monosaccharides in a blended feedstock prior to contacting with one or more biocatalysts (e.g., at the start of a fermentation or simultaneous saccharification and fermentation reaction) can be from about 1 g/L to about 100 g/L; for example, about 1-100 g/L, 1-75 g/L, 1-50 g/L, 1-25 g/L, 1-10 g/L, 10-100 g/L, 10-75 g/L, 10-50 g/L, 10-25 g/L, 25-100 g/L, 25-75 g/L, 25-50 g/L, 50-100 g/L, 50-75 g/L, or 75-100 g/L.

The present disclosure also provides a fermentative mixture comprising: a cellulosic feedstock pre-treated with an alkaline or acid substance and at a temperature of from about 80° C. to about 120° C.; subsequently hydrolyzed with an enzyme mixture, and a microorganism capable of fermenting a five-carbon sugar and/or a six-carbon sugar. In one embodiment, the five-carbon sugar is xylose, arabinose, or a combination thereof. In one embodiment, the six-carbon sugar is glucose, galactose, mannose, or a combination thereof. In one embodiment, the alkaline substance is NaOH. In some embodiments, NaOH is added at a concentration of about 0.5% to about 2% by weight of the feedstock. In one embodiment, the acid is equal to or less than 2% HCl or $H_2SO_4$. In one embodiment, the microorganism is a *Rhodococcus* strain, a *Clostridium* strain, a *Trichoderma* strain, a *Saccharomyces* strain, a *Zymomonas* strain, or another microorganism suitable for fermentation of biomass. In another embodiment, the fermentation process comprises fermentation of the biomass using a microorganism that is *Clostridium phytofermentans, Clostridium algidixylanolyticum, Clostridium xylanolyticum, Clostridium cellulovorans, Clostridium cellulolyticum, Clostridium thermocellum, Clostridium josui, Clostridium papyrosolvens, Clostridium cellobioparum, Clostridium hungatei, Clostridium cellulosi, Clostridium stercorarium, Clostridium termitidis, Clostridium thermocopriae, Clostridium celerecrescens, Clostridium polysaccharolyticum, Clostridium populeti, Clostridium lentocellum, Clostridium chartatabidum, Clostridium aldrichii, Clostridium herbivorans, Acetivibrio cellulolyticus, Bacteroides cellulosolvens, Caldicellulosiruptor saccharolyticum, Rhodococcus opacus, Ruminococcus albus, Ruminococcus flavefaciens, Fibrobacter succinogenes, Eubacterium cellulosolvens, Butyrivibrio fibrisolvens, Anaerocellum thermophilum, Halocella cellulolytica, Thermoanaerobacterium thermosaccharolyticum, Sacharophagus degradans*, or *Thermoanaerobacterium saccharolyticum*. In still another embodiment, the microorganism is genetically modified to enhance activity of one or more hydrolytic enzymes, such as a genetically-modified *Saccaromyces cerevisae*.

In one embodiment, a wild type or a genetically-improved microorganism can be used for chemical production by fermentation. Methods to produce a genetically-improved strain can include genetic modification, mutagenesis, and adaptive processes, such as directed evolution. For example, yeasts can be genetically-modified to ferment C5 sugars. Other useful yeasts are species of *Candida, Cryptococcus, Debaryomyces, Deddera, Hanseniaspora, Kluyveromyces, Pichia, Schizosaccharomyces*, and *Zygosaccharomyces*. *Rhodococus* strains, such as *Rhodococcus opacus* variants are a source of triacylglycerols and other storage lipids. (See, e.g., Walternann, et al., Microbiology 146:1143-1149 (2000)). Other useful organisms for fermentation include, but are not limited to, yeasts, especially *Saccaromyces* strains and bacteria such as *Clostridium phytofermentans, Thermoanaerobacter ethanolicus, Clostridium thermocellum, Clostridium beijerinickii, Clostridium acetobutylicum, Clostridium tyrobutyricum, Clostridium thermobutyricum, Thermoanaerobacterium saccharolyticum, Thermoanaerobacter thermohydrosulfuricus, Clostridium acetobutylicum, Moorella* ssp., *Carboxydocella* ssp., *Zymomonas mobilis*, recombinant *E. Coli, Klebsiella oxytoca, Rhodococcus opacus* and *Clostridium beijerickii*.

An advantage of yeasts are their ability to grow under conditions that include elevated ethanol concentration, high sugar concentration, low sugar concentration, and/or operate under anaerobic conditions. These characteristics, in various combinations, can be used to achieve operation with long or short fermentation cycles and can be used in combination with batch fermentations, fed batch fermentations, self-seeding/partial harvest fermentations, and recycle of cells from the final fermentation as inoculum.

Examples of yeasts that can be used as a biocatalyst or fermentive microorganism in the methods disclosed herein include but are not limited to, species found in the genus *Ascoidea, Brettanomyces, Candida, Cephaloascus, Coccidiascus, Dipodascus, Eremothecium, Galactomyces, Kluyveromyces, Pichia, Saccharomyces, Schizosaccharomyces, Sporopachydermia, Torulaspora, Yarrowia*, or *Zygosaccharomyces*; for example, Ascoidea rebescens, Brettanomyces anomalus, Brettanomyces bruxellensis, Brettanomyces claussenii, Brettanomyces custersianus, Brettanomyces lambicus, Brettanomyces naardenensis, Brettanomyces nanus, Candida albicans, Candida ascalaphidarum, Candida amphixiae, Candida antarctica, Candida argentea, Candida atlantica, Candida atmosphaerica, Candida blattae, Candida carpophila, Candida cerambycidarum, Candida chauliodes, Candida corydali, Candida dosseyi, Candida dubliniensis, Candida ergatensis, Candida fructus, Candida glabrata, Candida fermentati, Candida guilliermondii, Candida haemulonii, Candida insectamens, Candida insectorum,

*Candida intermedia, Candida jeffresii, Candida kefyr, Candida krusei, Candida lusitaniae, Candida lyxosophila, Candida maltosa, Candida marina, Candida membranifaciens, Candida milleri, Candida oleophila, Candida oregonensis, Candida parapsilosis, Candida quercitrusa, Candida rugosa, Candida sake, Candida shehatea, Candida temnochilae, Candida tenuis, Candida tropicalis, Candida tsuchiyae, Candida sinolaborantium, Candida sojae, Candida subhashii, Candida viswanathii, Candida utilis, Cephaloascus fragrans, Coccidiascus legeri, Dypodascus albidus, Eremothecium cymbalariae, Galactomyces candidum, Galactomyces geotrichum, Kluyveromyces aestuarii, Kluyveromyces africanus, Kluyveromyces bacillisporus, Kluyveromyces blattae, Kluyveromyces dobzhanskii, Kluyveromyces hubeiensis, Kluyveromyces lactis, Kluyveromyces lodderae, Kluyveromyces marxianus, Kluyveromyces nonfermentans, Kluyveromyces piceae, Kluyveromyces sinensis, Kluyveromyces thermotolerans, Kluyveromyces waltii, Kluyveromyces wickerhamii, Kluyveromyces yarrowii, Pichia anomola, Pichia heedii, Pichia guilliermondii, Pichia kluyveri, Pichia membranifaciens, Pichia norvegensis, Pichia ohmeri, Pichia pastoris, Pichia subpelliculosa, Saccharomyces bayanus, Saccharomyces boulardii, Saccharomyces bulderi, Saccharomyces cariocanus, Saccharomyces cariocus, Saccharomyces cerevisiae, Saccharomyces chevalieri, Saccharomyces dairenensis, Saccharomyces ellipsoideus, Saccharomyces eubayanus, Saccharomyces exiguus, Saccharomyces florentinus, Saccharomyces kluyveri, Saccharomyces martiniae, Saccharomyces monacensis, Saccharomyces norbensis, Saccharomyces paradoxus, Saccharomyces pastorianus, Saccharomyces spencerorum, Saccharomyces turicensis, Saccharomyces unisporus, Saccharomyces uvarum, Saccharomyces zonatus, Schizosaccharomyces cryophilus, Schizosaccharomyces japonicus, Schizosaccharomyces octosporus, Schizosaccharomyces pombe, Sporopachydermia cereana, Sporopachydermia lactativora, Sporopachydermia quercuum, Torulaspora delbrueckii, Torulaspora franciscae, Torulaspora globosa, Torulaspora pretoriensis, Yarrowia lipolytica, Zygosaccharomyces bailii, Zygosaccharomyces bisporus, Zygosaccharomyces cidri, Zygosaccharomyces fermentati, Zygosaccharomyces florentinus, Zygosaccharomyces kombuchaensis, Zygosaccharomyces lentus, Zygosaccharomyces mellis, Zygosaccharomyces microellipsoides, Zygosaccharomyces mrakii, Zygosaccharomyces pseudorouxii,* or *Zygosaccharomyces rouxii,* or a variant or genetically modified version thereof.

Examples of bacteria that can be used as a biocatalyst or fermentive microorganism in the methods disclosed herein include but are not limited to any bacterium found in the genus of *Butyrivibrio, Ruminococcus, Eubacterium, Bacteroides, Acetivibrio, Caldibacillus, Acidothermus, Cellulomonas, Curtobacterium, Micromonospora, Actinoplanes, Streptomyces, Thermobifida, Thermomonospora, Microbispora, Fibrobacter, Sporocytophaga, Cytophaga, Flavobacterium, Achromobacter, Xanthomonas, Cellvibrio, Pseudomonas, Myxobacter, Escherichia, Klebsiella, Thermoanaerobacterium, Thermoanaerobacter, Geobacillus, Saccharococcus, Paenibacillus, Bacillus, Caldicellulosiruptor, Anaerocellum, Anoxybacillus, Zymomonas, Clostridium;* for example, *Butyrivibrio fibrisolvens, Ruminococcus flavefaciens, Ruminococcus succinogenes, Ruminococcus albus, Eubacterium cellulolyticum, Bacteroides cellulosolvens, Acetivibrio cellulolyticus, Acetivibrio cellulosolvens, Caldibacillus cellulovorans, Bacillus circulans, Acidothermus cellulolyticus, Cellulomonas cartae, Cellulomonas cellasea, Cellulomonas cellulans, Cellulomonas fimi, Cellulomonas flavigena, Cellulomonas gelida, Cellulomonas iranensis, Cellulomonas persica, Cellulomonas uda, Curtobacterium falcumfaciens, Micromonospora melonosporea, Actinoplanes aurantiaca, Streptomyces reticuli, Streptomyces alboguseolus, Streptomyces aureofaciens, Streptomyces cellulolyticus, Streptomyces fiavogriseus, Streptomyces lividans, Streptomyces nitrosporeus, Streptomyces olivochromogenes, Streptomyces rochei, Streptomyces thermovulgaris, Streptomyces viridosporus, Thermobifida alba, Thermobifida fusca, Thermobifida cellulolytica, Thermomonospora curvata, Microbispora bispora, Fibrobacter succinogenes, Sporocytophaga myxococcoides, Cytophaga sp., Flavobacterium johnsoniae, Achromobacter piechaudii, Xanthomonas sp., Cellvibrio vulgaris, Cellvibrio fulvus, Cellvibrio gilvus, Cellvibrio mixtus, Pseudomonas fiuorescens, Pseudomonas mendocina, Myxobacter sp. AL-1, Escherichia albertii, Escherichia blattae, Escherichia coli, Escherichia fergusonii, Escherichia hermannii, Escherichia vulneris, Klebsiella granulomatis, Klebsiella oxytoca, Klebsiella pneumonia, Klebsiella terrigena, Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brocki, Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchatkensis, Anoxybacillus gonensis, Caldicellulosiruptor acetigenus, Caldicellulosiruptor saccharolyticus, Caldicellulosiruptor kristjanssonii, Caldicellulosiruptor owensensis, Caldicellulosiruptor lactoaceticus, Anaerocellum thermophilum, Clostridium thermocellum, Clostridium cellulolyticum, Clostridium straminosolvens, Clostridium acetobutylicum, Clostridium aerotolerans, Clostridium beijerinckii, Clostridium bifermentans, Clostridium botulinum, Clostridium butyricum, Clostridium cadaveric, Clostridium chauvoei, Clostridium clostridioforme, Clostridium colicanis, Clostridium difficile, Clostridium fallax, Clostridium formicaceticum, Clostridium histolyticum, Clostridium innocuum, Clostridium ljungdahlii, Clostridium laramie, Clostridium lavalense, Clostridium novyi, Clostridium oedematiens, Clostridium paraputrificum, Clostridium perfringens, Clostridium phytofermentans, Clostridium piliforme, Clostridium ramosum, Clostridium scatologenes, Clostridium septicum, Clostridium sordellii, Clostridium sporogenes, Clostridium tertium, Clostridium tetani, Clostridium tyrobutyricum, Clostridium thermobutyricum, Zymomonas mobilis,* or a variant or genetically modified version thereof.

In one embodiment, fed-batch fermentation is performed on the treated biomass to produce a fermentation end-product, such as alcohol, ethanol, organic acid, succinic acid, TAG, or hydrogen. In one embodiment, the fermentation process comprises simultaneous hydrolysis and fermentation (SSF) of the biomass using one or more microorganisms such as a *Rhodococcus* strain, a *Clostridium* strain, a *Trichoderma* strain, a *Saccharomyces* strain, a *Zymomonas* strain, or another microorganism suitable for fermentation of biomass. In another embodiment, the fermentation process comprises simultaneous hydrolysis and fermentation of the biomass using a microorganism that is *Clostridium algidixylanolyticum, Clostridium xylanolyticum, Clostridium cellulovorans, Clostridium cellulolyticum, Clostridium thermocellum, Clostridium josui, Clostridium papyrosolvens, Clostridium cellobioparum, Clostridium hungatei, Clostridium cellulosi,*

*Clostridium stercorarium, Clostridium termitidis, Clostridium thermocopriae, Clostridium celerecrescens, Clostridium polysaccharolyticum, Clostridium populeti, Clostridium lentocellum, Clostridium chartatabidum, Clostridium aldrichii, Clostridium herbivorans, Clostridium phytofermentans, Acetivibrio cellulolyticus, Bacteroides cellulosolvens, Caldicellulosiruptor saccharolyticum, Ruminococcus albus, Ruminococcus flavefaciens, Fibrobacter succinogenes, Eubacterium cellulosolvens, Butyrivibrio fibrisolvens, Anaerocellum thermophilum, Halocella cellulolytica, Thermoanaerobacterium thermosaccharolyticum, Sacharophagus degradans, or Thermoanaerobacterium saccharolyticum.*

In one embodiment, the fermentation process can include separate hydrolysis and fermentation (SHF) of a biomass with one or more enzymes, such as a xylanases, endo-1,4-beta-xylanases, xylosidases, beta-D-xylosidases, cellulases, hemicellulases, carbohydrases, glucanases, endoglucanases, endo-1,4-beta-glucanases, exoglucanases, glucosidases, beta-D-glucosidases, amylases, cellobiohydrolases, exocellobiohydrolases, phytases, proteases, peroxidase, pectate lyases, galacturonases, or laccases. In one embodiment, one or more enzymes used to treat a biomass is thermostable. In another embodiment, a biomass is treated with one or more enzymes, such as those provided herein, prior to fermentation. In another embodiment, a biomass is treated with one or more enzymes, such as those provided herein, during fermentation. In another embodiment, a biomass is treated with one or more enzymes, such as those provided herein, prior to fermentation and during fermentation. In another embodiment, an enzyme used for hydrolysis of a biomass is the same as those added during fermentation. In another embodiment, an enzyme used for hydrolysis of biomass is different from those added during fermentation.

In some embodiments, fermentation can be performed in an apparatus such as bioreactor, a fermentation vessel, a stirred tank reactor, or a fluidized bed reactor. In one embodiment, the treated biomass can be supplemented with suitable chemicals to facilitate robust growth of the one or more fermenting organisms. In one embodiment, a useful supplement includes but is not limited to, a source of nitrogen and/or amino acids such as yeast extract, cysteine, or ammonium salts (e.g. nitrate, sulfate, phosphate etc.); a source of simple carbohydrates such as corn steep liquor, and malt syrup; a source of vitamins such as yeast extract; buffering agents such as salts (including but not limited to citrate salts, phosphate salts, or carbonate salts); or mineral nutrients such as salts of magnesium, calcium, or iron. In some embodiments redox modifiers are added to the fermentation mixture including but not limited to cysteine or mercaptoethanol.

In one embodiment, the titer and/or productivity of fermentation end-product production by a microorganism is improved by culturing the microorganism in a medium comprising one or more compounds comprising hexose and/or pentose sugars. In one embodiment, a process comprises conversion of a starting material (such as a biomass) to a biofuel, such as one or more alcohols. In one embodiment, methods can comprise contacting substrate comprising both hexose (e.g. glucose, cellobiose) and pentose (e.g. xylose, arabinose) saccharides with a microorganism that can hydrolyze C5 and C6 saccharides to produce ethanol. In another embodiment, methods can comprise contacting substrate comprising both hexose (e.g. glucose, cellobiose) and pentose (e.g. xylose, arabinose) saccharides with *R. opacus* to produce TAG.

In some embodiments, batch fermentation with a microorganism of a mixture of hexose and pentose saccharides using the methods disclosed herein can provide uptake rates of about 0.1-8 g/L/h or more of hexose and about 0.1-8 g/L/h or more of pentose (xylose, arabinose, etc.). In some embodiments, batch fermentation with a microorganism of a mixture of hexose and pentose saccharides using the methods disclosed herein can provide uptake rates of about 0.1, 0.2, 0.4, 0.5, 0.6.0.7, 0.8, 1, 2, 3, 4, 5, or 6 g/L/h or more of hexose and about 0.1, 0.2, 0.4, 0.5, 0.6.0.7, 0.8, 1, 2, 3, 4, 5, or 6 g/L/h or more of pentose.

In one embodiment, a method for production of ethanol or another alcohol produces about 10 g/l to 120 g ain 40 hours or less. In another embodiment, a method for production of ethanol produces about 10 g/l, 11 g/L, 12 g/L, 13 g/L, 14 g/L, 15 g/L, 16 g/L, 17 g/L, 18 g/L, 19 g/L, 20 g/L, 21 g/L, 22 g/L, 23 g/L, 24 g/L, 25 g/L, 26 g/L, 27 g/L, 28 g/L, 29 g/L, 30 g/L, 31 g/L, 32 g/L, 33 g/L, 34 g/L, 35 g/L, 36 g/L, 37 g/L, 38 g/L, 39 g/L, 40 g/L, 41 g/L, 42 g/L, 43 g/L, 44 g/L, 45 g/L, 46 g/L, 47 g/L, 48 g/L, 49 g/L, 50 g/L, 51 g/L, 52 g/L, 53 g/L, 54 g/L, 55 g/L, 56 g/L, 57 g/L, 58 g/L, 59 g/L, 60 g/L, 61 g/L, 62 g/L, 63 g/L, 64 g/L, 65 g/L, 66 g/L, 67 g/L, 68 g/L, 69 g/L, 70 g/L, 71 g/L, 72 g/L, 73 g/L, 74 g/L, 75 g/L, 76 g/L, 77 g/L, 78 g/L, 79 g/L, 80 g/L, 81 g/L, 82 g/L, 83 g/L, 84 g/L, 85 g/L, 86 g/L, 87 g/L, 88 g/L, 89 g/L, 90 g/L, 91 g/L, 92 g/L, 93 g/L, 94 g/L, 95 g/L, 96 g/L, 97 g/L, 98 g/L, 99 g/L, 100 g/L, 110 g/l, 120 g/l, or more alcohol in 40 hours by the fermentation of biomass. In another embodiment, alcohol is produced by a method comprising simultaneous fermentation of hexose and pentose saccharides. In another embodiment, alcohol is produced by a microorganism comprising simultaneous fermentation of hexose and pentose saccharides.

In another embodiment, the level of a medium component is maintained at a desired level by adding additional medium component as the component is consumed or taken up by the organism. Examples of medium components included, but are not limited to, carbon substrate, nitrogen substrate, vitamins, minerals, growth factors, cofactors, and biocatalysts. The medium component can be added continuously or at regular or irregular intervals. In one embodiment, additional medium component is added prior to the complete depletion of the medium component in the medium. In one embodiment, complete depletion can effectively be used, for example to initiate different metabolic pathways, to simplify downstream operations, or for other reasons as well. In one embodiment, the medium component level is allowed to vary by about 10% around a midpoint, in one embodiment, it is allowed to vary by about 30% around a midpoint, and in one embodiment, it is allowed to vary by 60% or more around a midpoint. In one embodiment, the medium component level is maintained by allowing the medium component to be depleted to an appropriate level, followed by increasing the medium component level to another appropriate level. In one embodiment, a medium component, such as vitamin, is added at two different time points during fermentation process. For example, one-half of a total amount of vitamin is added at the beginning of fermentation and the other half is added at midpoint of fermentation.

In another embodiment, the nitrogen level is maintained at a desired level by adding additional nitrogen-containing material as nitrogen is consumed or taken up by the organism. The nitrogen-containing material can be added continuously or at regular or irregular intervals. Useful nitrogen levels include levels of about 5 to about 10 g/L. In one embodiment, levels of about 1 to about 12 g/L can also be usefully employed. In another embodiment, levels, such as about 0.5, 0.1 g/L or even lower, and higher levels, such as about 20, 30 g/L or even higher are used. In another embodiment, a useful nitrogen level is about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22 23, 24, 25, 26, 27, 28, 29 or 30 g/L. Nitrogen can be supplied as a simple nitrogen-containing material, such as an ammonium compounds (e.g. ammonium sulfate, ammonium hydroxide, ammonia, ammonium nitrate, or any other compound or mixture containing an ammonium moiety), nitrate or nitrite compounds (e.g. potassium, sodium, ammonium, calcium, or other compound or mixture containing a nitrate or nitrite moiety), or as a more complex nitrogen-containing material, such as amino acids, proteins, hydrolyzed protein, hydrolyzed yeast, yeast extract, dried brewer's yeast, yeast hydrolysates, distillers' grains, soy protein, hydrolyzed soy protein, fermentation products, and processed or corn steep powder or unprocessed protein-rich vegetable or animal matter, including those derived from bean, seeds, soy, legumes, nuts, milk, pig, cattle, mammal, fish, as well as other parts of plants and other types of animals. Nitrogen-containing materials useful in various embodiments also include materials that contain a nitrogen-containing material, including, but not limited to mixtures of a simple or more complex nitrogen-containing material mixed with a carbon source, another nitrogen-containing material, or other nutrients or non-nutrients, and AFEX treated plant matter.

In another embodiment, the carbon level is maintained at a desired level by adding sugar compounds or material containing sugar compounds ("Sugar-Containing Material") as sugar is consumed or taken up by the organism. The sugar-containing material can be added continuously or at regular or irregular intervals. In one embodiment, additional sugar-containing material is added prior to the complete depletion of the sugar compounds available in the medium. In one embodiment, complete depletion can effectively be used, for example to initiate different metabolic pathways, to simplify downstream operations, or for other reasons as well. In one embodiment, the carbon level (as measured by the grams of sugar present in the sugar-containing material per liter of broth) is allowed to vary by about 10% around a midpoint, in one embodiment, it is allowed to vary by about 30% around a midpoint, and in one embodiment, it is allowed to vary by 60% or more around a midpoint. In one embodiment, the carbon level is maintained by allowing the carbon to be depleted to an appropriate level, followed by increasing the carbon level to another appropriate level. In some embodiments, the carbon level can be maintained at a level of about 5 to about 120 g/L. However, levels of about 30 to about 100 g/L can also be usefully employed as well as levels of about 60 to about 80 g/L. In one embodiment, the carbon level is maintained at greater than 25 g/L for a portion of the culturing. In another embodiment, the carbon level is maintained at about 5 g/L, 6 g/L, 7 g/L, 8 g/L, 9 g/L, 10 g/L, 11 g/L, 12 g/L, 13 g/L, 14 g/L, 15 g/L, 16 g/L, 17 g/L, 18 g/L, 19 g/L, 20 g/L, 21 g/L, 22 g/L, 23 g/L, 24 g/L, 25 g/L, 26 g/L, 27 g/L, 28 g/L, 29 g/L, 30 g/L, 31 g/L, 32 g/L, 33 g/L, 34 g/L, 35 g/L, 36 g/L, 37 g/L, 38 g/L, 39 g/L, 40 g/L, 41 g/L, 42 g/L, 43 g/L, 44 g/L, 45 g/L, 46 g/L, 47 g/L, 48 g/L, 49 g/L, 50 g/L, 51 g/L, 52 g/L, 53 g/L, 54 g/L, 55 g/L, 56 g/L, 57 g/L, 58 g/L, 59 g/L, 60 g/L, 61 g/L, 62 g/L, 63 g/L, 64 g/L, 65 g/L, 66 g/L, 67 g/L, 68 g/L, 69 g/L, 70 g/L, 71 g/L, 72 g/L, 73 g/L, 74 g/L, 75 g/L, 76 g/L, 77 g/L, 78 g/L, 79 g/L, 80 g/L, 81 g/L, 82 g/L, 83 g/L, 84 g/L, 85 g/L, 86 g/L, 87 g/L, 88 g/L, 89 g/L, 90 g/L, 91 g/L, 92 g/L, 93 g/L, 94 g/L, 95 g/L, 96 g/L, 97 g/L, 98 g/L, 99 g/L, 100 g/L, 101 g/L, 102 g/L, 103 g/L, 104 g/L, 105 g/L, 106 g/L, 107 g/L, 108 g/L, 109 g/L, 110 g/L, 111 g/L, 112 g/L, 113 g/L, 114 g/L, 115 g/L, 116 g/L, 117 g/L, 118 g/L, 119 g/L, 120 g/L, 121 g/L, 122 g/L, 123 g/L, 124 g/L, 125 g/L, 126 g/L, 127 g/L, 128 g/L, 129 g/L, 130 g/L, 131 g/L, 132 g/L, 133 g/L, 134 g/L, 135 g/L, 136 g/L, 137 g/L, 138 g/L, 139 g/L, 140 g/L, 141 g/L, 142 g/L, 143 g/L, 144 g/L, 145 g/L, 146 g/L, 147 g/L, 148 g/L, 149 g/L, or 150 g/L.

The carbon substrate, like the nitrogen substrate, can be used for cell production and enzyme production, but unlike the nitrogen substrate, the carbon substrate can serve as the raw material for production of fermentation end-products. Frequently, more carbon substrate can lead to greater production of fermentation end-products. In another embodiment, it can be advantageous to operate with the carbon level and nitrogen level related to each other for at least a portion of the fermentation time. In one embodiment, the ratio of carbon to nitrogen is maintained within a range of about 30:1 to about 10:1. In another embodiment, the ratio of carbon nitrogen is maintained from about 20:1 to about 10:1 or more preferably from about 15:1 to about 10:1. In another embodiment, the ratio of carbon nitrogen is about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, or 1:1.

Maintaining the ratio of carbon and nitrogen ratio within particular ranges can result in benefits to the operation such as the rate of metabolism of carbon substrate, which depends on the amount of carbon substrate and the amount and activity of enzymes present, being balanced to the rate of end product production. Balancing the carbon to nitrogen ratio can, for example, facilitate the sustained production of these enzymes such as to replace those which have lost activity.

In another embodiment, the amount and/or timing of carbon, nitrogen, or other medium component addition can be related to measurements taken during the fermentation. For example, the amount of monosaccharides present, the amount of insoluble polysaccharide present, the polysaccharase activity, the amount of product present, the amount of cellular material (for example, packed cell volume, dry cell weight, etc.) and/or the amount of nitrogen (for example, nitrate, nitrite, ammonia, urea, proteins, amino acids, etc.) present can be measured. The concentration of the particular species, the total amount of the species present in the fermentor, the number of hours the fermentation has been running, and the volume of the fermentor can be considered. In various embodiments, these measurements can be compared to each other and/or they can be compared to previous measurements of the same parameter previously taken from the same fermentation or another fermentation. Adjustments to the amount of a medium component can be accomplished such as by changing the flow rate of a stream containing that component or by changing the frequency of the additions for that component. For example, the amount of saccharide can be increased when the cell production increases faster than the end product production. In another embodiment, the amount of nitrogen can be increased when the enzyme activity level decreases.

In another embodiment, a fed batch operation can be employed, wherein medium components and/or fresh cells are added during the fermentation without removal of a portion of the broth for harvest prior to the end of the fermentation. In one embodiment, a fed-batch process is based on feeding a growth limiting nutrient medium to a culture of microorganisms. In one embodiment, the feed medium is highly concentrated to avoid dilution of the bioreactor. In another embodiment, the controlled addition of the nutrient directly affects the growth rate of the culture and avoids overflow metabolism such as the formation of side metabolites. In one embodiment, the growth limiting nutrient is a nitrogen source or a saccharide source.

In various embodiments, particular medium components can have beneficial effects on the performance of the fermentation, such as increasing the titer of desired products, or increasing the rate that the desired products are produced. Specific compounds can be supplied as a specific, pure ingredient, such as a particular amino acid, or it can be supplied as a component of a more complex ingredient, such as using a microbial, plant or animal product as a medium ingredient to provide a particular amino acid, promoter, cofactor, or other beneficial compound. In some cases, the particular compound supplied in the medium ingredient can be combined with other compounds by the organism resulting in a fermentation-beneficial compound. One example of this situation would be where a medium ingredient provides a specific amino acid which the organism uses to make an enzyme beneficial to the fermentation. Other examples can include medium components that are used to generate growth or product promoters, etc. In such cases, it can be possible to obtain a fermentation-beneficial result by supplementing the enzyme, promoter, growth factor, etc. or by adding the precursor. In some situations, the specific mechanism whereby the medium component benefits the fermentation is not known, only that a beneficial result is achieved.

In one embodiment, a fermentation to produce a fuel is performed by culturing a strain of R. opacus in a medium having a supplement of lignin component and a concentration of one or more carbon sources. The resulting production of end product such as TAG can be up to 1-fold, 2-fold, 3-fold, 4-fold, 5-fold, 6-fold, 7-fold, 8-fold, 9-fold, and in some cases up to 10-fold and higher in volumetric productivity than a process using only the addition of a relatively pure saccharide source, and can achieve a carbon conversion efficiency approaching the theoretical maximum. The theoretical maximum can vary with the substrate and product. For example, the generally accepted maximum efficiency for conversion of glucose to ethanol is 0.51 g ethanol/g glucose. In one embodiment, a biocatalyst can produce about 40-100% of a theoretical maximum yield of ethanol. In another embodiment, a biocatalyst can produce up to about 40%, 50%, 60%, 70%, 80%, 90%, 95% and even 100% of the theoretical maximum yield of ethanol. In one embodiment, a biocatalyst can produce up to about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.99%, or 100% of a theoretical maximum yield of a fuel. It can be possible to obtain a fermentation-beneficial result by supplementing the medium with a pretreatment or hydrolysis component. In some situations, the specific mechanism whereby the medium component benefits the fermentation is not known, only that a beneficial result is achieved.

Various embodiments offer benefits relating to improving the titer and/or productivity of fermentation end-product production by a biocatalyst by culturing the organism in a medium comprising one or more compounds comprising particular fatty acid moieties and/or culturing the organism under conditions of controlled pH.

In one embodiment, the pH of the medium is controlled at less than about pH 7.2 for at least a portion of the fermentation. In one embodiment, the pH is controlled within a range of about pH 3.0 to about 7.1 or about pH 4.5 to about 7.1, or about pH 5.0 to about 6.3, or about pH 5.5 to about 6.3, or about pH 6.0 to about 6.5, or about pH 5.5 to about 6.9 or about pH 6.2 to about 6.7. The pH can be controlled by the addition of a pH modifier. In one embodiment, a pH modifier is an acid, a base, a buffer, or a material that reacts with other materials present to serve to raise of lower the pH. In one embodiment, more than one pH modifier can be used, such as more than one acid, more than one base, one or more acid with one or more bases, one or more acids with one or more buffers, one or more bases with one or more buffers, or one or more acids with one or more bases with one or more buffers. When more than one pH modifiers are utilized, they can be added at the same time or at different times. In one embodiment, one or more acids and one or more bases can be combined, resulting in a buffer. In one embodiment, media components, such as a carbon source or a nitrogen source can also serve as a pH modifier; suitable media components include those with high or low pH or those with buffering capacity. Exemplary media components include acid- or base-hydrolyzed plant polysaccharides having with residual acid or base, AFEX treated plant material with residual ammonia, lactic acid, corn steep solids or liquor.

In one embodiment, a constant pH can be utilized throughout the fermentation. In one embodiment, the timing and/or amount of pH reduction can be related to the growth conditions of the cells, such as in relation to the cell count, the end product produced, the end product present, or the rate of end product production. In one embodiment, the pH reduction can be made in relation to physical or chemical properties of the fermentation, such as viscosity, medium composition, gas production, off gas composition, etc.

Recovery of Fermentation End Products

In another aspect, methods are provided for the recovery of the fermentive end products, such as an alcohol (e.g. ethanol, propanol, methanol, butanol, etc.) another biofuel or chemical product. In one embodiment, broth will be harvested at some point during of the fermentation, and fermentive end product or products will be recovered. The broth with end product to be recovered will include both end product and impurities. The impurities include materials such as water, cell bodies, cellular debris, excess carbon substrate, excess nitrogen substrate, other remaining nutrients, other metabolites, and other medium components or digested medium components. During the course of processing the broth, the broth can be heated and/or reacted with various reagents, resulting in additional impurities in the broth.

In one embodiment, the processing steps to recover end product frequently includes several separation steps, including, for example, distillation of a high concentration alcohol material from a less pure alcohol-containing material. In one embodiment, the high concentration alcohol material can be further concentrated to achieve very high concentration alcohol, such as 98% or 99% or 99.5% (wt.) or even higher. Other separation steps, such as filtration, centrifugation, extraction, adsorption, etc. can also be a part of some recovery processes for alcohol as a product or biofuel, or other biofuels or chemical products.

In one embodiment, a process can be scaled to produce commercially useful biofuels. In another embodiment, biocatalyst is used to produce an alcohol, e.g., ethanol, butanol, propanol, methanol, or a fuel such as hydrocarbons hydrogen, TAG, and hydroxy compounds. In another embodiment, biocatalyst is used to produce a carbonyl compound such as an aldehyde or ketone (e.g. acetone, formaldehyde, 1-propanal, etc.), an organic acid, a derivative of an organic acid such as an ester (e.g. wax ester, glyceride, etc.), 1,2-propanediol, 1,3-propanediol, lactic acid, formic acid, acetic acid, succinic acid, pyruvic acid, or an enzyme such as a cellulase, polysaccharase, lipases, protease, ligninase, and hemicellulase.

In one embodiment, useful biochemicals can be produced from non-food plant biomass, with a steam or hot-water extraction technique that is carried out by contacting a charge of non-food plant pretreated biomass material such as corn stover or sorghum with water and/or acid (with or without additional process enhancing compounds or materials), in a pressurized vessel at an elevated temperature up to about 160-220° C. and at a pH below about 7.0, to yield an aqueous (extract solution) mixture of useful sugars including long-chain saccharides (sugars), acetic acid, and lignin, while leaving the structural (cellulose and lignin) portion of the lignocellulosic material largely intact. In combination, these potential inhibitory chemicals especially sugar degradation products are low, and the plant derived nutrients that are naturally occurring lignocellulosic-based components are also recovered that are beneficial to a C5 and/or C6 fermenting organism. Toward this objective, the aqueous extract is concentrated (by centrifugation, filtration, solvent extraction, flocculation, evaporation), by producing a concentrated sugar stream, apart from the other hemicellulose (C5 rich) and cellulosic derived sugars (C6 rich) which are channeled into a fermentable stream.

Biofuel Plant and Process of Producing Biofuel:

Large Scale Fuel and Chemical Production from Biomass

Generally, there are several basic approaches to producing fuels and chemical end-products from biomass on a large scale utilizing of microbial cells. In the one method, one first pretreats and hydrolyzes a biomass material that includes high molecular weight carbohydrates to lower molecular weight carbohydrates, and then ferments the lower molecular weight carbohydrates utilizing of microbial cells to produce fuel or other products. In the second method, one treats the biomass material itself using mechanical, chemical and/or enzymatic methods. In all methods, depending on the type of biomass and its physical manifestation, one of the processes can comprise a milling of the carbonaceous material, via wet or dry milling, to reduce the material in size and increase the surface to volume ratio (physical modification).

In one embodiment, hydrolysis can be accomplished using acids, e.g., Bronsted acids (e.g., sulfuric or hydrochloric acid), bases, e.g., sodium hydroxide, hydrothermal processes, ammonia fiber explosion processes ("AFEX"), lime processes, enzymes, or combination of these. Hydrogen, and other end products of the fermentation can be captured and purified if desired, or disposed of, e.g., by burning. For example, the hydrogen gas can be flared, or used as an energy source in the process, e.g., to drive a steam boiler, e.g., by burning. Hydrolysis and/or steam treatment of the biomass can, e.g., increase porosity and/or surface area of the biomass, often leaving the cellulosic materials more exposed to the biocatalyst cells, which can increase fermentation rate and yield. Removal of lignin can, e.g., provide a combustible fuel for driving a boiler, and can also, e.g., increase porosity and/or surface area of the biomass, often increasing fermentation rate and yield. Generally, in any of the these embodiments, the initial concentration of the carbohydrates in the medium is greater than 20 mM, e.g., greater than 30 mM, 50 mM, 75 mM, 100 mM, 150 mM, 200 mM, or even greater than 500 mM.

Biomass Processing Plant and Process of Producing Products from Biomass

In one aspect, a fuel or chemical plant that includes a pretreatment unit to prepare biomass for improved exposure and biopolymer separation, a hydrolysis unit configured to hydrolyze a biomass material that includes a high molecular weight carbohydrate, and one or more product recovery system(s) to isolate a product or products and associated by-products and co-products is provided. In another aspect, methods of purifying lower molecular weight carbohydrate from solid byproducts and/or toxic impurities is provided.

In another aspect, methods of making a product or products that include combining biocatalyst cells of a microorganism and a biomass feed in a medium wherein the biomass feed contains lower molecular weight carbohydrates and unseparated solids and/or other liquids from pretreatment and hydrolysis, and fermenting the biomass material under conditions and for a time sufficient to produce a biofuel, chemical product or fermentive end-products, e.g. ethanol, propanol, hydrogen, succinic acid, lignin, terpenoids, and the like as described above, is provided.

In another aspect, products made by any of the processes described herein is also provided herein.

One example is a method for producing chemical products from biomass by first treating biomass with an acid at elevated temperature and pressure in a hydrolysis unit. The biomass may first be heated by addition of hot water or steam. The biomass may be acidified by bubbling gaseous sulfur dioxide through the biomass that is suspended in water, or by adding a strong acid, e.g., sulfuric, hydrochloric, or nitric acid with or without preheating/presteaming/water addition. During the acidification, the pH is maintained at a low level, e.g., below about 5. The temperature and pressure may be elevated after acid addition. In addition to the acid already in the acidification unit, optionally, a metal salt such as ferrous sulfate, ferric sulfate, ferric chloride, aluminum sulfate, aluminum chloride, magnesium sulfate, or mixtures of these can be added to aid in the acid hydrolysis of the biomass. The acid-impregnated biomass is fed into the hydrolysis section of the pretreatment unit. Steam is injected into the hydrolysis portion of the pretreatment unit to directly contact and heat the biomass to the desired temperature. The temperature of the biomass after steam addition is, e.g., between about 130° C. and 220° C. The acid hydrolysate is then discharged into the flash tank portion of the pretreatment unit, and is held in the tank for a period of time to further hydrolyze the biomass, e.g., into oligosaccharides and monomeric sugars. Other methods can also be used to further break down biomass. Alternatively, the biomass can be subject to discharge through a pressure lock for any high-pressure pretreatment process. Hydrolysate is then discharged from the pretreatment reactor, with or without the addition of water, e.g., at solids concentrations between about 10% and 60%.

After pretreatment, the biomass may be dewatered and/or washed with a quantity of water, e.g. by squeezing or by centrifugation, or by filtration using, e.g. a countercurrent extractor, wash press, filter press, pressure filter, a screw conveyor extractor, or a vacuum belt extractor to remove acidified fluid. Wash fluids can be collected to concentrate the C5 saccharides in the wash stream. The acidified fluid, with or without further treatment, e.g. addition of alkali (e.g. lime) and or ammonia (e.g. ammonium phosphate), can be re-used, e.g., in the acidification portion of the pretreatment unit, or added to the fermentation, or collected for other use/treatment. Products may be derived from treatment of the acidified fluid, e.g., gypsum or ammonium phosphate. Enzymes or a mixture of enzymes can be added during pretreatment to hydrolyze, e.g. endoglucanases, exoglucanases, cellobiohydrolases (CBH), beta-glucosidases, glycoside hydrolases, glycosyltransferases, alphyamylases, chitinases, pectinases, lyases, and esterases active against components of cellulose, hemicelluloses, pectin, and starch, in the hydrolysis of high molecular weight components.

A fermentor, attached or at a separate site, can be fed with hydrolyzed biomass, any liquid fraction from biomass pretreatment, an active seed culture of a biocatalyst, such as a yeast, if desired a co-fermenting microbe, e.g., another yeast or E. coli, and, if required, nutrients to promote growth of the biocatalyst or other microbes. Alternatively, the pretreated biomass or liquid fraction can be split into multiple fermentors, each containing a different strain of a biocatalyst and/or other microbes, and each operating under specific physical conditions. Fermentation is allowed to proceed for a period of time, e.g., between about 1 and 150 hours, while maintaining a temperature of, e.g., between about 25° C. and 50° C. Gas produced during the fermentation is swept from fermentor and is discharged, collected, or flared with or without additional processing, e.g. hydrogen gas may be collected and used as a power source or purified as a co-product.

In another aspect, methods of making a fuel or fuels that include combining one or more biocatalyst and a lignocellulosic material (and/or other biomass material) in a medium, adding a lignin fraction from pretreatment, and fermenting the lignocellulosic material under conditions and for a time sufficient to produce a fuel or fuels, e.g., ethanol, propanol and/or hydrogen or another chemical compound is provided herein.

In another aspect, the products made by any of the processes described herein is provided.

EXAMPLES

The following examples serve to illustrate certain embodiments and aspects and are not to be construed as limiting the scope thereof.

Example 1

Maintenance of DDGS Levels

To supplement C6 with corn mash, a 20% C6 solution is added to an 80% corn mash for an SSF fermentation. The 80% corn mash slurry contains 30% solids which are comprised of 72% starch, 12-15% glucan, oil and fiber about 7-10%. The oil and fiber, after the fermentation of the starch and glucan, constitutes what is called DDGS and can be sold as feed, primarily for cattle. The starch fermentation results in 21-22% sugars which can be converted to 10-11% ethanol.

If starch-derived sugar is blended with 26-30% C6 concentration in the ratio described supra (20:80), and then fermented, there can be an increase in sugar yields. The totals are 25-26% sugar which translates into a 12-13% ethanol yield. However, 20% of the DDGS can be lost due to the dilution of the corn mash solids. The ethanol yield can be increased but there can be a loss of income from the DDGS yield.

The solution is to add a greater concentration of the solids (36% solids instead of 30% solids) to the 80% corn mash solution. Corn mash cannot normally be fermented at a high solids content (36%). However, because the solids are diluted in a C6-supplemented fermentation, DDGS yields can be maintained. Thus, in a 1000 gallon tank, 800 gallons of corn mash containing 36% solids can be supplemented with 200 gallons of C6 solution containing 26-30% C6 sugar, to prevent loss of DDGS. The corn mash solution, that cannot be fermented as 36% solids can be diluted to 30% solids. Thus there can be an increase of ethanol yield (or sugar yield) and production of the same amount of DDGS. The 3-4% increase in sugar can lead to a 1-2% increase in ethanol Example 2

Preparation of Cellulosic-Derived C6 Fermentable Sugars (from Sorghum and Switchgrass)

Non-food cellulosic feedstock is received and pre-processed. First, oversized materials (example large chunks of wood) and contaminates (for example stones, soil, etc.) are selected and removed in a gross screening process. The undersized particles, or fines, including contaminates, such as sand, soil or the like, are separated and removed in a fine screening process. The remaining lignocellulosic material can be triturated (e.g., by chipping, tub grinding, hammer milling, or other available comminuting procedure) to reduce the feedstock to the preferred size and condition for further handling and processing.

In one example, switch grass and ensiled energy sorghum was used. Switch grass was dried and hammer milled to reduce particle size. In the case of ensiled energy sorghum, the material was chopped and ensiled in a bunker. The water content of each biomass feedstock was determined and adjusted to a solids content of about 15% (wt/v) solids and moisture content of about 85% (wt/v) using a 24 hour soaking treatment.

The moisture-adjusted switch grass and energy sorghum feedstocks were separately prepared for an acid-catalyzed steam explosion pretreatment process by impregnating the feedstocks with 1% $H_2SO_4$ (w/w, based on dry weight) and left to soak overnight. The impregnated raw material was then charged to a 60 L pressurized steam explosion batch reactor at a temperature of about 200° C. and a pH of about 2.9 for 7.5 min, so that an aqueous extract (or liquor) containing solubilized components of the lignocellulosic material was obtained (C5 rich). The remaining lignocellulosic material (e.g., fibrous material) was separated from the liquor or extract, and each was further processed as discussed infra.

Upon completion of pretreatment, the post-treated material, comprising about 12% to about 14% solids [wt/v], was subjected to a water washing step to separate solubilized C5 sugar from C6 sugars. The washing was performed in two steps; in the first step, the post-treated feedstock was separated by centrifugation filter press which enables the separation of the solids from the liquid stream (the liquid stream being C5 rich, e.g., containing a high proportion of C5 sugars). The solid material was further suspended in water to recover additional C5 sugar that may have remained in the separated solids portion. On removing the soluble hemicellulose sugars, the remaining solids contained the cellulose or hexose rich C6 sugars. However, as a person of skill appreciates, no separation process is perfect and the solids portion may include some amount of C5 sugars, and the liquid stream may include some amount of C6 sugars. The liquid stream was then retained and maintained separate from the C6 stream. The separated solids were placed into a mixing tank. Once inside the mixing tank, the solids were adjusted to a pH of about 5 using 0.1N NaOH. The solids wee then diluted to a dry solids content of about 8% solids. Enzymes (CELLIC CTech 2, Novozymes North America, Franklinton, N.C.) were added to the solid slurry at 2% loading (v/wt) based on the dry weight of the solids.

FIG. 1 is a sample sugar trajectory that illustrates how the biomass is converted from solids into liquefied stream of C6 sugars. FIG. 1 was generated by collecting samples periodically for estimation (by HPLC) of cellulosic C6 sugars released by enzymatic hydrolysis of solids. Once enzymatic hydrolysis was complete, the liquid slurry is separated by centrifugation or microfiltration; or, alternatively, the solids can remain in the broth. For the experiments herein, the solids were separated from the broth using evaporation. Approximately 30 L of the resultant C6-rich liquid slurry was concentrated by simple evaporation at a temperature of from about 70° C. to about 80° C. until the sugar content of the sorghum or switchgrass hydrolysate was raised from about 5% to about 20% w/v. The resulting composition had a C6 sugar:C5 sugar ratio of about 90:10.

Example 3

Preparation and Fermentation of Corn Mash Glucose Feedstock

Mash was derived from industrial dry milling operations (Western New York Energy). Large debris were removed from the standard corn by hand, and small debris (<4 mm) were removed by passing through a No. 5 sieve before grinding using a Wiley mill fitted with a 2-mm screen. This produced particles of which 95% were smaller than 1.5 mm. The moisture content of the ground corn was 13.98% (w/w, as received) and was used to determine the mass of corn needed to prepare mash at a dry solids concentration of 25% (w/w).

A 0.13 g/ml working solution of the alpha amylase (Liquozyme SC DS, Novozymes) was added at a dose of 0.025% (w/w) based on the wet weight of the corn in the slurry. The slurries were sealed and mixed at 50 rpm. Samples were liquefied by incubating at 83° C. for 90 minutes, after which the samples were cooled to 40° and the mass of mash was calculated. The pH of the mash was adjusted to <5.2 by addition of 10 N sulfuric acid. The samples were shaken at 170 rpm at 32° C. Glucoamylase enzyme (starch breakdown process for corn mash) (Spirizyme® Fuel, Novozymes) was prepared as a 0.25 g/mL solution and added at a dose of 0.66% (w/w, based on the wet weight of corn). Antibiotic, Lactrol (Philbro, Ridgefield Park, N.H.), was added to each flask to achieve a concentration of 0.5 ppm (w/w). The resulting corn mash had a 30% glucose concentration (wt/vol).

A 0.1 g/ml suspension of yeast (Saccharomyces cerevisiae; Ethanol Red; Fermentis, Marcqen-Baroeul, France) was prepared in a sterile 250-ml flask and incubated at 40° C. for 20 minutes prior to inoculation into the fermentation containers containing saccharified corn mash feedstock. Nitrogen, as a 0.2 g/mL urea solution was added to a total concentration of nutrient nitrogen of 500 mg N/kg. The flasks were incubated at 32° C. at 170 rpm for 60-120 hours. A dextrose fermentation was run as a control.

Example 4

Blending of Cellulosic-Derived C6 Fermentable Sugars and Starch C6

Sugar compositions derived from ensiled energy sorghum and switch grass were prepared in accordance with Example 2. The cellulosic hydrolysate derived from sorghum and switchgrass comprise approximately 20% (wt/v)C6 sugars. Various blending ratios of corn mash (starch C6 with cellulosic C6) were prepared as follows: For every 100 ml of total whole fermentation broth, the amount of corn mash to cellulosic sugar C6 sugars was blended such that the final concentration of the sugars remained close to 20%. Thus, for the ratio of corn mash to sorghum of 90:10, 90 ml of 25% sugar slurry (wt/v) of corn mash was blended with 10 ml of cellulosic sorghum sugar slurry comprising 20% C6 sugars. In accordance with this protocol, several blends of corn mash and sorghum were prepared wherein the final C6 sugars were close to 20% (wt/v) and final volume of the broth was adjusted, resulting in four samples having a ratio of about 80:20, 70:30, 60:40 and 50:50 corn mash:C6 sugar. A similar process was followed to create fermentation feedstock, which was a blend of corn mash and switchgrass sugars.

Example 5

Ethanol Yield of Corn Mash Blended with Cellulosic C6 Sugars

Prior to fermentation, the sorghum sugar streams were characterized for total solids, total dissolved solids and HPLC analysis of sugar content. The concentrations of total dry solids and dissolved dry solids were measured using standard fermentation procedures. The sugar substrate concentration was analyzed by HPLC for cellobiose, glucose, xylose, galactose, arabinose and mannose. The concentrations of sugar and ethanol were also determined during fermentation by HPLC. Ethanol conversion rate was determined by finding the theoretical maximum of ethanol to be produced by a sample (total glucose (g) x0.55=total ethanol (g)). By using the HPLC, the resulting ethanol after fermentation was compared to the theoretical maximum of ethanol to be generated by the starting glucose level of the sample as fermentation began: (Resulting ethanol)/(Theoretical max Ethanol)=Ethanol Conversion rate.

Figure 2:
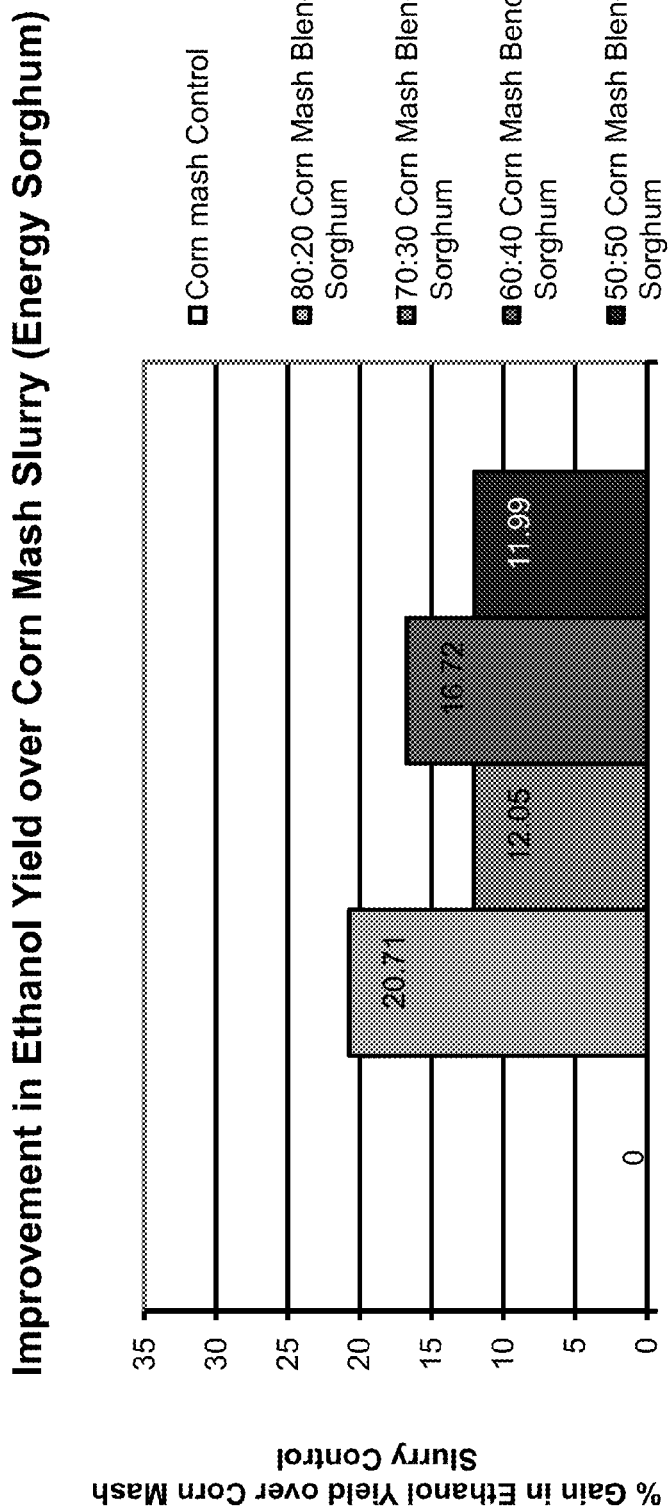
FIG. 2 is a graph illustrating the improvement in ethanol yield for fermentation of corn mash slurry spiked with various energy sorghum-derived sugar blends as compared to fermentation of corn mash slurry alone.

Table 1 and FIG. 2 illustrate the approximate percent gain in ethanol yield over corn mash control in fermentation. The 80:20 corn mash blend with energy sorghum showed a 20.71% increase in ethanol conversion rate, the 70:30 corn mash blend with energy sorghum showed a 12.05% increase in ethanol conversion rate, the 60:40 corn mash blend with energy sorghum showed a 16.72% increase in ethanol conversion rate, and the 50:50 corn mash blend with energy sorghum showed a 11.99% increase in ethanol conversion rate.

TABLE 1

| (g/L) | Initial sugar | Ethanol Yield | % Ethanol Recovered from Theoretical Maximum | Improvement in Ethanol Yield over Corn Mash control (%) |
|---|---|---|---|---|
| 100% Corn Mash - Control | 318.4 | 112.6 | 68.4 | — |
| 80:20 Corn Mash with Energy Sorghum | 265.7 | 117.5 | 82.6 | 20.7 |
| 70:30 Corn Mash with Energy Sorghum | 259.7 | 108.2 | 76.7 | 12.0 |
| 60:40 Corn Mash with Energy Sorghum | 238.1 | 103.5 | 79.9 | 16.7 |
| 50:50 Corn Mash with Energy Sorghum | 256.9 | 107.5 | 76.6 | 12.0 |

Figure 3:
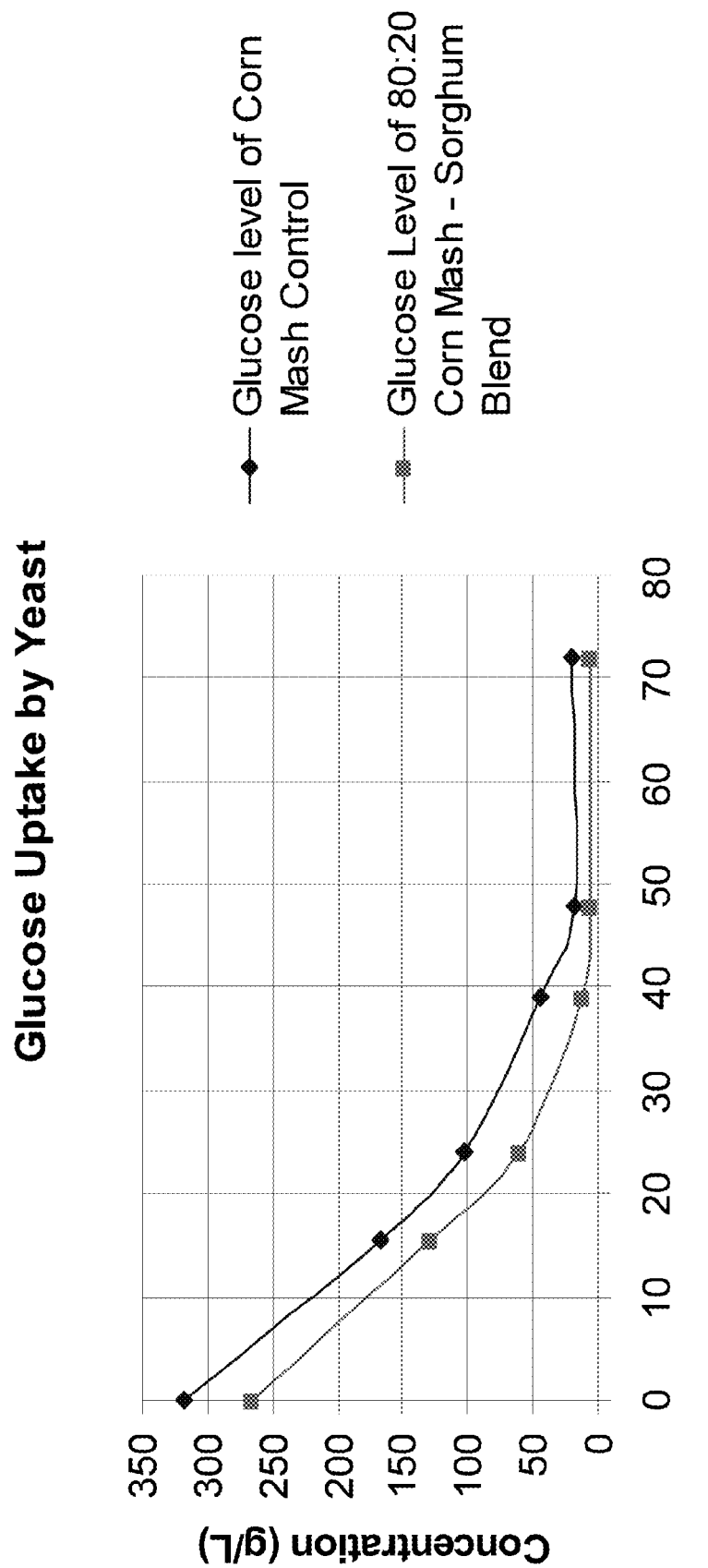
FIG. 3 is a graph of glucose concentration over time for a corn mash control feedstock as compared to a feedstock spiked with sugar from energy sorghum.
Figure 4:
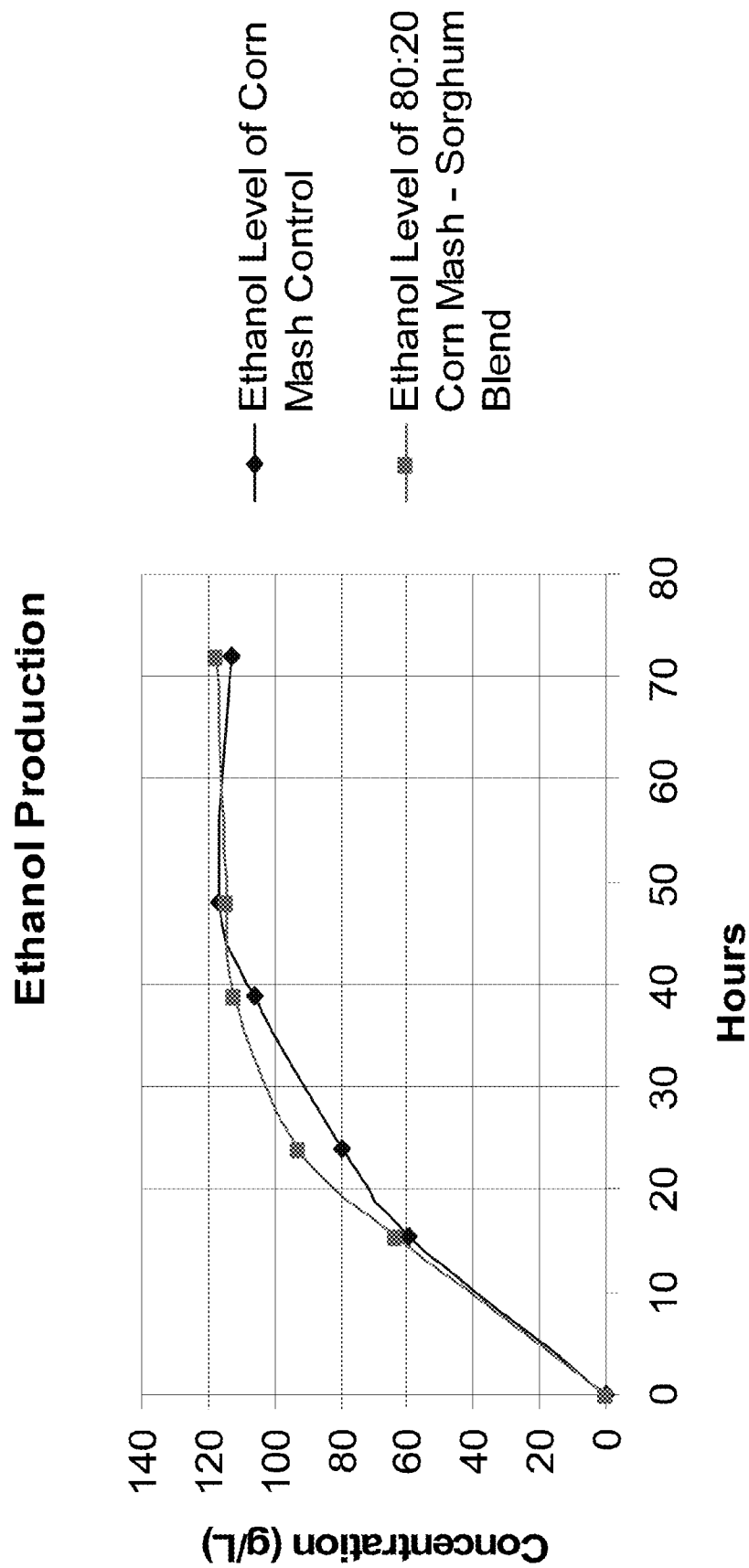
FIG. 4 is a graph comparing ethanol production for a corn mash control against corn mash spiked with energy sorghum sugars.

The results in FIGS. 3 and 4 demonstrate that corn mash fermented with energy-sorghum derived sugar compositions produce a higher efficiency of yeast sugar conversion to ethanol (approximately a 10-15% increase) as well as faster conversion of glucose sugars to ethanol (about 8 hours faster). Although the corn mash feedstock initially had more sugar than the corn mash and cellulosic sugar blends, all samples resulted in approximately the same final concentration of ethanol. Further, the fermentation of 100% corn mash took nearly ten hours longer to produce this final concentration.

Figure 5:
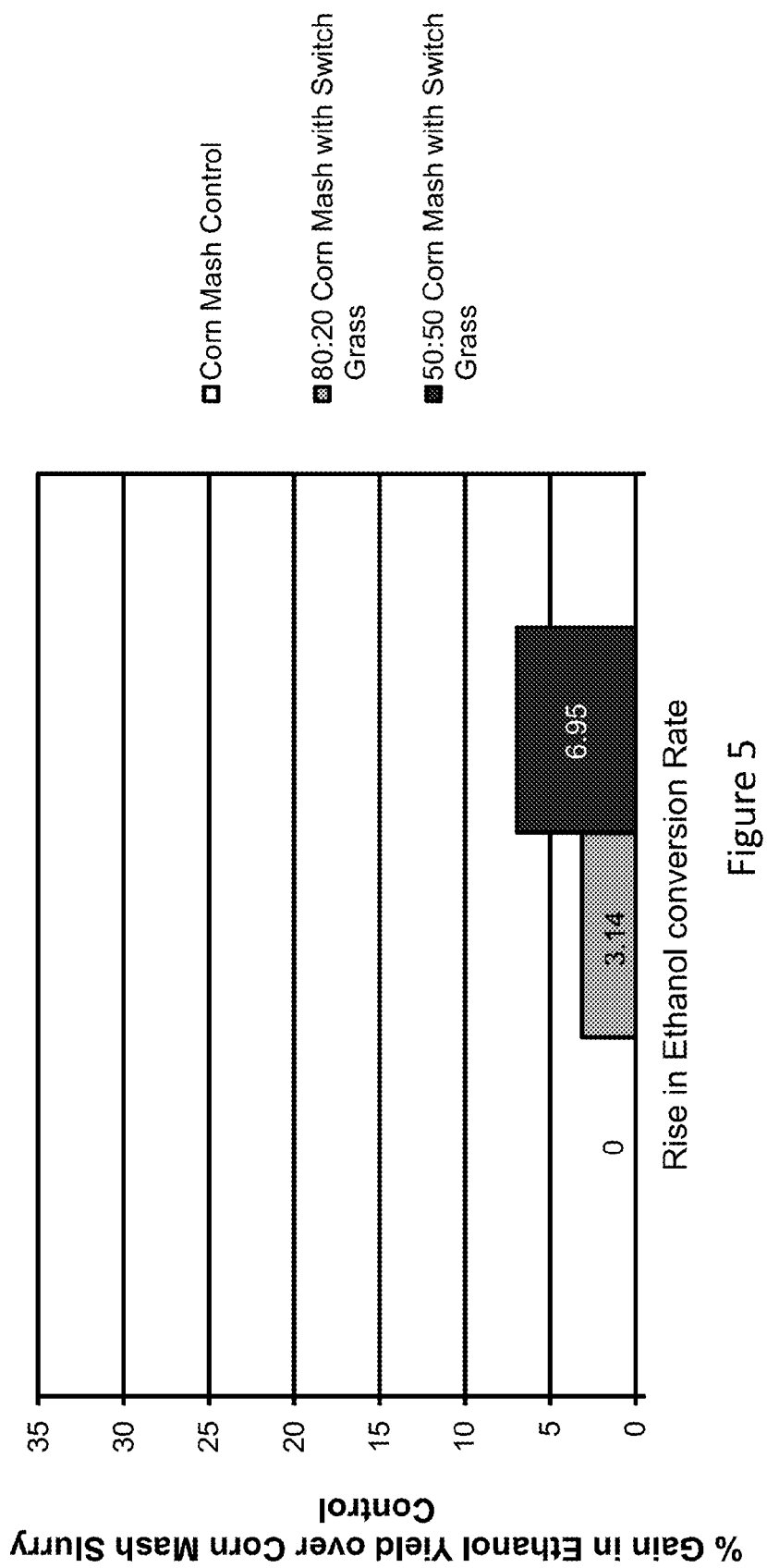
FIG. 5 is a graph illustrating the improvement in ethanol yield for a corn mash slurry spiked with switchgrass-derived sugar as compared to corn mash slurry alone.

Switchgrass cellulosic sugar was blended with corn mash to produce 80:20 and 50:50 corn mash:switchgrass ratio samples. Table 2 and FIG. 5 illustrate the percent gain in ethanol yield over the corn mash control during yeast fermentation. The 80:20 corn mash/switchgrass blend produced a 3.14% rise in ethanol conversion rate, and the 50:50 corn mash blend with switchgrass demonstrated a 6.95% rise in ethanol conversion rate.

TABLE 2

| (g/L) | Initial sugars | Ethanol Yield | % Ethanol Recovered from Theoretical Maximum | Improvement in Ethanol Yield over Corn Mash control (%) |
|---|---|---|---|---|
| 100% Corn Mash - Control | 229.9 | 106.6 | 84.6 | — |
| 80:20 Corn Mash with Switch Grass | 224.3 | 106.2 | 87.3 | 3.1 |
| 50:50 Corn Mash with Switch Grass | 219.3 | 108.5 | 90.5 | 7.0 |

Example 6

Impact of Sugar Compositions on Fermentation

Three 20% glucose solutions were prepared for fermentation. The first was used as a control. The second was spiked with 5 g Switchgrass dry solids. The third feedstock was spiked with 5 g energy sorghum dry solids. The three feedstocks were adjusted to comprise similar total sugar concentrations (see Table 3) and fermented with yeast. The Switchgrass and energy sorghum dry solids comprised the lignins, plant proteins and oils remaining after hydrolysis and removal of soluble C5 and C6 saccharides. The dry solids were filtered, washed, dried and weighed prior to mixing with the glucose.

TABLE 3

| (g/L) | Initial sugar | Ethanol Yield | % Ethanol Recovered from Theoretical Maximum | Improvement in Ethanol Yield over Corn Mash control (%) |
|---|---|---|---|---|
| Glucose Control | 196.3 | 84.4 | 78.2 | — |
| Glucose with 5 g Switchgrass Solids | 191.6 | 96.8 | 91.9 | 17.5 |
| Glucose with 5 g Energy Sorghum Solids | 208.09 | 109.26 | 85.1 | 8.9 |

Figure 6:
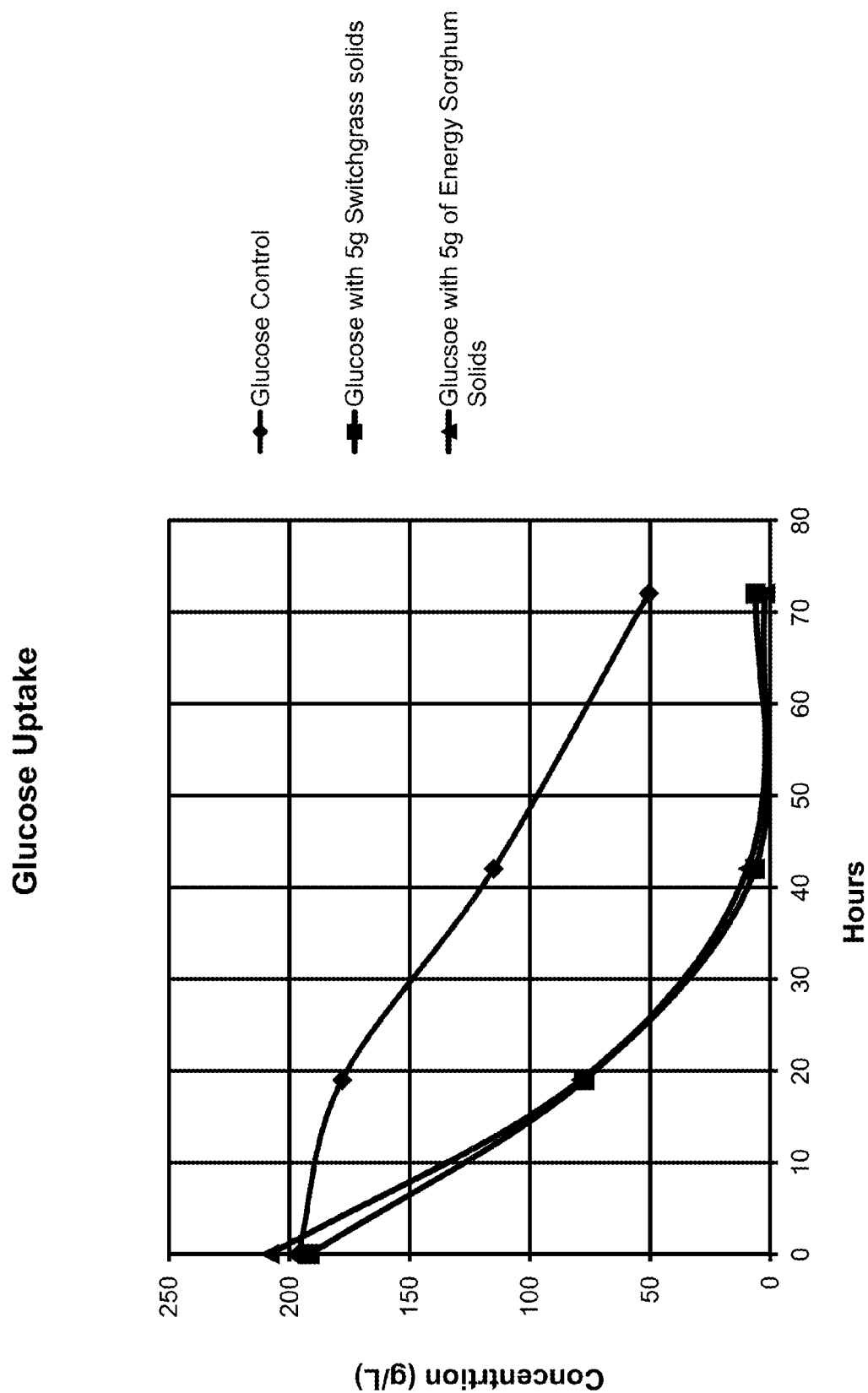
FIG. 6 is a graph comparing glucose uptake for a glucose control as compared to a glucose solution spiked with energy sorghum solids and a glucose solution spiked with switchgrass solids.
Figure 7:
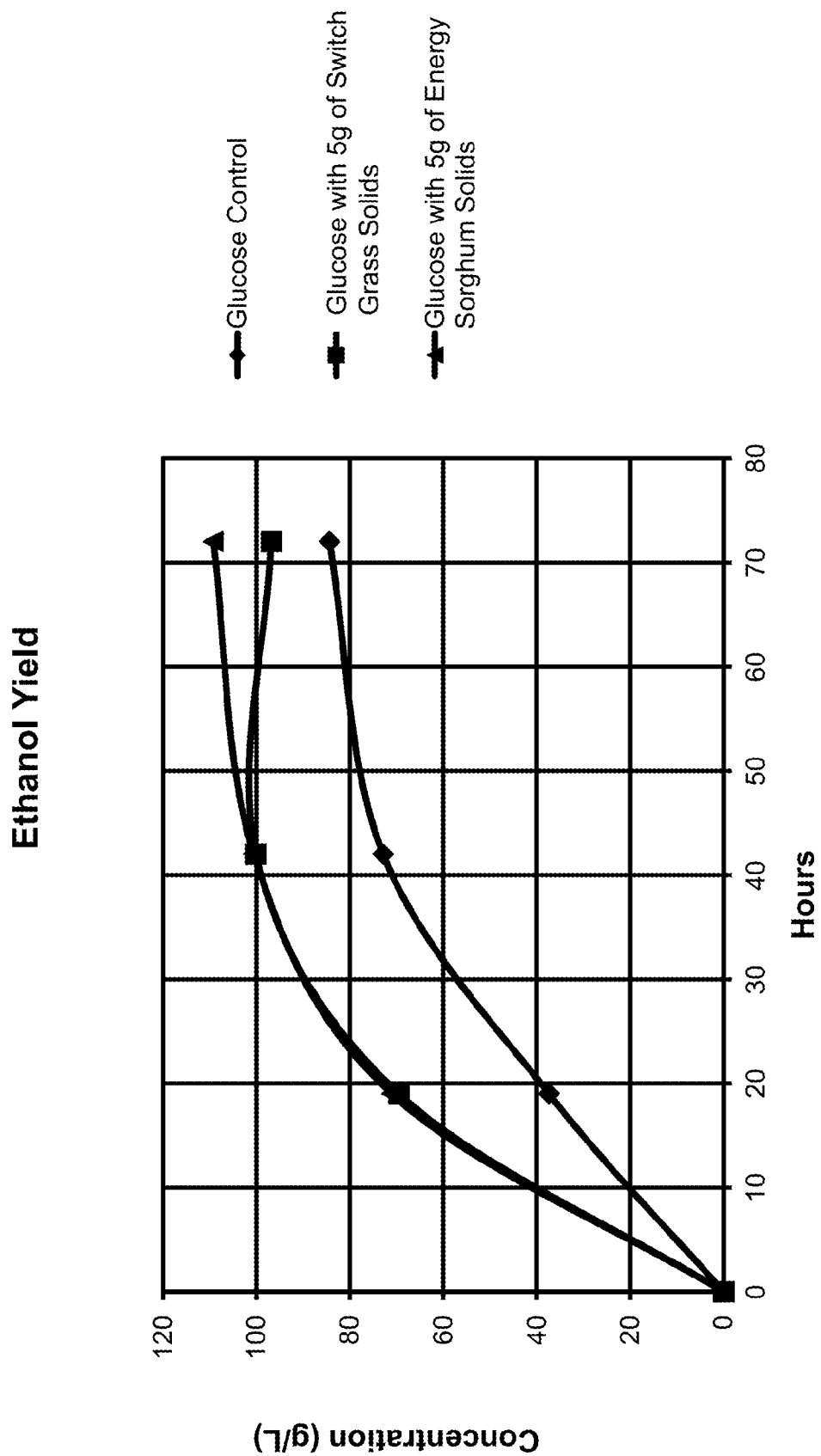
FIG. 7 is a graph comparing ethanol production for a glucose control as compared to a glucose solution spiked with energy sorghum solids and a glucose solution spiked with switchgrass solids.

The results shown in FIGS. 6 and 7 and Table 3 demonstrate that the addition of cellulosic C6 solids to the fermentation broth or growth media stimulate and enhance the conversion of a C6 glucose carbohydrate and/or cellulosic glucose sugar containing sources to ethanol.

Not wishing to be bound by theory, it is believed that the level of nutrient rich ions present in the cellulosic hydrolysate stream enables the yeast to more efficiently and effectively consume glucose. Other mechanisms may also contribute to the observed beneficial effect: 1) appropriate levels of salt (ash) that alter membrane permeability or transport proteins, allowing more glucose into the cell and therefore more ethanol production; 2) appropriate (low) levels of inhibitors may reduce protons on the exterior of the mitochondria in the yeast cell, stimulating processes that seek to maintain the environmental conditions which impacts cell energy generation (these processes would enhance glucose metabolism resulting in higher ethanol production); 3) appropriate levels of trace ions and salts like Zn, Mg, and K in the feedstock increase the pH environment around and in the cell, stimulating enzyme activity resulting in increased ethanol production.

Example 7

Preparation of Corn Stover used for Corn Mash Blending

Corn stover was processed through a steam pretreatment system using only steam and no additional catalysts to prepare a C6-enriched hydrolysate. The pretreatment temperature was 205° C. and the resident time was about 7.5 minutes. Excess C5 sugars and acetic acid that were generated during pretreatment were solubilized and removed using a filter press.

The stover was then added to a 55 gallon jacketed reactor and total solids were brought to about 8% (wt/wt) using water. The pH of the corn stover was adjusted to about 5.0 using sodium hydroxide. The 8% slurry of corn stover contained approximately 5 kg of dry biomass. To this, 1 L of enzymes were added to the broth. This represented approximately 4× the standard dosage (20% of total solids (v/wt)) in order to ensure complete hydrolysis. During enzymatic hydrolysis, the temperature was maintained at approximately 50° C. for about 72 hours with agitation. The total weight of the corn stover plus water was approximately 62.5 kg. The slurry was then centrifuged following hydrolysis to remove all, or substantially all, of the remaining solids from the hydrolyzed sugars and the sugars were then concentrated through evaporation until the C6 sugar level reached about 300 g/L. The sugar solution was sealed and kept at 4° C. until fermentation.

Example 8

Corn Mash Blending with Cellulosic Sugar Derived from Corn Stover

Corn mash oligosaccharides (e.g., starch) containing between about 25% and 30% sugars was blended with monomeric C6 sugar under various fermentation conditions. The monomeric sugars comprised either a solution of pure glucose or a C6-enriched hydrolysate produced from corn stover (e.g., cellulosic sugars) according to the procedure in Example 7. Both sources of monomeric sugars comprised about 25% sugars. The blended feedstocks were then simultaneously saccharified and fermented using a combination of enzymes and yeast.

The corn mash control, undiluted, was saccharified and fermented as is. For the conditions with blended feedstocks, either 80 or 90 grams of corn mash material was weighed out and funneled into the appropriate flask. Following this step, 20 or 10 mL of either a ~25% sterile solution of glucose or ~25% corn stover hydrolysate was added to the corn mash and mixed. Fermentations comprising only pure glucose or the corn stover hydrolysate, had 1 mL of Yeast Nutrient Media added. 1 mL of 5% Urea and 5% Magnesium sulfate solution was added to all samples prior to fermentation, and the pH of each solution was adjusted to 4.8-5.2.

Yeast, propagated beforehand to exponential growth phase, was added to each sample. For each corn mash sample, 50 µL of glucoamylase was added at the same time to initiate the simultaneous saccharification of the corn mash and the yeast fermentation. Samples of the fermentation were analyzed at 2.5, 5, 24, and 96 hours for glucose and ethanol. The results are summarized in Table 4.

Control fermentations were carried out with pure glucose solution or the C6-enriched corn stover hydrolysate. The concentration of sugars in the fermentation reactions was approximately 20%. The glucose and the C6 hydrolysate produced similar yields of ethanol. The pure glucose fermentation produced an ethanol titer of 105.54 g/L after 96 hours; the C6-enriched hydrolysate fermentation reaction produced an ethanol titer of 104.03 g/L after 96 hours. This experiment shows that the C6-enriched hydrolysate yields are similar to a pure glucose solution.

TABLE 4

Summary of fermentation data

| | | Time (hrs) | | | | |
|---|---|---|---|---|---|---|
| | | 0 | 2.5 | 5 | 24 | 96 |
| Glucose Control (20%) | Glucose (g/L) | 192.9 | 162.1 | 130 | 61.54 | 0 |
| | Ethanol (g/L) | 0 | 7.98 | 22.94 | 72.15 | 105.54 |
| Corn Stover Hydrolysate (20% C6) | Glucose (g/L) | 191.9 | 196 | 187.8 | 47.43 | 2.97 |
| | Ethanol (g/L) | 0 | 1.98 | 8.5 | 71.33 | 104.03 |
| SSF Corn Mash Control | Glucose (g/L) | 12.7 | 107.8 | 151.28 | 54.91 | 15.74 |
| | Ethanol (g/L) | 0 | 10.4 | 33.15 | 109.87 | 142.33 |
| SSF Corn Mash:Glucose (80:20) | Glucose (g/L) | 65.9 | 125.8 | 151.49 | 47 | 4.32 |
| | Ethanol (g/L) | 0 | 8.4 | 32.35 | 112.82 | 153.85 |
| SSF Corn Mash:Corn Stover Hydrolysate (80:20) | Glucose (g/L) | 70.1 | 130.3 | 131.35 | 55.04 | 19.93 |
| | Ethanol (g/L) | 0 | 9.1 | 31.23 | 114.11 | 137.79 |
| SSF Corn Mash:Glucose (90:10) | Glucose (g/L) | 28.1 | 132.3 | 153.22 | 45.76 | 8.65 |
| | Ethanol (g/L) | 0 | 9.6 | 32.88 | 117.46 | 153 |
| SSF Corn Mash:Corn Stover Hydrolysate (90:10) | Glucose (g/L) | 41 | 118 | 122.82 | 48.33 | 14.87 |
| | Ethanol (g/L) | 0 | 12 | 33.37 | 112.53 | 150.71 |

Example 9

Fed Batch Fermentation Using Blended Cellulosic-Derived and Non-Cellulosic Sugars Using varying proportions of cellulosic-derived C6 stream, the average ethanol yield of liquefied corn mash was compared to the average ethanol yield of a control containing only water and corn solids. Also, a glucose solution instead of a C6 rich stream was also used as a term of comparison for concentration of products, given the high sugar concentration of the amendments. Fed-batch strategy was also examined to evaluate the performance of the yeast when a C6 sugar rich stream was fed into the fermenter as controlled additions during SSF operations.

Most dry milling operations in the U.S. follow a particular series of steps. They mill the corn, adjust the solids and starch content, cook the corn mash with alpha amylase and, finally, to gain efficiency, carry out SSF with the addition of glucoamylase (GA) and a fermenting yeast in a single vessel. The success of this operation can be determined and driven by several factors such as the starch content in the mash leading to total fermentable sugars (e.g., the higher the sugar content, the higher the amount of ethanol produced); the kind of yeast used (sugar, ethanol and temperature tolerant); the inoculum level of the yeast and fermentation time; the residual sugars at the end of fermentation (most corn ethanol plants prefer to maximize sugar utilization and minimize the presence of residual sugars as it impacts the quality of DDGS on distillation); temperature; the control of the release and presence of monomeric C6 sugars and salts during fermentation; the level of fermentation inhibitors formed (e.g., acetic acid, lactic acid, formic acid, HMF, furfural and lignin produced); the presence of C5 sugars and their concentration in the mash (e.g., xylose can interfere with fermentation as most fermenting yeasts are unable to assimilate this sugar; in this case, addition of a C5 fermenting yeast can be used to achieve complete sugar conversion).

To gain efficiency and lower capital expenditures, most corn dry milling operation currently average about 48 hours of fermentation. A limiting factor, affecting the finishing time, can be the rate of the glucoamylase (GA) addition and the conversion of dextrin's to monomeric C6 sugars. Most operators try to keep glucose levels at about 1% or less at just after 18 hours of fermentation because the glucoamylase is expensive, so it is necessary to be as efficient as possible.

Further, in most of these operations, glucose levels are kept low to reduce osmotic stress on the yeast, especially past 18-24 hours of fermentation when other stressors may begin to impact the yeast (e.g., ethanol, lactic acid, acetic acid, etc.). Dosing GA at a higher concentration typically results 3-5% glucose at 24 hours; however by reducing the GA, a reduction in the glycerol production (presumably from less osmotic stress) is noticed. To achieve optimum availability of monomeric C6 glucose without compromising osmotic stress effects during corn mash fermentation with yeast, a fed-batch operation was carried out wherein cellulosic derived C6 sugar was controlled and 'spoon fed' or fed continuously to the corn mash to insure no excess build up of monomeric C6 sugars in the mash. This strategy enabled the microorganism to get optimum feeding-on-demand monomeric C6 sugar, steering the yeast metabolic pathway away from glycerol while enabling rapid conversion to ethanol.

Corn mash slurry was prepared for the different fermentation treatments (e.g., corn mash only and blended with cellulosic-derived C6 monosaccharides). Briefly, the moisture content of the corn was used to determine the mass of corn needed to prepare mash at a dry-solids concentration of 25% (w/w). The alpha-amylase enzyme (Liquozyme SC DS, Novozymes, U.S.A.) was diluted to ensure more precise delivery of enzyme to each sample. A 0.13-g/ml working solution of the alpha amylase was added at a dose of 0.025% (w/w) based on the wet weight of the corn. The pH was adjusted to 5.7-5.85 using 1N ammonium hydroxide and the samples agitated while incubating at 83° C. for 90 minutes. Following liquidation of the samples, they were cooled to 40° C.

Prior to fermentation, the cellulosic C6 rich stream derived from various feedstocks (e.g., corn stover, wheat straw, energy sorghum, switchgrass, etc.) was prepared using pretreatment procedures that maximize recovery of fermentable saccharides. The fermentations were performed with crude hydrolysates that were characterized for total solids, total dissolved solids and HPLC analysis of sugar content. The concentrations of total dry solids and dissolved dry solids were measured using standard NREL procedures. The sugar substrate concentration was analyzed by HPLC for C5 sugars and glucose as C6.

Characterization of a C6 Rich Stream

A C6 rich stream was prepared from processing corn stover that was pretreated in a commercial Biogasol unit capable of processing 100MT dry biomass per day with dilute $H_2SO_4$ (15 minutes at 170° C. with 0.6%, $H_2SO_4$). The C5 sugars were separated and the C6/lignin rich solids were enzyme hydrolyzed with Novozyme Cellic Ctec3 cellulase enzymes. Post hydrolysis, the lignin was separated and the C6 rich stream with a residual amount of C5 was further concentrated to 25% solubilized solids.

The contents of the cellulose hydrolysis stream (C6 rich stream) is shown in Table 5 below.

TABLE 5

Characterization of cellulosic C6 stream

| pH | Dissolved solids (% w/w) | Acetic acid % | HMF % | C5 as Xylose (% w/v) | Glucose (% w/v) |
|---|---|---|---|---|---|
| 5.0 | 25.44 | 0 | 0 | 2.5 | 23.48 |

The mass of the cooled mash was calculated for each sample. The pH of the mash was adjusted to <5.2 by addition of 1-N sulfuric acid.

All enzymes, nutrients, and other amendments added to the fermentation flasks were freshly prepared before use. The total concentration of nutrient nitrogen as urea was 500 mg N/kg to a final concentration of 500 ppm as nitrogen (w/w, based on the total mass of mash). The glucoamylase enzyme (Spirizyme Fuel, Novozymes) was prepared as a 0.25 g/ml solution and added at a dose of 0.066% (w/w, based on the wet weight of corn). Antibiotic, FermGuard Xtreme (Ferm Solutions, Inc, Danville, Ky.), was added to each sample as a dose of 0.5 ppm (w/w). Yeast extract (0.16 g) was added to the glucose treatment that fermented with no corn solids.

A 0.1 g/ml suspension of yeast (*Saccharomyces cerevisiae*; FermaxGreen and FermaxGold Ethanol Red; Fermentis, Marcq-en-Baroeul, France) was prepared in a sterile 1 L flask having the corn mash with glucoamylase. This suspension was incubated and mixed for 6 hours at 34° C. prior to inoculation of a 6.5% volume of the suspension into a sample.

The mass of each sample was recorded after all additions were made, and the samples were incubated at 32° C. with agitation for 62 hours.

TABLE 6

Summary design of cellulosic-C6 rich stream to water ratio per treatment for determination of effects on ethanol yield

| TREATMENT | TYPE OF SOLUTION | SOLUTION: CORN MASH SLURRY RATIO |
|---|---|---|
| 10% | Cellulosic-C6 rich | 10:90 |
| 20% | Cellulosic-C6 rich. | 20:80 |
| Glucose | Control | Glucose, 250 g/L: 0 |
| Fed batch | Cellulosic-C6 rich | 10:90 |
| 10 L | (46% C6 solution) | 1 L fed to 9 L corn mash |

Samples were collected at various time intervals and the combined mass of the mash and sample was measured. The samples were analyzed for concentrations of substrates (glucose, subunits, residual xylose) and products (ethanol, glycerol, lactic acid, and acetic acid) by HPLC. The remaining samples were collected at the end of fermentation and analyzed for pH and substrate/product concentrations. The final concentrations of total dry solids and dissolved dry solids were measured after incubation for 62 hours Fed Batch Operation Partially dextrinized corn mash was charged in a 30 L C-30 Sartorius stainless steel Steam In Place (SIP) bioreactor, pH adjusted to 5 with 1N KOH and the temperature maintained at 32° C. The yeast was propagated separately. Glucoamylase enzyme (Spirizyme Fuel, Novozymes) was prepared as a 0.25 g/ml solution and added at a dose of 0.066% (w/w, based on the wet weight of corn). Antibiotic, FermGuard Xtreme, was added to each tank to achieve a dose of 0.5 ppm (w/w).

The yeast inoculum was prepared by adding 0.15 g of dried matrix green and matrix gold yeast to the corn mash, at pH 5 with KOH and propagated for 6 hr. Seed was inoculated into the fermenter at 6.5% v/w (T=0 hr). The fermenter operating parameters were as follows: temperature 34° C., RPM=300, feed rate of cellulosic derived C6 rich stream (1 L of 48% w/v sugar as C6 and 4.3% w/v C5 as xylan) was fed continuously and controlled at a feed rate of 0.7 ml/min. During the first 24-36 h of the operation, 1 L of the C6 rich solution was drained into the fermenter. Samples were drawn at time intervals and analyzed for residual sugars and progress of ethanol fermentations. In some samples, an engineered yeast that was capable of fermenting C6 glucose and C5 sugar (xylose) was used. The intent was to test and see if mixed cultures of C6 and an engineered C5 fermenting yeast assist in successful fermentation of sugar mixtures of glucose and xylose in the corn mash.

Fed Batch Operation in 2 L (Seed Propagator) and 30 L Automatic Fermenters (Sartorius, Pa.)

TABLE 7

HPLC DROP RESULTS (w/v) except Ethanol (v/v)

| Sample | T (h) | Tot. Sug. | DP4S | DP3S | DP2S | Glu | Fruc. | Lact. Acid | Glyc. | Ac. Acid | EtOH |
|---|---|---|---|---|---|---|---|---|---|---|---|
| Cont. 1 | 48 | 2.26 | 1.33 | 0.47 | 0.25 | 0.17 | 0.04 | 0.16 | 1.75 | 0.03 | 15.71 |
| Cont. 2 | 48 | 2.54 | 1.52 | 0.48 | 0.26 | 0.24 | 0.04 | 0.21 | 1.75 | 0.02 | 15.44 |
| Cont. 3 | 48 | 1.96 | 1.04 | 0.46 | 0.23 | 0.19 | 0.04 | 0.18 | 1.77 | 0.03 | 15.7 |
| Test 4 (90:10) | 48 | 2.88 | 1.15 | 0.71 | 0.36 | 0.25 | 0.41 | 0.15 | 1.45 | 0.03 | 16.32 |
| Test 5 (90:10) | 48 | 2.66 | 1 | 0.68 | 0.39 | 0.17 | 0.42 | 0.15 | 1.45 | 0.03 | 16.35 |
| Test 6 (90:10) | 48 | 2.69 | 1.03 | 0.69 | 0.36 | 0.2 | 0.41 | 0.13 | 1.43 | 0.04 | 16.2 |
| Test 1 (80:20) | 48 | 3.24 | 1.08 | 0.76 | 0.5 | 0.12 | 0.78 | 0.15 | 1.26 | 0.05 | 16.84 |
| Test 2 (80:20) | 48 | 3.27 | 1.1 | 0.76 | 0.49 | 0.14 | 0.78 | 0.15 | 1.25 | 0.04 | 16.71 |

TABLE 7-continued

| Sample | T (h) | Tot. Sug. | DP4S | DP3S | DP2S | Glu | Fruc. | Lact. Acid | Glyc. | Ac. Acid | EtOH |
|---|---|---|---|---|---|---|---|---|---|---|---|
| Test 3 (80:20) | 48 | 3.3 | 1.08 | 0.77 | 0.5 | 0.16 | 0.79 | 0.16 | 1.27 | 0.05 | 16.89 |

Cont.: Control (corn mash only); T (h): Time in hours; Tot. Sug.: Total Sugars; DP4S: saccharides with 4 degrees of polymerization; DP3S: saccharides with 3 degrees of polymerization; DP2S: saccharides with 2 degrees of polymerization; Glu.: Glucose; Fruc.: Fructose; Lact. Acid: Lactic Acid; Glyc.: Glycerol; Ac. Acid: Acetic Acid; EtOH: Ethanol.

As shown in Table 7, fed-batch fermentations blending corn mash with cellulosic-derived C6 monosaccharides resulted in higher yields of ethanol and lower yields of glycerol after 48 hours as compared to control fermentations of corn mash only.

Fed batch fermentations of cellulosic C6 rich sugar from wheat straw (WS) blended with corn mash at an 90:10 or 80:20 ratio (corn mash:wheat straw) were performed in an automated 30 L system. The results of the fermentation were compared to control batch process fermentations of blended feedstocks at the same ratio. All fermentations were inoculated with three strains of industrial C6 fermenting yeasts and one genetically engineered yeast that can ferment both C5 and C6 sugars. The results are shown in Table 8 and FIGS. 10 and 11.

TABLE 8

Fed-batch vs. batch fermentation.

| Treatment | Glucose (g/L) | Xylose (g/L) | Formic Acid (g/L) | Acetic Acid (g/L) | Ethanol (g/L) |
|---|---|---|---|---|---|
| Corn Mash (CM) T0 | 21.15 | 4.55 | 0.4 | 3.54 | 3.35 |
| 30 L fed batch 90:10 CM:WS T5 | 172.9 | 1.55 | 0.3 | 8.17 | 22.8 |
| 30 L fed batch 90:10 CM:WS T18 | 36.65 | 3.1 | 0.6 | 17.82 | 99.1 |
| 30 L fed batch 90:10 CM:WS T36 | 10.55 | 5.7 | 0.85 | 16.76 | 124.2 |
| 30 L fed batch 90:10 CM:WS T48 | 3.65 | 6.4 | 0.9 | 18.97 | 143.85 |
| Control Batch Process 90:10 T0 | 53.7 | 4.4 | 0.4 | 3.29 | 1.8 |
| Control Batch Process 90:10 T5 | 146.65 | 0.75 | 0.25 | 3.06 | 3 |
| Control Batch Process 90:10 T18 | 110.3 | 3.3 | 0.45 | 10.88 | 51.35 |
| Control Batch Process 90:10 T36 | 2.15 | 0.85 | 0.5 | 11.92 | 105.15 |
| Control Batch Process 90:10 T48 | 2.9 | 4.65 | 0.65 | 13.58 | 118.25 |

The fed batch runs indicated initial significant improvement in ethanol volume productivity in g/l/h. Combining cellulosic derived C6 sugar with corn mash as a fed batch process produces higher ethanol production in a shorter amount of time over the first portion of the fermentation in the 30 L and flask samples. The fed batch process not only has shown an increase in ethanol production compared to corn mash on its own, it has also shown to be superior to batch process where all of the cellulosic sugar in the blend is added initially in fermentation. Further optimization with the mixed culture of C6 and C5 fermenting yeast in the 30 L reactor resulted in higher ethanol titers (25%) and reduced the amount of residual sugar in solution, especially in the remaining C5 portion.

Figure 8:
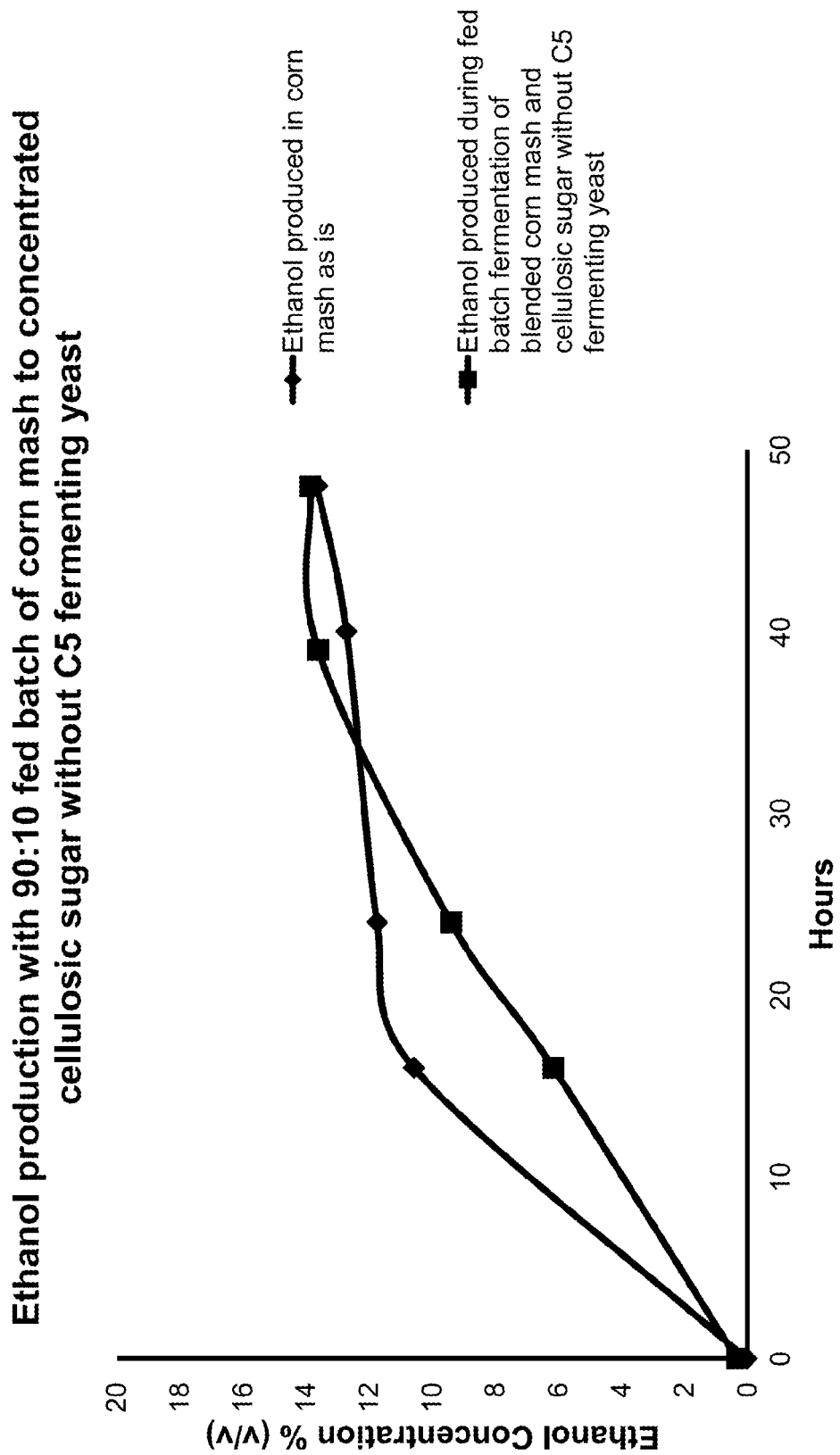
FIG. 8 is a graph comparing ethanol production from corn mash to ethanol production from a fed batch fermentation of a 90:10 blend of corn mash and cellulosic sugar with C5 fermenting yeast.

FIG. 8 shows that by feeding a higher concentration of cellulosic sugar over time, higher ethanol production can be achieved when cellulosic sugar is blended with corn mash after 48 hours and in a shorter amount of time. Residual sugar in both fermentations was under 0.13% v/v. The C5 portion of solution remained mostly unfermented due to the lack of C5 fermenting microbe.

Figure 9:
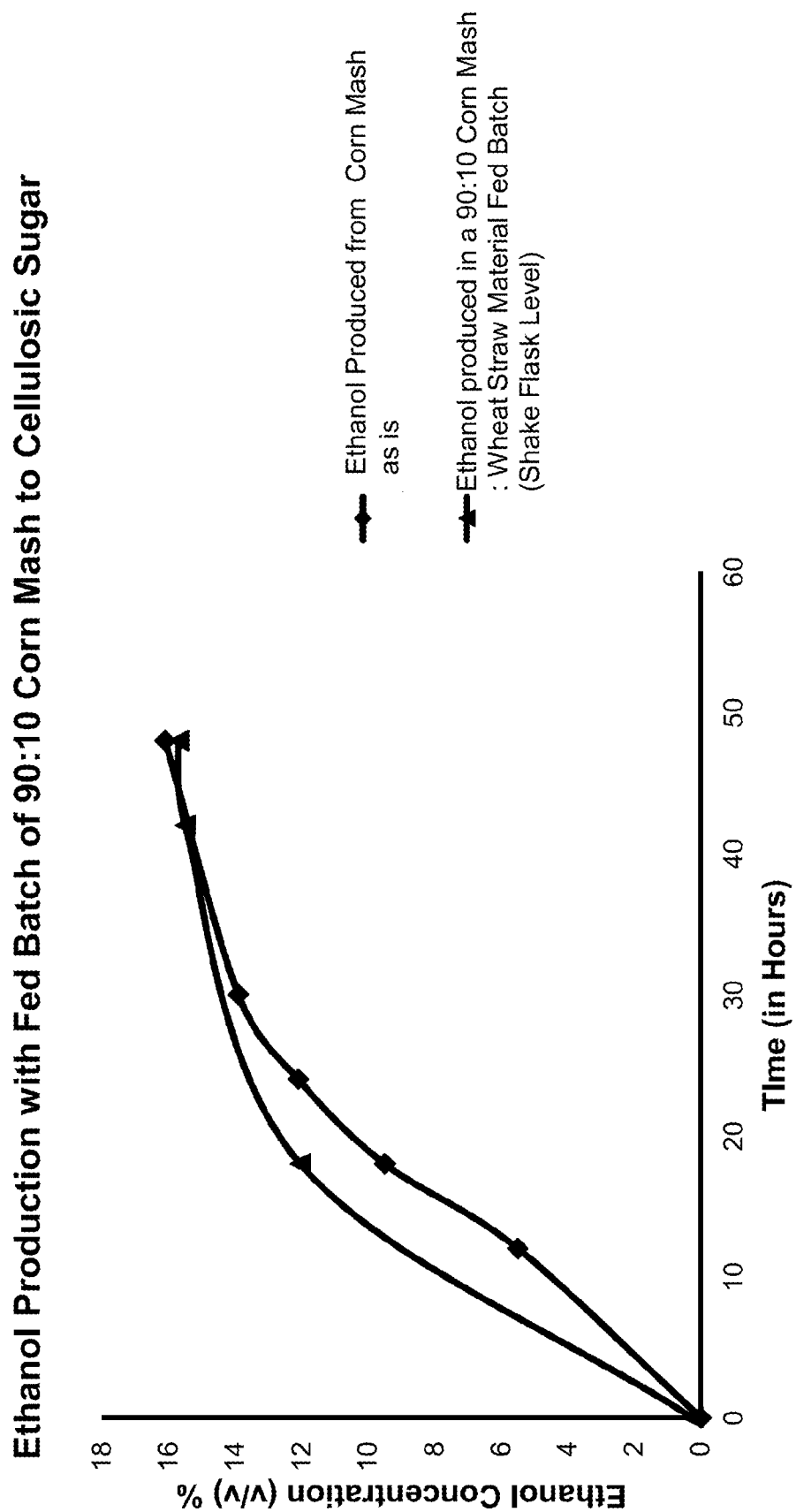
FIG. 9 is a graph comparing ethanol production from corn mash to ethanol production from a fed-batch fermentation of a 90:10 blend of corn mash and wheat straw cellulosic sugar at shake flask level.

FIG. 9 shows the amount of ethanol produced in a 90:10 blend of corn mash and cellulosic sugar at the shake flask level vs. the ethanol production in standard corn mash from as is, at an industrial size scale. The addition of cellulosic sugar throughout the fermentation can account for the increase in ethanol production at the beginning of the fermentation.

Figure 10:
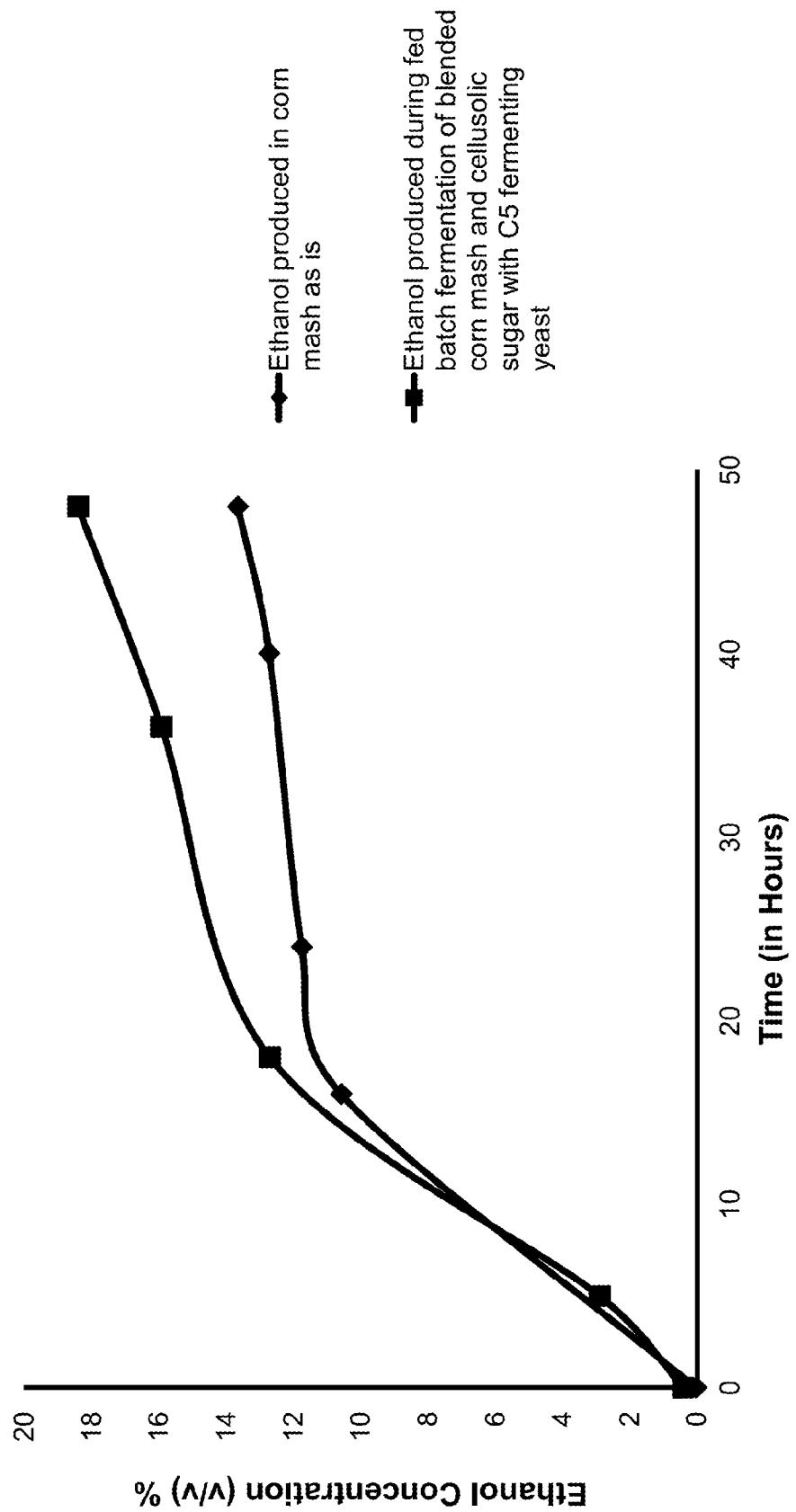
FIG. 10 is a graph comparing ethanol production from corn mash to ethanol production from a fed batch fermentation of a 90:10 blend of corn mash and cellulosic sugar with a C5 fermenting yeast.

FIG. 10 illustrates the results of fed batch replacement of 10% of the corn mash with 10% concentrated cellulosic sugar solution (52% total C5 and C6 sugar). There was an increase of 4.75% v/v ethanol by this method than with corn mash without any blending. The standard yeast combined with a C5 and C6 fermenting yeast strain led to a higher ethanol yield.

Figure 11:
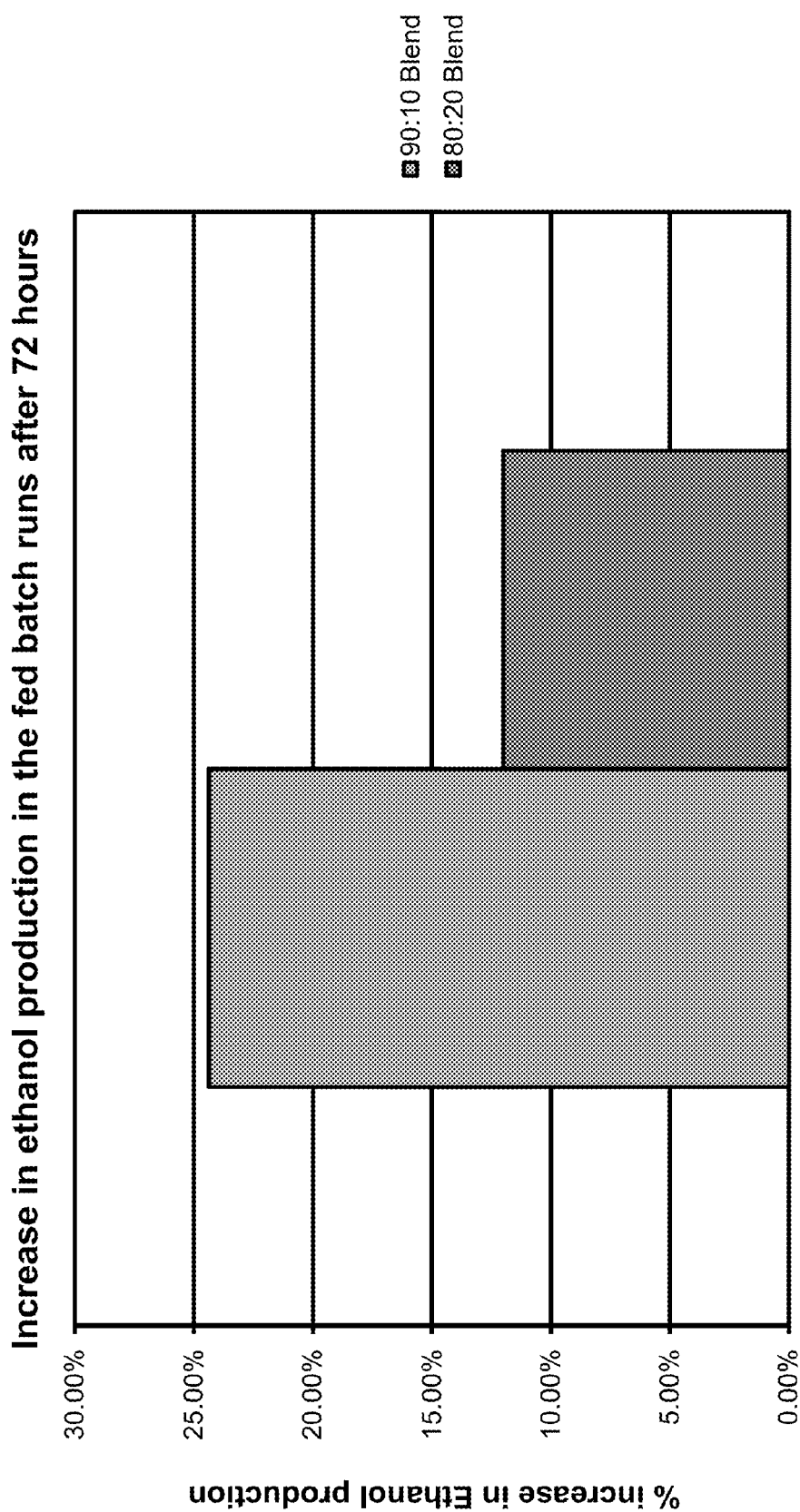
FIG. 11 is a graph showing the increase in ethanol production in fed-batch fermentations compared to batch fermentations after 72 hours using a 90:10 and a 80:20 blend of corn mash and cellulosic sugars.

FIG. 11 shows the percent increase in ethanol production between the 90:10 and 80:20 blended flasks of corn mash with cellulosic sugar derived from wheat straw. The 90:10 fed batch run had a 24.63% increase in ethanol production compared to the batch run in a 90:10 ratio. The 80:20 fed batch blend also saw positive improvement, yielding 12% of an ethanol increase compared to the batch run in the same blend.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of producing one or more fermentation end-products comprising:
   (a) combining a composition comprising a biomass and a liquid, with a solution comprising a cellulosic hydrolysate comprising about 10% to about 70% w/v of C6 monosaccharides to produce a blended feedstock;
   (b) contacting the blended feedstock with one or more biocatalysts; and
   (c) fermenting the blended feedstock to produce one or more fermentation end-products;
   wherein the biomass comprises corn, corn mash, sugar cane, sugar beets, sugar palms, sweet sorghum, nypa palm, cassava, rice, milo, sorghum, sweet potatoes, wheat, molasses, tubers, roots, stems, whole grains, barley, rye, milo, sago, cassava, tapioca, rice, peas, beans, potatoes, beets, fruits, or a combination thereof, and wherein the cellulosic hydrolysate is prepared by a method comprising
pretreating liqnocellulosic material with hot water or dilute acid to solubilize hemicellulose in the liqnocellulosic material,
substantially separating the solubilized hemicellulose from remaining lignocellulosic solids, and
enzymatically hydrolyzing cellulose in the remaining lignocellulosic solids to obtain the cellulosic hydrolysate,
wherein less than 20% of the total saccharides in the cellulsoic hydrolysate are C5 saccharides.

2. The method of claim 1, wherein a yield of at least one of the one or more fermentation end-products is increased relative to fermentation of the biomass without the cellulosic hydrolysate.

3. The method of claim 1, wherein a yield of at least one of the one or more fermentation end-products is increased by at least 5% relative to fermentation of the biomass without the cellulosic hydrolysate.

4. The method of claim 1, wherein at least one of the one or more fermentation end-products is produced at a rate that is faster relative to fermentation of the first biomass without the cellulosic hydrolysate.

5. The method of claim 1, wherein the one or more fermentation end-products comprise one or more alcohols.

6. The method of claim 1, wherein the one or more fermentation end-products comprise ethanol.

7. The method of claim 1, wherein the method is a fed-batch fermentation wherein the solution is added over time.

8. The method of claim 7, wherein a yield of one or more by-products is decreased relative to a non-fed batch fermentation.

9. The method of claim 8, wherein the one or more by-products comprise methanol, glycol, glycerol, erythritol, threitol, arabitol, xylitol, ribitol, mannitol, sorbitol, dulcitol, fucitol, iditol, inositol, volemitol, isomalt, maltitol, lactitol, polyglycitol, or a combination thereof.

10. The method of claim 8, wherein the concentration of C6 monosaccharides in the solution is from about 20% to about 55% w/v.

11. The method of claim 1, wherein the C6 monosaccharides are at a concentration in the solution that differs from a monosaccharides equivalent concentration of saccharides in the composition by less than 50%.

12. The method of claim 11, wherein the composition and the solution are combined in about an 80:20 v/v ratio.

13. The method of claim 11, wherein the composition and the solution are combined in about a 90:10 v/v ratio.

14. The method of claim 1, wherein the C6 monosaccharides are at a concentration in the solution that differs from a monosaccharides equivalent concentration of saccharides in the composition by less than 40%.

15. The method of claim 1, wherein the C6 monosaccharides are at a concentration in the solution that differs from a monosaccharides equivalent concentration of saccharides in the composition by less than 30%.

16. The method of claim 1, wherein the C6 monosaccharides are at a concentration in the solution that differs from a monosaccharides equivalent concentration of saccharides in the composition by less than 20%.

17. The method of claim 1, wherein less than 10% of the total saccharides in the cellulosic hydrolysate are C5 saccharides.

18. The method of claim 1, wherein about 0.1% to about 10% of the total saccharides in the cellulosic hydrolysate are C5 saccharides.

19. The method of claim 1, wherein combining the solution and the composition occurs during fermentation at a rate of about 0.01-5 mL/min of the solution per L of the composition.

20. The method of claim 1, wherein the one or more biocatalysts comprise one or more fermenting microorganisms.

21. The method of claim 20, wherein the one or more fermenting microorganisms comprise a C6 fermenting microorganism.

22. The method of claim 20, wherein the one or more fermenting microorganisms comprise one or more yeast strains.

23. The method of claim 22, wherein the one or more yeast strains comprise a *Saccharomyces* or a *Zygosaccharomyces* strain.

24. The method of claim 20, wherein the one or more biocatalysts further comprise one or more enzymes.

25. The method of claim 24, wherein the one or more enzymes comprise an endoglucanase, an exoglucanase, a cellobiohydrolase, a cellulase, a beta-glucosidase, a glycoside hydrolase, a glycosyltransferase, a lyase, an esterase, a glucamylase, or a combination thereof.

* * * * *

UNITED STATES PATENT AND TRADEMARK OFFICE
CERTIFICATE OF CORRECTION

PATENT NO. : 8,765,430 B2  
APPLICATION NO. : 13/731633  
DATED : July 1, 2014  
INVENTOR(S) : Sarad Parekh et al.

Page 1 of 1

It is certified that error appears in the above-identified patent and that said Letters Patent is hereby corrected as shown below:

In the Claims

COLUMN 63, LINE 3, CLAIM 1:
"liqnocellulosic" should read --lignocellulosic--

COLUMN 63, LINES 4, 5, CLAIM 1:
"liqnocellulosic" should read --lignocellulosic--

COLUMN 63, LINE 23, CLAIM 2:
"fermentation of the first biomass" should read --fermentation of the biomass--

Signed and Sealed this
Sixteenth Day of September, 2014

Michelle K. Lee
*Deputy Director of the United States Patent and Trademark Office*